(12) United States Patent
Amano et al.

(10) Patent No.: US 10,969,218 B2
(45) Date of Patent: Apr. 6, 2021

(54) MEDICINE PHOTOGRAPHING DEVICE

(71) Applicant: YUYAMA MFG. CO., LTD., Toyonaka (JP)

(72) Inventors: Hirokazu Amano, Toyonaka (JP); Koji Ito, Toyonaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 807 days.

(21) Appl. No.: 15/129,798

(22) PCT Filed: Mar. 31, 2015

(86) PCT No.: PCT/JP2015/060090
§ 371 (c)(1),
(2) Date: Apr. 27, 2017

(87) PCT Pub. No.: WO2015/152225
PCT Pub. Date: Oct. 8, 2015

(65) Prior Publication Data
US 2017/0264867 A1    Sep. 14, 2017

(30) Foreign Application Priority Data

Mar. 31, 2014  (JP) .............................. JP2014-071130
Jun. 19, 2014  (JP) .............................. JP2014-126029

(51) Int. Cl.
*H04N 7/18*   (2006.01)
*A62B 1/04*   (2006.01)
(Continued)

(52) U.S. Cl.
CPC ............ *G01B 11/24* (2013.01); *A61B 90/361* (2016.02); *G01N 21/255* (2013.01); *G01N 21/84* (2013.01);
(Continued)

(58) Field of Classification Search
USPC ....................... 348/68, 67, 61, 86, 153, 151
See application file for complete search history.

(56) References Cited

U.S. PATENT DOCUMENTS 5,960,104 A * 9/1999 Conners ............. G01N 21/8986
                                                    144/402
6,427,128 B1 * 7/2002 Satake .................. G01N 21/85
                                                    209/580
(Continued)

FOREIGN PATENT DOCUMENTS

JP    H05-245186 A     9/1993
JP    2001041895 A     12/1993
(Continued)

OTHER PUBLICATIONS

JP 2014-221134 Machine Translation, Nakasaki Shotaro(Year: 2014).*
(Continued)

*Primary Examiner* — Daquan Zhao
(74) *Attorney, Agent, or Firm* — Masuvalley & Partners

(57) ABSTRACT

Provided is a medicine identifying system which enables automatization of medicine identification. A medicine identifying system is constituted of a medicine photographing device and a computer. Medicine identifying software is installed in the computer. At the time of performing medicine identification, a user first sets a medicine to be identified in the medicine photographing device. Next, the medicine photographing device starts to photograph the medicine by using an operation of the user with respect to the computer as a trigger. A photographed image of the medicine is transmitted to the computer as data. Then, the medicine identifying software refers to a database based on this image data to search the medicine.

21 Claims, 43 Drawing Sheets

(51) Int. Cl.

| | | |
|---|---|---|
| *G01B 11/24* | (2006.01) | |
| *G01N 21/95* | (2006.01) | |
| *A61B 90/00* | (2016.01) | |
| *G01N 21/25* | (2006.01) | |
| *G01N 21/84* | (2006.01) | |
| *G06T 7/00* | (2017.01) | |
| *H04N 5/225* | (2006.01) | |
| *H04N 3/40* | (2006.01) | |
| *H04N 3/36* | (2006.01) | |
| *G16H 20/13* | (2018.01) | |
| *G16H 30/20* | (2018.01) | |

(52) U.S. Cl.
CPC ....... *G01N 21/9508* (2013.01); *G06T 7/0012* (2013.01); *H04N 5/2256* (2013.01); *H04N 7/181* (2013.01); *G01N 2201/062* (2013.01); *G16H 20/13* (2018.01); *G16H 30/20* (2018.01)

(56) References Cited

U.S. PATENT DOCUMENTS

| | | | |
|---|---|---|---|
| 8,345,989 B1 | 1/2013 | Bresolin et al. | |
| 2004/0201586 A1* | 10/2004 | Marschner | G06K 9/4661 345/426 |
| 2009/0205796 A1* | 8/2009 | MacHattie | D21G 9/0036 162/198 |
| 2011/0185835 A1* | 8/2011 | Bergamasco | C12M 23/10 74/471 R |

FOREIGN PATENT DOCUMENTS

| | | | | |
|---|---|---|---|---|
| JP | H5-337168 A | 12/1993 | | |
| JP | H09-16681 A | 1/1997 | | |
| JP | H9-253163 A | 9/1997 | | |
| JP | 2004-167158 A | 6/2004 | | |
| JP | 2008-018230 A | 1/2008 | | |
| JP | 2010-117331 A | 5/2010 | | |
| JP | 2011-170891 A | 9/2011 | | |
| JP | 2012-165876 A | 9/2012 | | |
| JP | 2012-183182 A | 9/2012 | | |
| JP | 5033267 B1 | 9/2012 | | |
| JP | 2013-066533 A | 4/2013 | | |
| JP | 2013-070752 A | 4/2013 | | |
| JP | 2013-144100 A | 7/2013 | | |
| JP | 2013137775 A | 7/2013 | | |
| JP | 2014-053791 A | 3/2014 | | |
| JP | 2014-221134 A | 11/2014 | | |
| JP | 2014221134 A | * 11/2014 | ................ | A61J 3/00 |
| KR | 20120012130 A | 2/2012 | | |
| WO | 2004/112685 A1 | 12/2004 | | |

OTHER PUBLICATIONS

Lighting Solution (Year: 2014).*
ISA/JP, International Search Report issued in PCT/JP2015/060090, dated Jun. 2, 2015, total 4 pages with English translation.
Japanese Office Action dated Dec. 24, 2019, Japanese Patent Application No. 2019-024898, 15 Pages.
Japanese Office Action dated Apr. 14, 2020, for Japanese Patent Application No. 2019-024898, total 13 Pages.
Japanese Office Action dated Sep. 29, 2020, issued in Japanese Application No. 2019-193769, 11 pages with translation.
KIPO, Korean Office Action dated Dec. 23,2020 in Korean Application No. 10-2016-7027035, with English translation 24pages.

* cited by examiner

FIG.36

(a)
Do you want to print?
Medicine name: AAAAAAAAAA
The number of tablets: NN

[Yes (Y)]          [No (N)]

(b)
There are X NG medicines. Do you want to print?
Medicine name: AAAAAAAAAA
The number of tablets: NN

[Yes (Y)]          [No (N)]

(c)
Please check "Entire image, lower side".
[OK]

MEDICINE PHOTOGRAPHING DEVICE

This application is the U.S. National Phase of and claims priority to International Application No. PCT/JP2015/060090, International Filing Date Mar. 31, 2015, which claims benefit of Japanese Patent Application No. 2014-071130 filed on Mar. 31, 2014 and Japanese Patent Application No. 2014-126029 filed on Apr. 19, 2014; all of which are incorporated herein by reference in their entireties for all purposes.

TECHNICAL FIELD

The present invention relates to a medicine photographing device for photographing an image of a medicine and medicine identifying software for identifying the medicine.

BACKGROUND OF DISCLOSURE

Currently, one patient often visits a plurality of medical institutions to have medical examinations. In this case, each doctor needs to know what kind of medicine has been prescribed to the patient by other medical institutions. For this purpose, each doctor often asks the patient to bring medicines prescribed by the other medical institutions when the patient visits each medical institution. In this case, if an identification code for the prescribed medicine is printed on a package in which the prescribed medicine is contained, it is possible to immediately identify the kind of the prescribed medicine. However, if the identification code for the prescribed medicine is not printed on the package or the patient brings the prescribed medicine to the medical institution in a state that the medicine is not contained in the package, the medical institution needs to identify the prescribed medicine based on only an external appearance of the prescribed medicine. This operation is referred to as "identification operation". Generally, this identification operation is performed by a pharmacist or a technician. In the present circumstances, the pharmacist manually identifies an unidentified medicine based on a size, a shape, a color and the like of the medicine. Unfortunately, this identification operation is very difficult and wastes a lot of time, thus this identification operation is a heavy burden for the pharmacist.

In order to reduce this burden, there has been developed that a medicine identifying apparatus which can automatically identify a medicine (see Patent documents 1: JP H09-16681A and 2: JP H05-245186). However, the medicine identifying apparatus as disclosed in the patent documents 1 and 2 is still at an investigation stage, thus the medicine identifying apparatus has not been yet put into a practical use. For completing the medicine identifying apparatus as a really-usable product, there has been required that a plurality of developments for a variety of aspects of a medicine identifying system such as an apparatus, software and the like.

Further, there is a case where a medicine dispensed by a drug shop is inspected. In this inspection, it is checked whether or not the dispensed medicine matches a prescription. In this regard, an apparatus for performing this inspection has been also developed. However, in the inspection, it is only necessary to determine whether or not the dispensed medicine is correct based on the prescription unlike the identification. Thus, there is no need to search candidate medicines from a large number of medicines. Therefore, a technic for the inspection cannot be simply applied to the identification.

It is an objection of the present invention to contribute to practical realization of the medicine identifying system.

SUMMARY OF THE INVENTION

First Aspect of the Present Invention

A first aspect of the present invention relates to a medicine photographing device for photographing an image of a medicine. The medicine photographing device includes a placing part, a first camera, a second camera, a first light source, a second light source, a third light source and a fourth light source. The medicine is to be set on the placing part. The first camera is provided on an upper side of the placing part. The second camera is provided on a lower side of the placing part. The first light source is provided on the upper side of the placing part. The second light source is constituted of the same kind of light source as the first light source and provided on the lower side of the placing part. The third light source is constituted of a different kind of light source differing from the first light source and provided on the upper side of the placing part. The fourth light source is constituted of the same kind of light source as the third light source and provided on the lower side of the placing part.

It is preferable that each of the first camera and the second camera can photograph a color image. The first light source and/or the second light source are preferably used for photographing an engraved mark of the medicine. The third light source and/or the fourth light source are preferably used for photographing a print of the medicine.

Each of the first light source and the second light source is preferably a direct light source, and more preferably a ring lighting part. In the case where the first light source is constituted of the ring lighting part, this ring lighting part is referred to as a first ring lighting part. In the case where a placing item for holding the medicine is set on the placing part, this first ring lighting part is preferably provided at a position which is higher than a bottom portion of the placing item and lower than an upper end of the placing item. It is preferable that the placing item includes a petri dish having a transparent bottom portion. Further, it is preferable that the petri dish is inserted into a ring of the first ring lighting part when the petri dish is set on the placing part. At this time, it is preferable that a bottom surface of the petri dish is positioned on the lower side of the first ring lighting part. On the other hand, it is preferable that an upper surface of the placing item is positioned on the upper side of the first ring lighting part.

It is preferable that when the placing part is viewed from the upper side, a photographing area of the first camera contains an inside of the ring of the first ring lighting part. In the same manner, in the case where the second light source is constituted of a second ring lighting part, it is preferable that when the placing part is viewed from the lower side, a photographing area of the second camera contains an inside of a ring of the second ring lighting part. Further, it is preferable that light from the third light source passes through the inside of the ring of the first ring lighting part and then reaches to the medicine. In the same manner, it is preferable that light from the fourth light source passes through the inside of the ring of the second ring lighting part and then reaches to the medicine.

It is preferable that a distance from each of the third light source and the fourth light source to the placing part is larger than a distance from each of the first light source and the second light source to the placing part. Further, it is preferable that the third light source is provided at a position which is lower than the first camera and lateral to the placing part. It is preferable that the fourth light source is provided at a position which is higher than the second camera and lateral to the placing part. It is preferable that each of the third light source and the fourth light source is a diffused light source. More specifically, it is preferable that each of the third light source and the fourth light source includes a polarizing filter and is configured so that light passing through the polarizing filter reaches to the medicine. Further, it is preferable that each of the third light source and the fourth light source is constituted of a plurality of bar lighting parts. In this case, it is preferable that at least one of the bar lighting parts is provided so as to be parallel to a front-back direction of the medicine photographing device.

It is preferable that the placing part, the first camera, the second camera, the first light source, the second light source, the third light source and the fourth light source are contained in a case. Further, it is preferable that at least a part of a front surface of the case can be opened and closed at a position higher than the placing part. It is preferable that an inclined portion is formed on the front surface of the case at a position higher than the placing part and a distance between the inclined portion and a rear surface of the medicine photographing device decreases from the lower side to the upper side.

It is preferable that the medicine photographing device includes an inclined surface on the front side of the first camera. It is preferable that this inclined surface extends in the left-right direction of the medicine photographing device and a distance between a horizontal position of its lower end and the rear surface of the medicine photographing device is smaller than a distance between a horizontal position of its upper end and the rear surface of the medicine photographing device.

An inner space of the medicine photographing device exists in the case. Positions higher than the placing part in the inner space are referred to as an internal upper space. It is preferable that the medicine photographing device includes an inclined surface facing this internal upper space in the vicinity of the placing part. This inclined surface extends in the front-back direction of the medicine photographing device and a distance between a horizontal position of its lower end and the placing part is smaller than a distance between a horizontal position of its upper end and the placing part. Further, it is preferable that when the medicine photographing device is viewed from the front side, the inclined surface is positioned on the right side or the left side of the placing part.

It is preferable that the inner space of the medicine photographing device is communicated with outer spaces on a front direction and a left-right direction of the medicine photographing device at a position which is lower than the first camera and higher than the second camera. The inner space is preferably communicated with the outer spaces in the vicinity of the placing part, and more preferably communicated between the first light source and the second light source.

A placing item for setting the medicine in the apparatus is placed on the placing part of the medicine photographing device. It is preferable that the placing item has a configuration in which a petri dish is attached to a tray. It is preferable that a central portion of a bottom surface of this petri dish is transparent and a marginal portion of the bottom surface is non-transparent. Further, a non-transparent member having an upper surface and a concave portion formed on the upper surface is provided in the petri dish as needed.

A Second Aspect of the Present Invention

A second aspect of the present invention relates to medicine identifying software for allowing a computer to identify a medicine. The medicine identifying software includes a step of allowing a first portion of a display device of the computer to display an image obtained by photographing an area containing medicines (a first step). Further, the medicine identifying software includes a step of allowing a second portion of the display device to display an enlarged image of a medicine selected from the medicines shown in the area (a second step). Further, the medicine identifying software includes a step of allowing a third portion of the display device to display information on candidate medicines for the selected medicine based on an identification result for the selected medicine (a third step). Further, the medicine identifying software includes a step of allowing a fourth portion of the display device to display information on a medicine selected by a user from the information on the candidate medicines (a forth step).

The selection to the medicine in the second step may be performed by the user or automatically performed by the computer. For example, when the user selects one of the medicines displayed on the first portion, this selected medicine is displayed on the second portion. Then, in the case where the identification for the selected medicine has been completed, the computer allows the third portion of the display device to display the information on the candidate medicines for the selected medicine. In another aspect, the computer automatically selects one of the medicines whose identification has been completed by the computer from the medicines displayed on the first portion. The enlarged image of this selected medicine is displayed on the second portion of the display device.

In such a process, it is preferable that the computer attaches a first mark, which indicates that the identification for the medicine has been completed, to the medicine whose identification has been completed among the medicines displayed on the first portion. Further, it is preferable that a second mark, which indicates that this medicine is displayed on the second portion, is attached to one of the medicines displayed on the first portion corresponding to the selected medicine displayed on the second portion. Further, it is preferable that a third mark, which indicates that the selection to this medicine has been completed by the user, is attached to one of the medicines displayed on the first portion corresponding to the medicine displayed on the fourth portion. In this regard, it is preferable that color of the first mark is different from color of the third mark.

Examples of the information on the candidate medicines displayed on the third portion include a name of each of the candidate medicines, an image of each of the candidate medicines stored in a database, a numerical value or a rank indicating a degree of possible correctness of each of the candidate medicines, an engraved mark or a printed code on each of the candidate medicines and a code for identifying each of the candidate medicines. It is preferable that information on one medicine is displayed in one line.

In one aspect of such a medicine identifying process, arbitrary medicines of the medicines displayed on the first portion are grouped. Specifically, the computer allows the user to select arbitrary medicines from the medicines displayed on the first portion. Next, the computer groups these selected medicines as one group. Then, in the case where medicines whose identification has been completed and medicines whose identification has not been completed concurrently exist in the group, the identification for the un-identified medicines is omitted. Further, in the case where the user selects the information on one of the medicines grouped at the fourth step, this selection result is reflected to the other medicines belonging to the same group.

A Third Aspect of the Present Invention

A third aspect of the present invention relates to medicine identifying software for allowing a computer to identify a medicine. The computer including this medicine identifying software first obtains an image in which medicines are shown (a first step). Next, the computer separates areas in which the medicines exist from the obtained image (a second step). Next, the computer extracts engraved marks and/or prints in the separated areas (a third step). Next, the computer searches the medicines based on the extracted engraved marks and/or the extracted prints (a fourth step).

At the first step, it is preferable that the computer obtains a color image obtained by photographing the medicines from the upper side and a color image obtained by photographing the medicines from the lower side. After the second step has been performed, it is preferable that the computer associates an area in which each of the medicines exists and which is separated from the image photographed from the upper side with an area in which each of the medicines exists and which is separated from the image photographed from the lower side. This associating can be performed by, for example, inverting one of the image photographed from the upper side and the image photographed from the lower side and then overlapping the inverted image with the non-inverted image.

After the second step has been performed, the computer may determine whether or not each of the separated medicines is a tablet. This determination can be performed by, for example, comparing the image obtained by photographing the medicines from the upper side with the image obtained by photographing the medicines from the lower side. More specifically, in the case where the described associating for the areas in which each of the medicines exists is successfully performed, the computer can determine that each of the medicines is the tablet.

For extracting the engraved marks of the medicines from the image in which the medicines are shown at the third step, it is preferable to use an image obtained by photographing the medicines in a state that the medicines are illuminated with direct light. Further, for extracting the prints of the medicines from the image in which the medicines are shown at the third step, it is preferable to use an image obtained by photographing the medicines in a state that the medicines are illuminated with diffused light.

After the second step has been performed, before the third step is formed, while the third step is being performed or after the third step has been performed, the computer may detect whether or not the engraved marks and/or the prints are attached to the medicines. At the fourth step, the computer may narrow a range of medicines to be searched based on the presence/absence of the detected engraved marks and/or the detected prints. Further, after the second step has been performed, the computer may determine whether or not each of the medicines has a secant line. At the fourth step, the computer may narrow the range of the medicines to be searched based on the determining result for the presence/absence of the secant line. Further, the computer may extract representative color of the medicines before the fourth step is performed.

When the fourth step is performed, the computer may narrow the range of the medicines to be searched based on information obtained from the photographed image of the medicine. Examples of such information includes a type of each of the medicines, a shape of each of the medicines, a size of each of the medicines, the presence/absence of the engraved mark on each of the medicines, the presence/absence of the print on each of the medicines, the presence/absence of the secant line on each of the medicines and color of each of the medicines.

At the fourth step, it is preferable to search the medicines by subjecting image data of the engraved marks and/or the prints obtained at the third step to a pattern matching process using template image data stored in the database. In this pattern matching process, it is preferable to calculate a score indicating a matching rate between the image data obtained at the third step and the template image data. Prior to the pattern matching process, the obtained image data and/or the template image data may be subjected to a position adjusting process. Further, prior to the pattern matching process, the obtained image data and/or the template image data may be rotated. Further, the pattern matching process may be performed on an entire of the image data of the engraved marks and/or the prints obtained at the third step or only a part of the obtained image data.

Fourth Aspect of the Present Invention

Aspect (1): Medicine identifying software for allowing a computer to identify a medicine, wherein the medicine identifying software is capable of allowing the computer to:

allow a first portion of a display device of the computer to display an image obtained by photographing an area containing medicines;

allow a second portion of the display device to display an enlarged image of a medicine selected from the medicines shown in the area; and allow a third portion of the display device to display information on candidate medicines for the selected medicine based on an identification result for the selected medicine.

Aspect (2): The medicine identifying software according to the aspect (1), wherein the medicine identifying software is capable of further allowing the computer to allow a fourth portion of the display device to display information on the medicine selected from the information on the candidate medicines.

Aspect (3): The medicine identifying software according to the aspect (1) or (2), wherein the medicine identifying software is capable of further allowing the computer to attach a first mark, which indicates that the identification for the medicine has been completed, to the medicine whose identification has been completed among the medicines displayed on the first portion.

Aspect (4): The medicine identifying software according to any one of the aspects (1) to (3), wherein the medicine identifying software is capable of further allowing the computer to:

allow the second portion to display the medicine selected from the medicines displayed on the first portion by a user; and allow the third portion of the display device to display the information on the candidate medicines for the selected medicine when the identification for the selected medicine has been completed.

Aspect (5): The medicine identifying software according to any one of the aspects (1) to (3), wherein the medicine identifying software is capable of further allowing the computer to:

automatically select one of the medicines whose identification has been completed from the medicines displayed on the first portion; and allow the second portion of the display device to display the enlarged image of the selected medicine.

Aspect (6): The medicine identifying software according to the aspect (4) or (5), wherein the medicine identifying software is capable of further allowing the computer to attach a second mark, which indicates that this medicine is displayed on the second portion, to one of the medicines displayed on the first portion corresponding to the selected medicine displayed on the second portion.

Aspect (7): The medicine identifying software according to any one of the aspects (1) to (6), wherein the medicine identifying software is capable of further allowing the computer to:

allow the forth portion of the display device to display the information on the medicine selected by the user among the information on the candidate medicines; and attach a third mark, which indicates that the selection to this medicine has been completed by the user, to one of the medicines displayed on the first portion corresponding to the medicine displayed on the fourth portion.

Aspect (8): The medicine identifying software according to any one of the aspects (1) to (7), wherein the medicine identifying software is capable of further allowing the computer to:

attach a first mark, which indicates that the identification for the medicine has been completed, to the medicine whose identification has been completed among the medicines displayed on the first portion;

allow a fourth portion of the display device to display information on the medicine selected from the information on the candidate medicines by a user; and attach a third mark, which indicates that the selection to this medicine has been completed by the user, to one of the medicines displayed on the first portion corresponding to the medicine displayed on the fourth portion, and wherein color of the first mark, which indicates that the identification for the medicine has been completed, is different from color of the third mark, which indicates that the selection to this medicine has been completed by the user.

Aspect (9): The medicine identifying software according to any one of the aspects (1) to (8), wherein the medicine identifying software is capable of further allowing the computer to:

allow the first portion to display an image obtained by photographing the medicines from an upper side and/or an image obtained by photographing the medicines from a lower side; and allow the second portion to display an image obtained by photographing the selected medicine from the upper side and/or an image obtained by photographing the selected medicine from the lower side.

Aspect (10): The medicine identifying software according to any one of the aspects (1) to (9), wherein the medicine identifying software is capable of further allowing the computer to allow the third portion to display a name of each of the candidate medicines, an image of each of the candidate medicines stored in a database, a numerical value or a rank indicating a degree of possible correctness of each of the candidate medicines and an engraved mark or a printed code on each of the candidate medicines as the information on the candidate medicines.

Aspect (11): The medicine identifying software according to the aspect (10), wherein the name of each of the candidate medicines, the image of each of the candidate medicines stored in the database, the numerical value or the rank indicating the degree of possible correctness of each of the candidate medicines and the engraved mark or the printed code on each of the candidate medicines are displayed in one line.

Aspect (12): The medicine identifying software according to the aspect (10) or (11), wherein one of the images of the medicines displayed on the third portion is enlarged according to operation from the user.

Aspect (13): The medicine identifying software according to any one of the aspects (1) to (12), wherein the medicine identifying software is capable of further allowing the computer to group arbitrary medicines of the medicines displayed on the first portion.

Aspect (14): The medicine identifying software according to the aspect (13), wherein the medicine identifying software is capable of further allowing the computer to allow the user to select the arbitrary medicines from the medicines displayed on the first portion and group these selected medicines as one group.

Aspect (15): The medicine identifying software according to the aspect (13) or (14), wherein when medicines whose identification has been completed and medicines whose identification has not been completed concurrently exist in the group, the identification for the medicines whose identification has not been completed is omitted.

Fifth Aspect of the Present Invention

Aspect (16): Medicine identifying software for allowing a computer to identify a medicine, wherein the medicine identifying software is capable of allowing the computer to:

obtain an image in which a medicine to be identified is shown;

extract an area occupied by the medicine from the image;

extract an engraved mark and/or a print in the area; and search the medicine based on the extracted engraved mark and/or the extracted print.

Aspect (17): The medicine identifying software according to the aspect (16), wherein when the medicine identifying software allows the computer to obtain the image in which the medicine to be identified is shown, the medicine identifying software is capable of allowing the computer to:

obtain an image obtained by photographing the medicine from an upper side and an image obtained by photographing the medicine from a lower side to extract areas occupied by the medicine from the images; and associate the area which is occupied by the medicine and separated from the image obtained by photographing the medicine from the upper side with the area which is occupied by the medicine and separated from the image obtained by photographing the medicine from the lower side.

Aspect (18): The medicine identifying software according to the aspect (17), wherein the medicine identifying software is capable of further allowing the computer to invert one of the image obtained by photographing the medicine from the upper side and the image obtained by photographing the medicine from the lower side and then overlap the inverted image with the other one of the image obtained by photographing the medicines from the upper side and the image obtained by photographing the medicines from the lower side to associate the area in which the medicine which is occupied by the medicine and separated from the image obtained by photographing the medicine from the upper side with the area in which the medicine which is occupied by the medicine and separated from the image obtained by photographing the medicine from the lower side.

Aspect (19): The medicine identifying software according to any one of the aspects (16) to (18), wherein the medicine identifying software is capable of further allowing the computer to determine whether or not the medicine is a tablet.

Aspect (20): The medicine identifying software according to the aspect (19), wherein when the medicine identifying software allows the computer to determine whether or not the medicine is the tablet, the medicine identifying software is capable of further allowing the computer to:

obtain an image obtained by photographing the medicine from an upper side and an image obtained by photographing the medicine from a lower side; and compare the image obtained by photographing the medicine from the upper side with the image obtained by photographing the medicine from the lower side to determine whether or not the medicine is the tablet.

Aspect (21): The medicine identifying software according to the aspect (20), wherein after the medicine identifying software allows the computer to extract the area occupied by the medicine, the medicine identifying software is capable of further allowing the computer to:

associate an area which is occupied by the medicine and separated from the image obtained by photographing the medicine from the upper side with an area which is occupied by the medicine and separated from the image obtained by photographing the medicine from the lower side; and determine that the medicine is the tablet when this associating is successfully performed.

Aspect (22): The medicine identifying software according to any one of the aspects (16) to (21), wherein when the medicine identifying software allows the computer to obtain the image in which the medicine is shown, the medicine identifying software is capable of allowing the computer to photograph the image of the medicine in a state that the medicine is illuminated with direct light, and when the medicine identifying software allows the computer to extract the engraved mark, the medicine identifying software is capable of allowing the computer to extract the engraved mark based on this photographed image.

Aspect (23): The medicine identifying software according to any one of the aspects (16) to (22), wherein when the medicine identifying software allows the computer to obtain the image in which the medicine is shown, the medicine identifying software is capable of allowing the computer to photograph the image of the medicine in a state that the medicine is illuminated with diffused light, and when the medicine identifying software allows the computer to extract the print, the medicine identifying software is capable of allowing the computer to extract the print based on this photographed image.

Aspect (24): The medicine identifying software according to any one of the aspects (16) to (23), wherein when the medicine identifying software allows the computer to extract the engraved mark and/or the print in the area, the medicine identifying software is capable of allowing the computer to detect whether or not the engraved mark and/or the print is attached to the medicine, and when the medicine identifying software allows the computer to search the medicine, the medicine identifying software is capable of allowing the computer to narrow a range of medicines to be searched based on the presence/absence of the detected engraved mark and/or the detected print.

Aspect (25): The medicine identifying software according to any one of the aspects (16) to (24), wherein after the medicine identifying software allows the computer to extract the area occupied by the medicine, the medicine identifying software is capable of further allowing the computer to determine whether or not the medicine has a secant line, and when the medicine identifying software allows the computer to search the medicine, the medicine identifying software is capable of allowing the computer to narrow a range of medicines to be searched based on a determining result for the presence/absence of the secant line.

Aspect (26): The medicine identifying software according to any one of the aspects (16) to (25), wherein when the medicine identifying software allows the computer to search the medicine, the medicine identifying software is capable of allowing the computer to narrow a range of medicines to be searched based on at least one of a type of the medicine, a shape of the medicine, a size of the medicine, the presence/absence of the engraved mark on the medicine, the presence/absence of the print on the medicine, the presence/absence of a secant line on the medicine and color of the medicine.

Aspect (27): The medicine identifying software according to any one of the aspects (16) to (26), wherein the medicine identifying software allows the computer to search the medicine by subjecting image data of the extracted engraved mark and/or the extracted print to a pattern matching process using template image data stored in a database.

Aspect (28): The medicine identifying software according to the aspect (27), wherein a score indicating a matching rate between the image data of the extracted engraved mark and/or the extracted print and the template image data is calculated in the pattern matching process.

Sixth Aspect of the Present Invention

Aspect (29): A medicine identifying method for identifying a medicine, comprising:

obtaining an image in which a medicine to be identified is shown;

extracting an area occupied by the medicine from the image;

extracting an engraved mark and/or a print in the area; and searching the medicine based on the extracted engraved mark and/or the extracted print.

Seventh Aspect of the Present Invention

Aspect (30): A medicine identifying apparatus for identifying a medicine, comprising:

means for obtaining an image in which a medicine to be identified is shown;

means for extracting an area occupied by the medicine from the image;

means for extracting an engraved mark and/or a print in the area; and means for searching the medicine based on the extracted engraved mark and/or the extracted print.

The present invention makes it possible to automatically identify the medicine. According to the present invention, it would be possible to reduce the burden in the medicine identification operation.

Each of FIGS. 2 to 8 mainly shows a configuration of a medicine photographing device.

Figure 2:
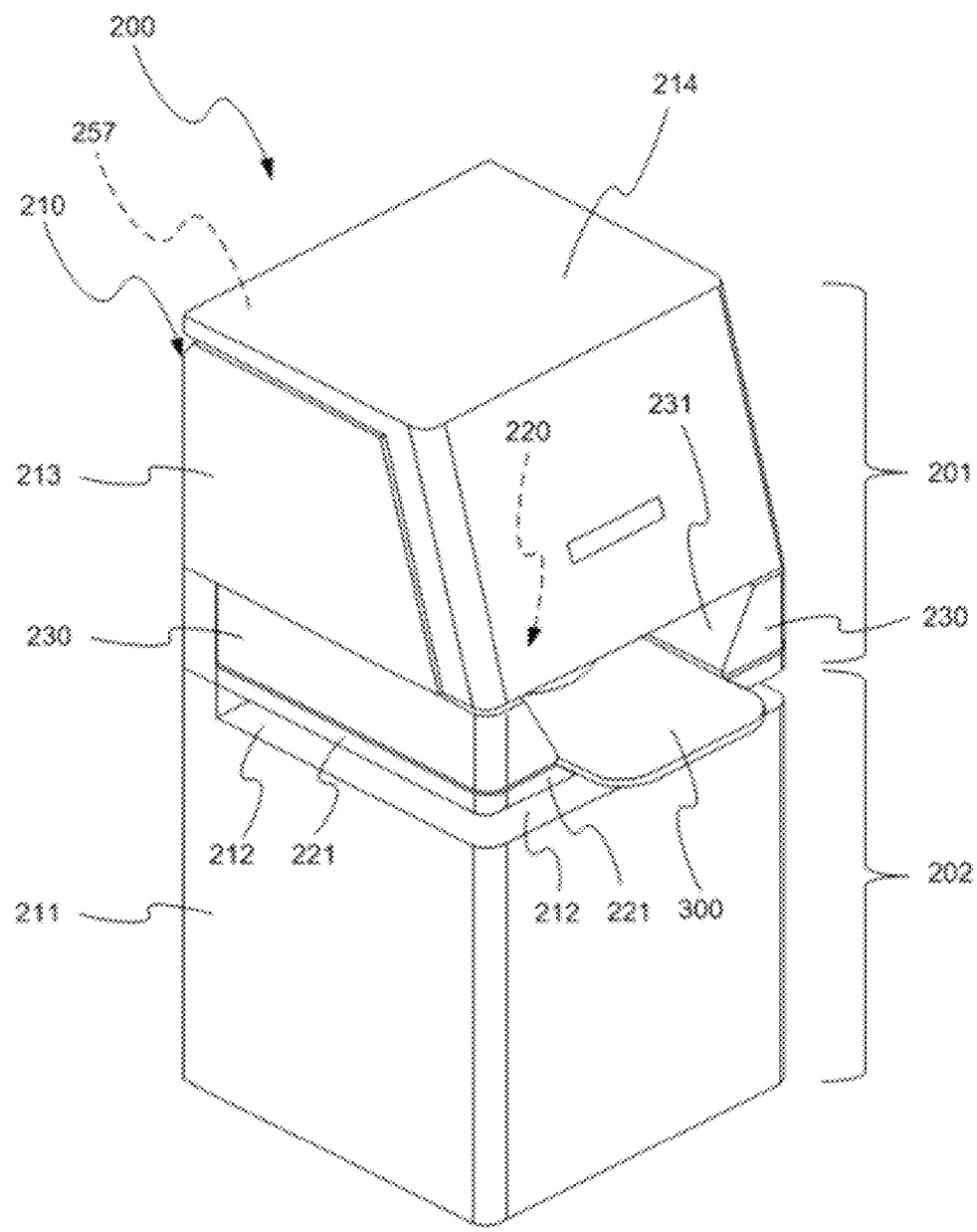

FIG. 2 is a perspective view of an embodiment of the medicine photographing device.

Figure 3:
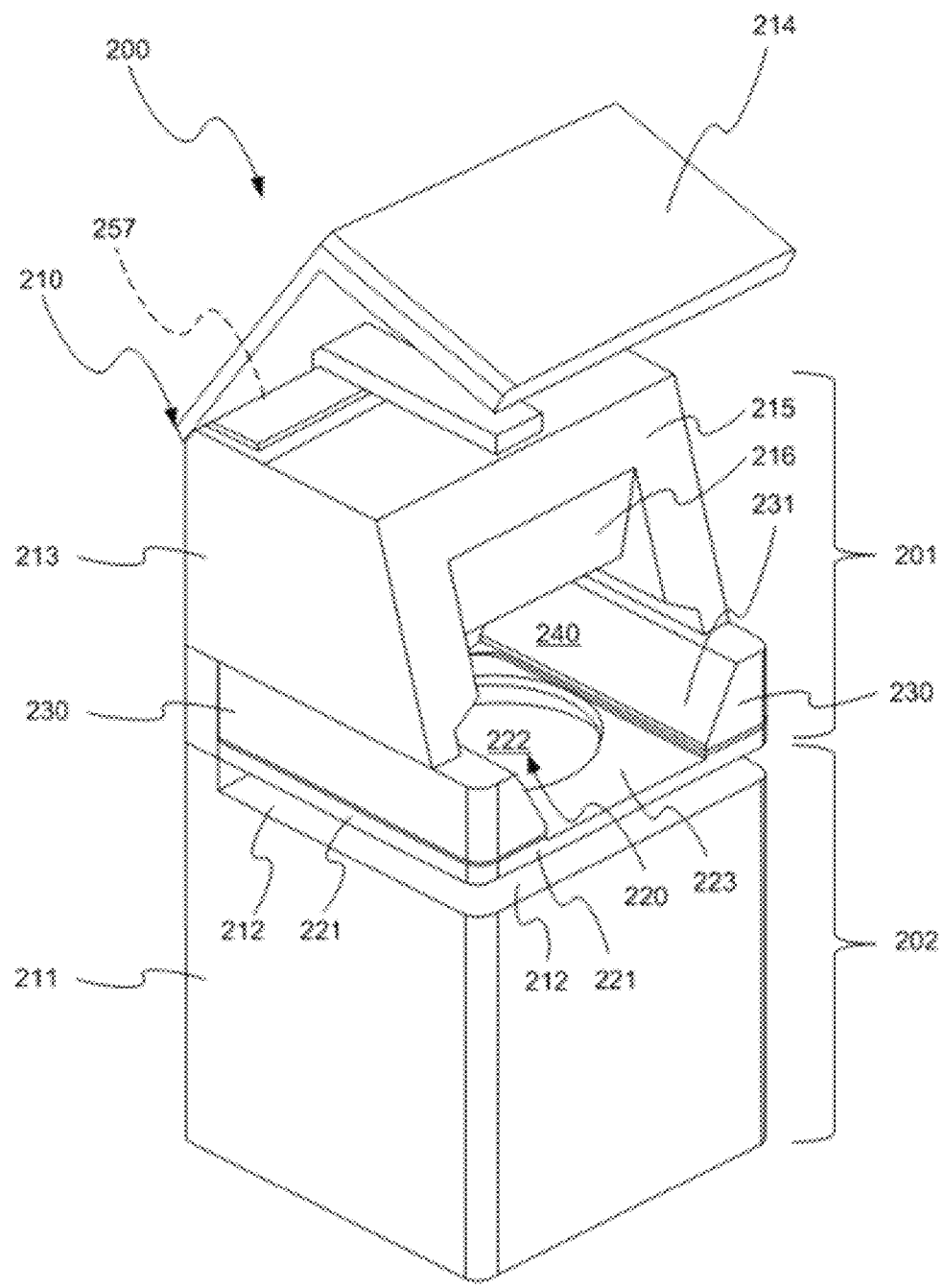

FIG. 3 is a perspective view showing a state that a front cover of the medicine photographing device shown in FIG. 2 is opened.

Figure 4:
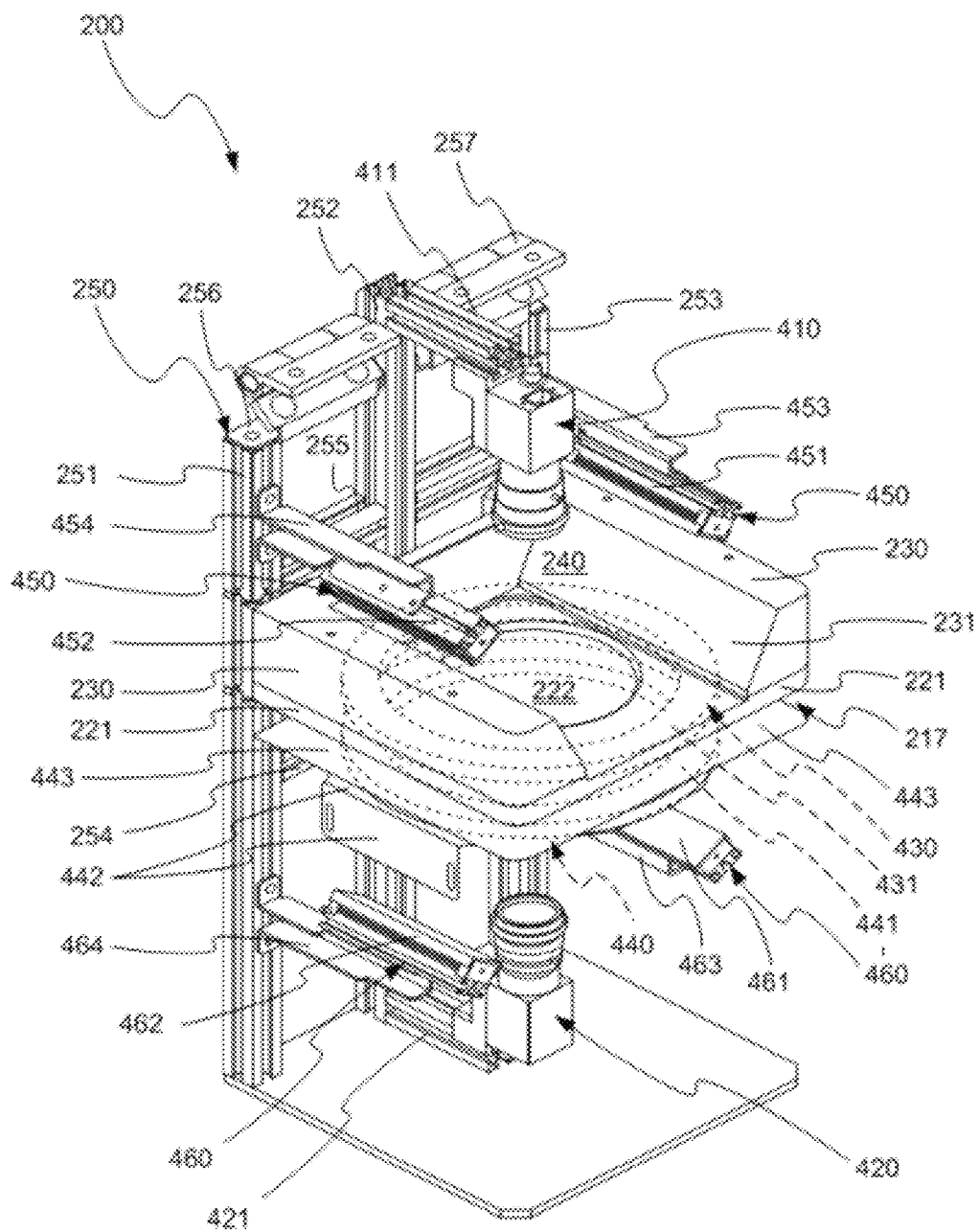

FIG. 4 is a perspective view showing an internal configuration of the medicine photographing device shown in FIG. 2. In this figure, a frame and members attached to the frame are mainly illustrated.

Figure 5:
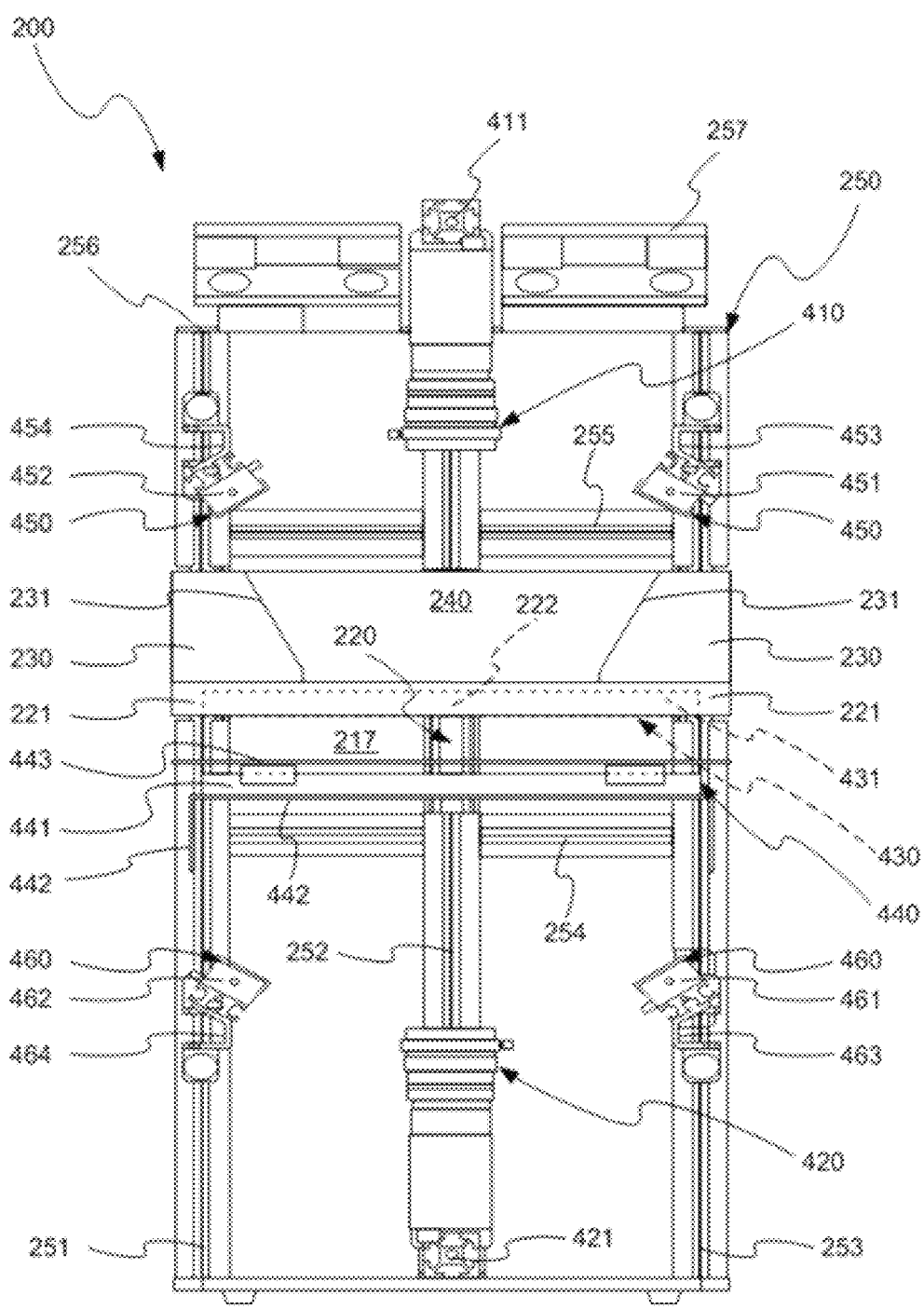
Figure 6:
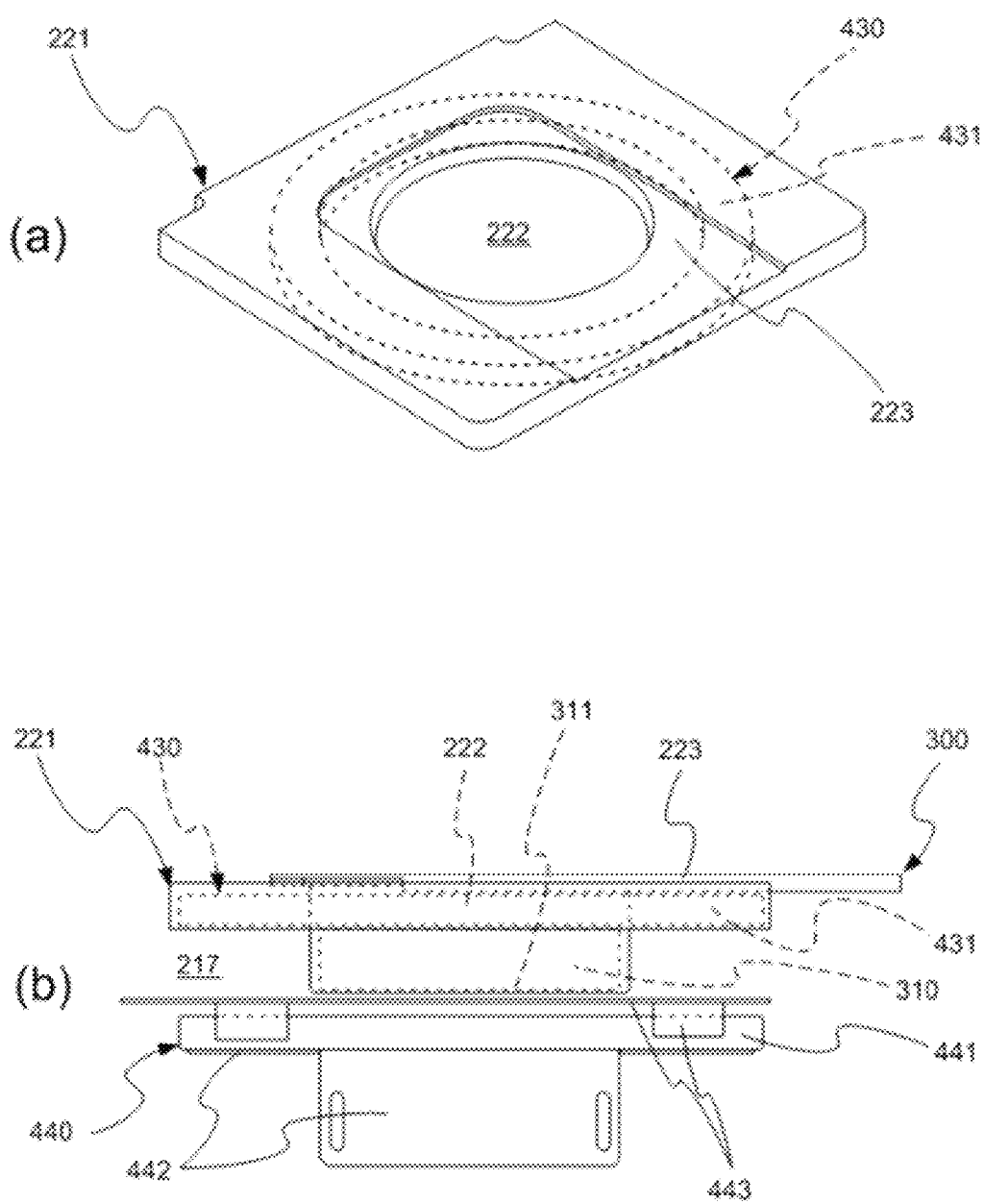
Figure 7:
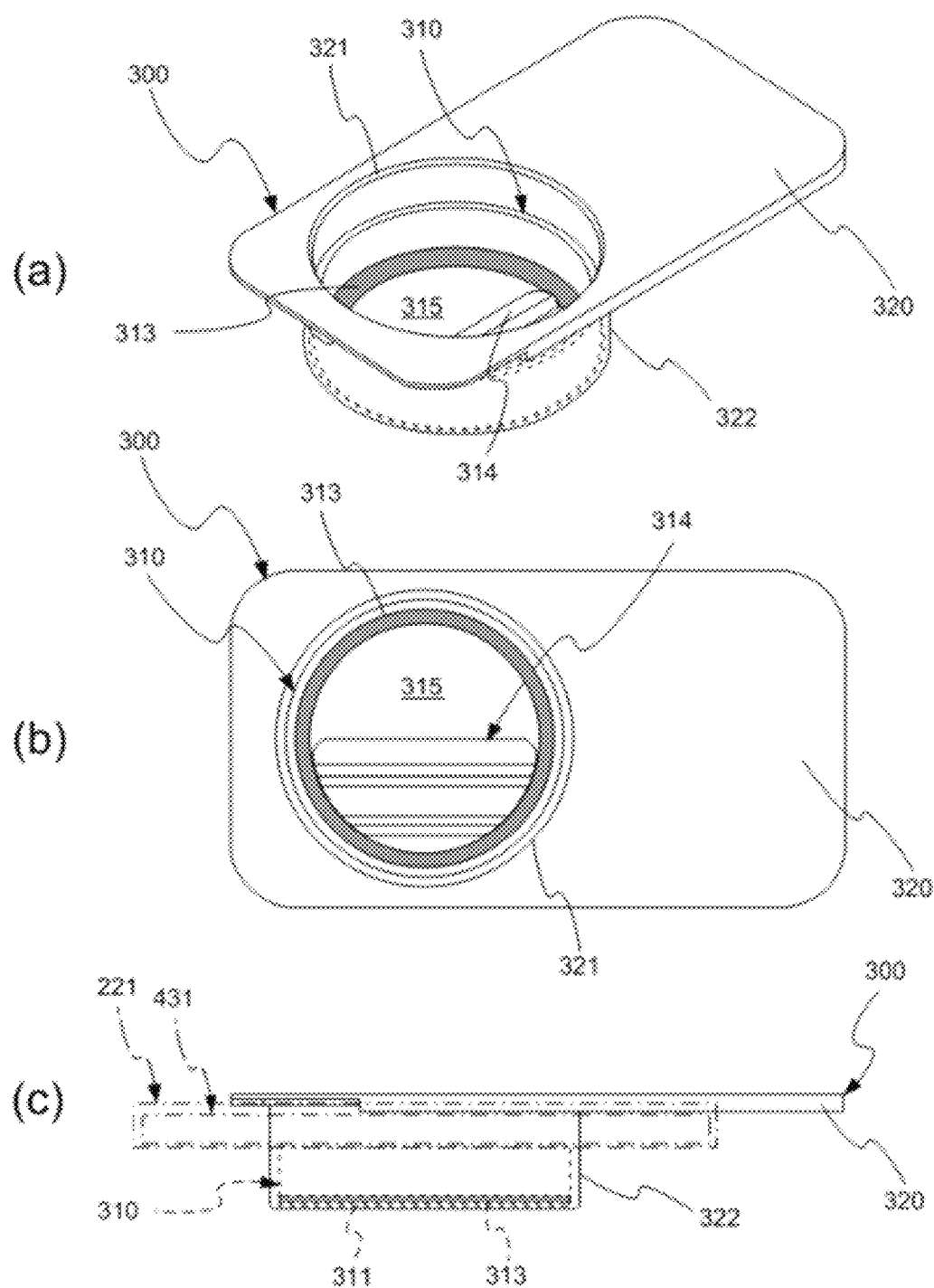

FIG. 5 is a front view of the medicine photographing device shown in FIG. 4.

FIG. 6A is a perspective view showing an entire of a supporting member. FIG. 6B is a perspective view showing a positional relationship among a first light source, a second light source and a medicine placing item.

FIG. 7A is a perspective view showing a first embodiment of a tray to be set in the medicine photographing device. FIG. 7B is a top view of the tray. FIG. 7C is a side view of the tray.

Figure 8:
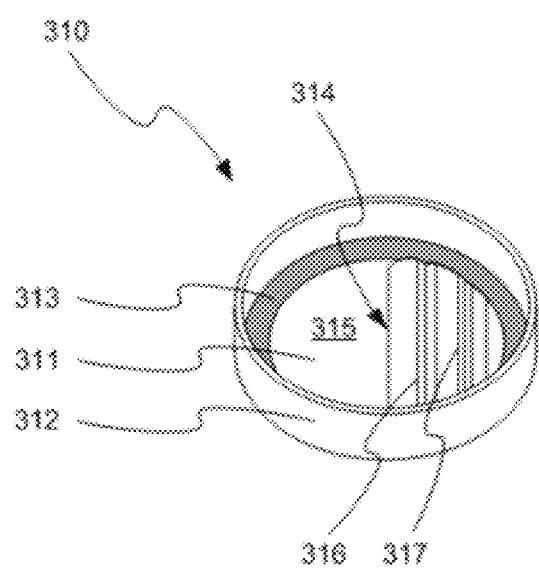

FIG. 8 is a perspective view of a petri dish to be attached to the tray shown in FIG. 7A.

Each of FIGS. 9 to 21 mainly shows a screen layout of a computer image created by medicine identifying software.

Figure 9:
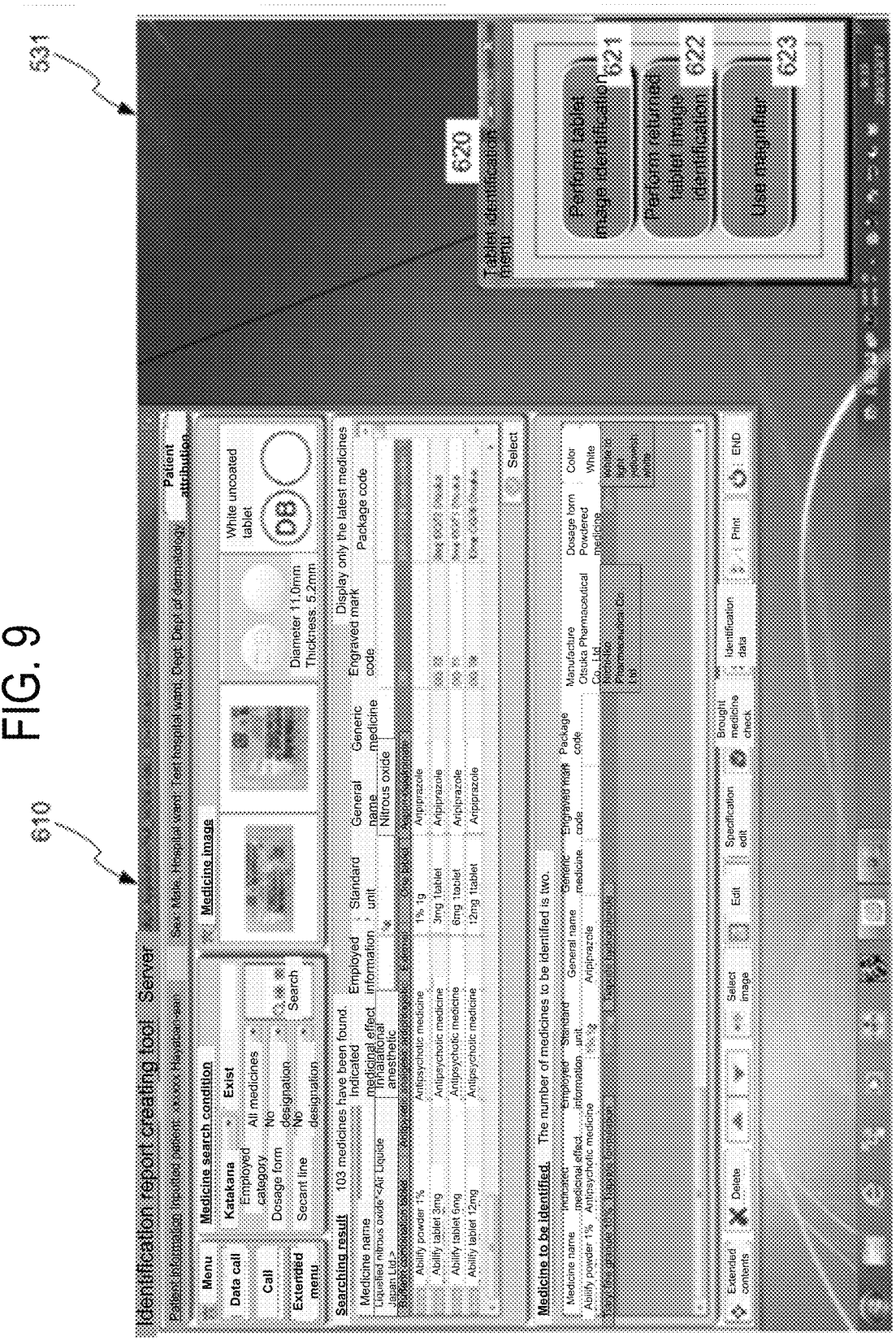

FIG. 9 is a screen image at an initial stage after the medicine identifying software is activated.

Figure 10:
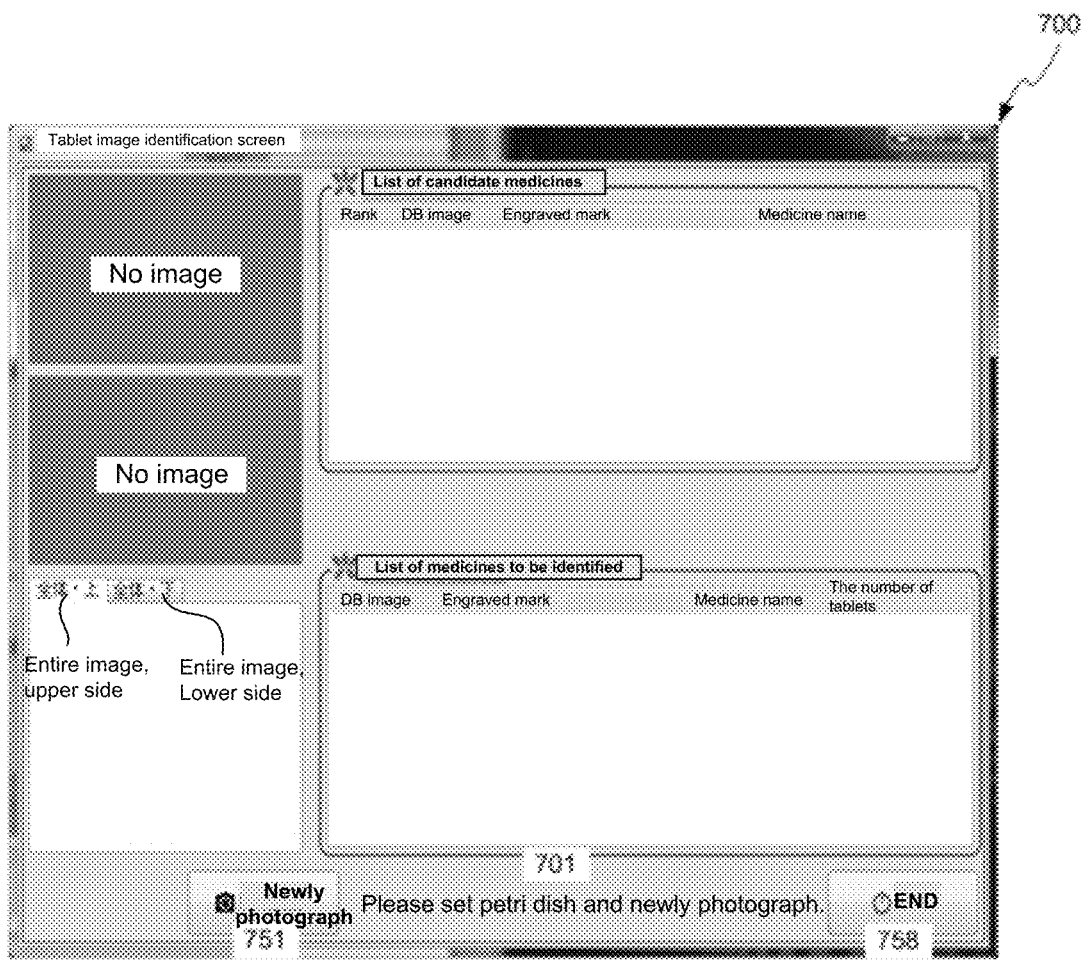

FIG. 10 is a screen image at a first stage for performing medicine image identification.

Figure 11:
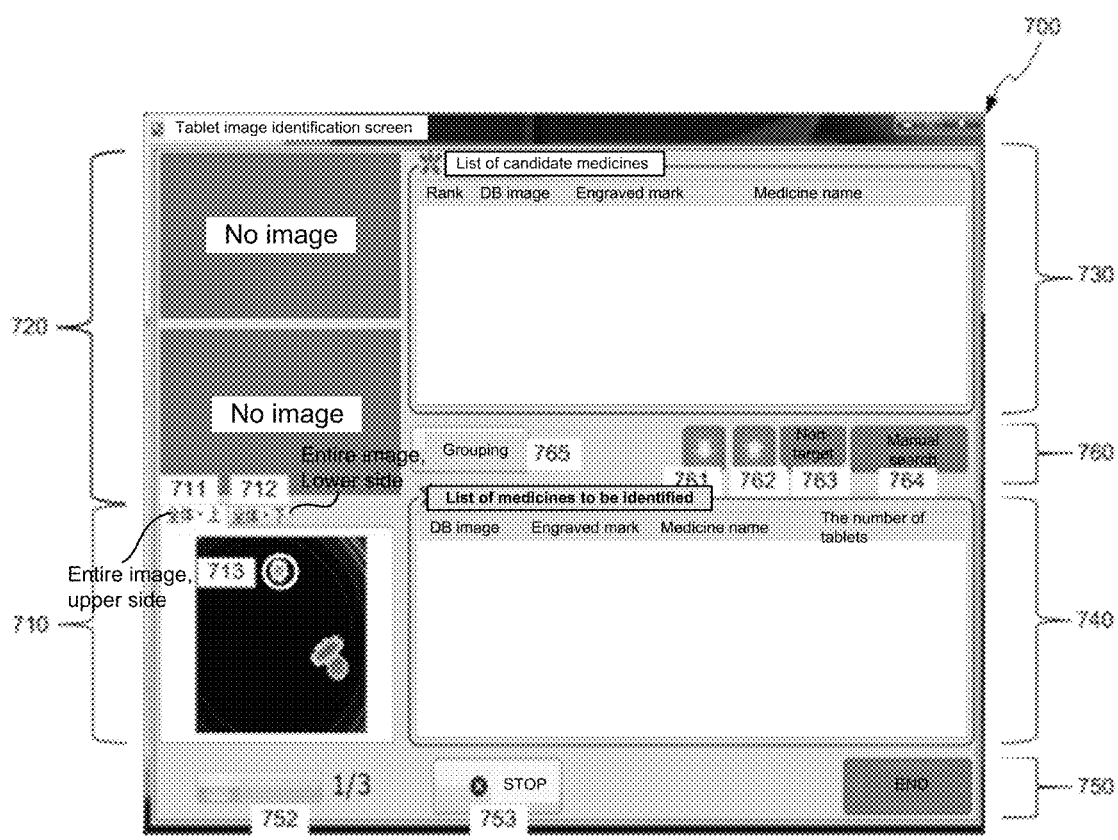

FIG. 11 is a screen image at a second stage for performing the medicine image identification.

Figure 12:
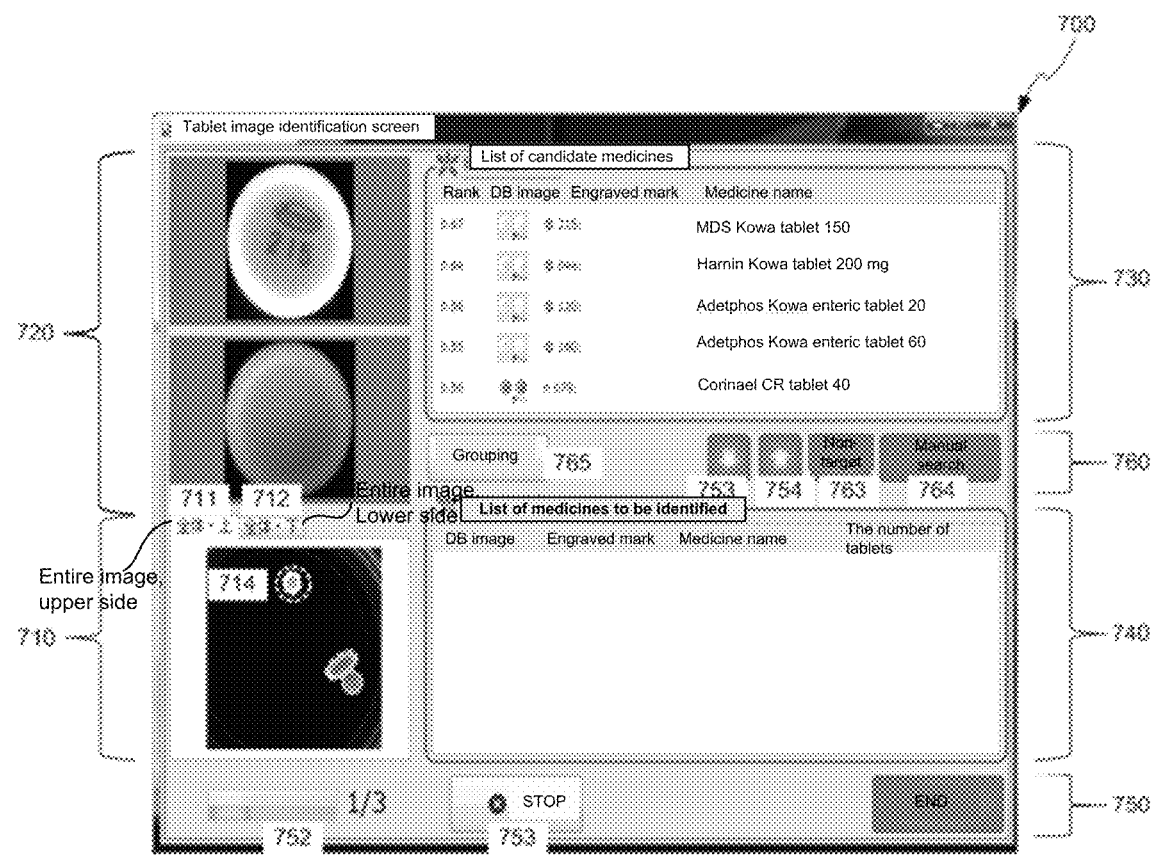

FIG. 12 is a screen image at a third stage for performing the medicine image identification.

Figure 13:
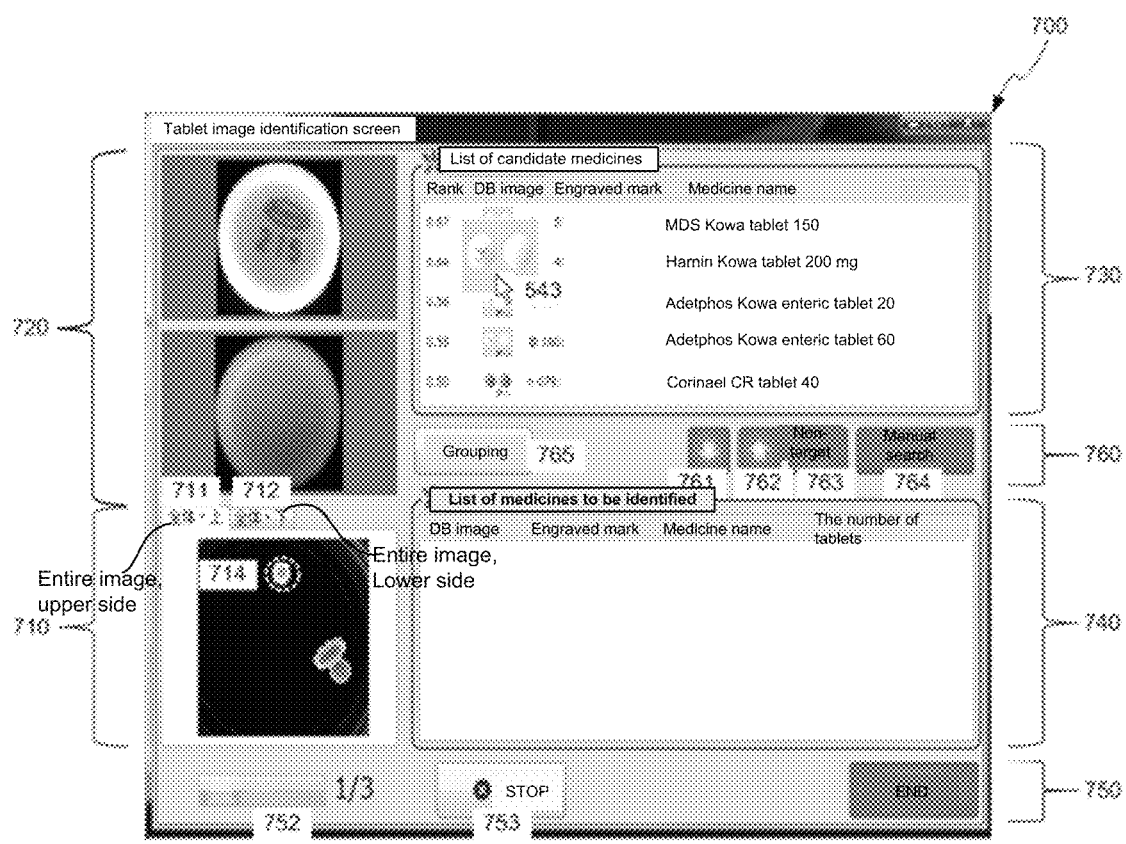

FIG. 13 is a screen image at a fourth stage for performing the medicine image identification.

Figure 14:
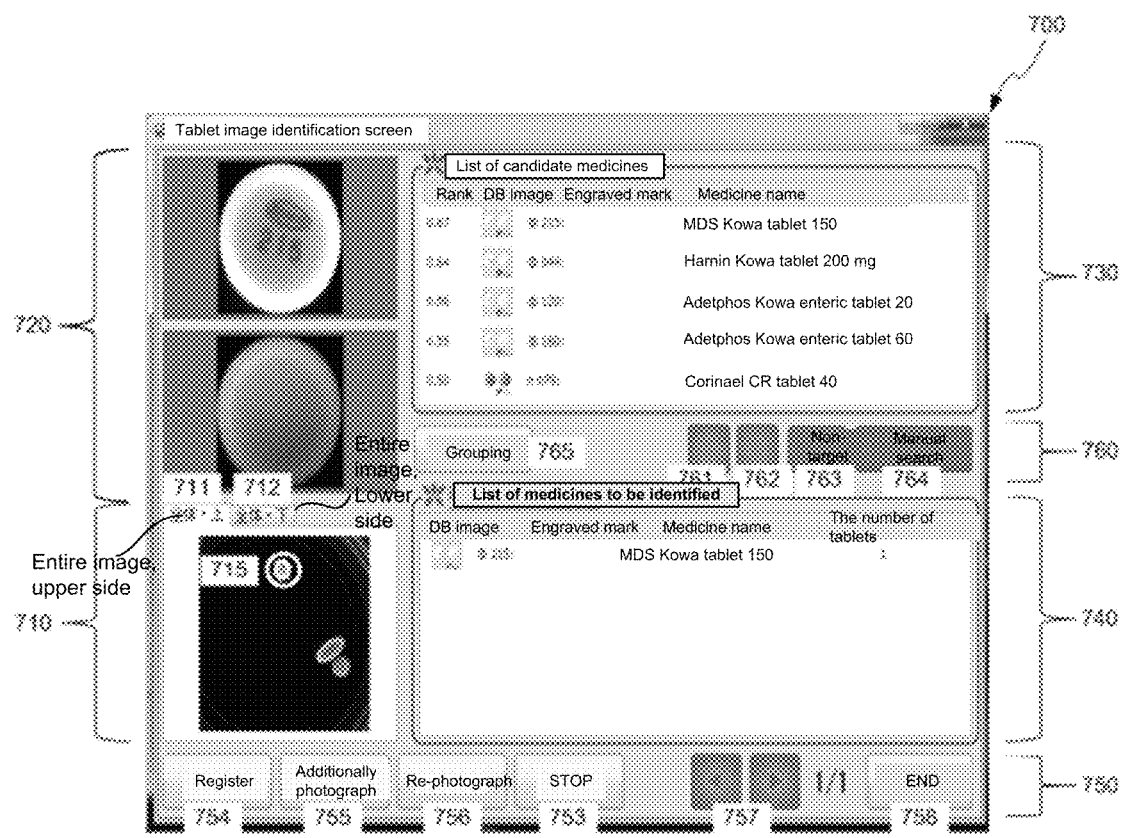

FIG. 14 is a screen image at a fifth stage for performing the medicine image identification.

Figure 15:
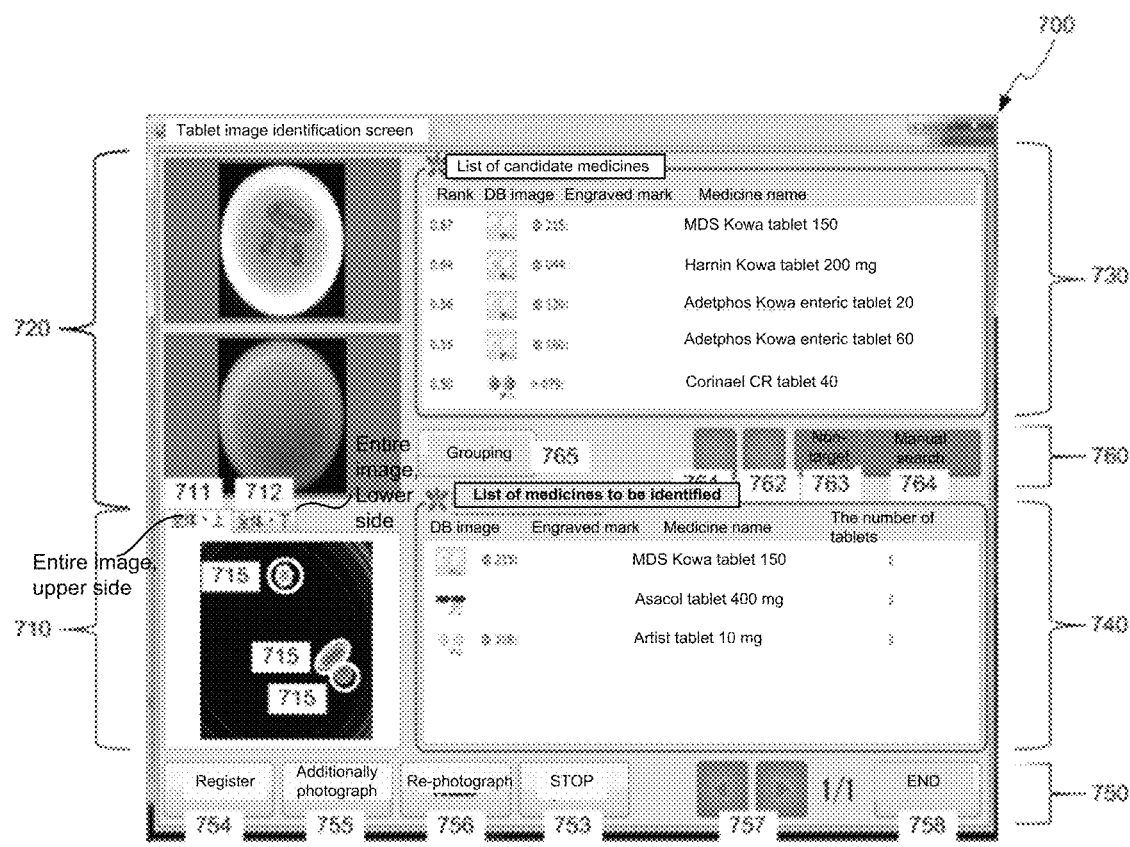

FIG. 15 is a screen image at a sixth stage for performing the medicine image identification.

Figure 16:
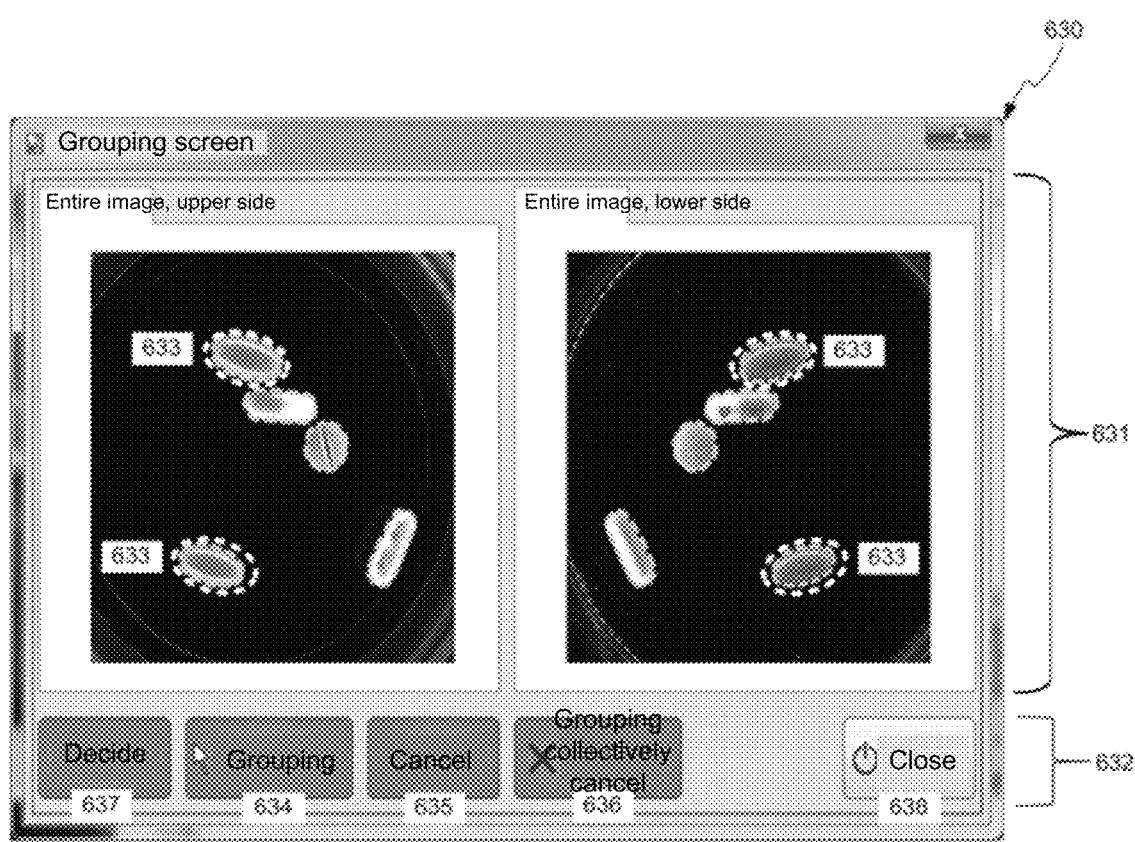

FIG. 16 is a screen image at the time of performing a grouping process in the medicine image identification.

Figure 17:
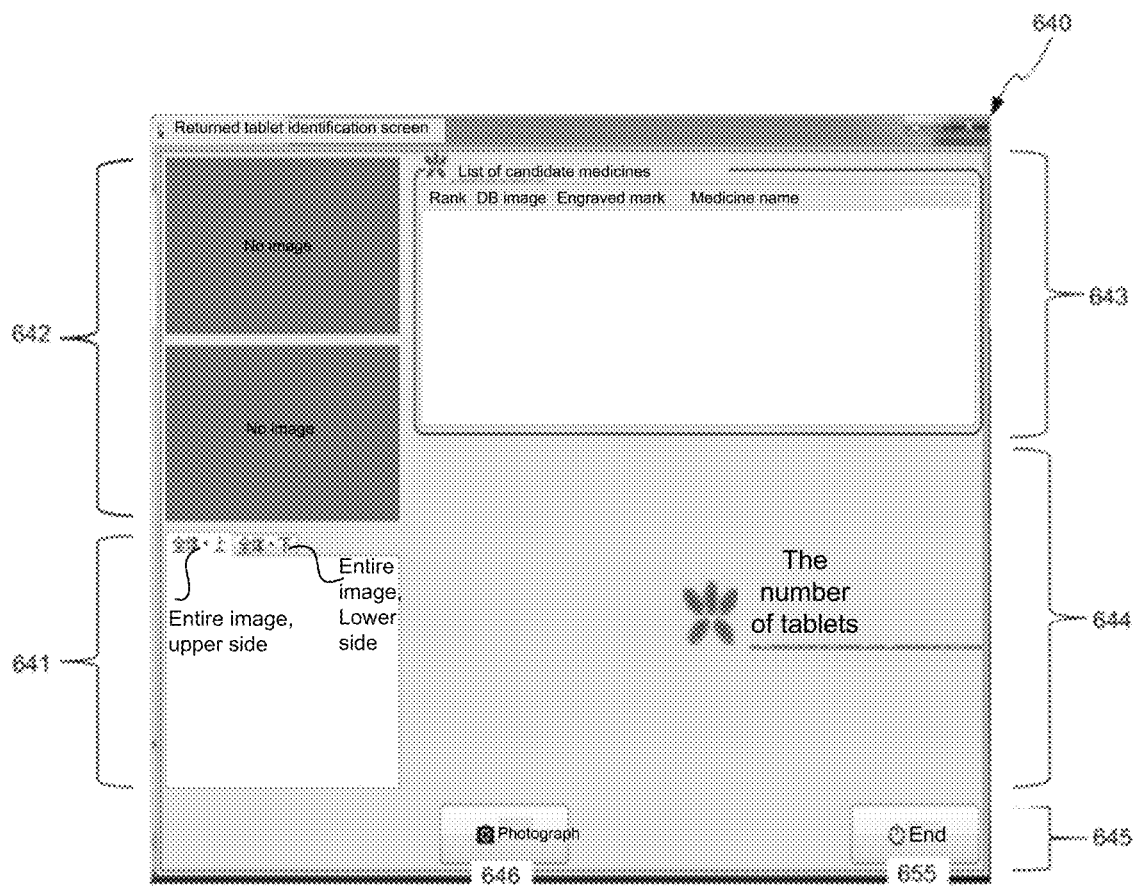

FIG. 17 is a screen image at the first stage of the medicine image identification which is utilized in the case where all of medicines are the same type.

Figure 18:
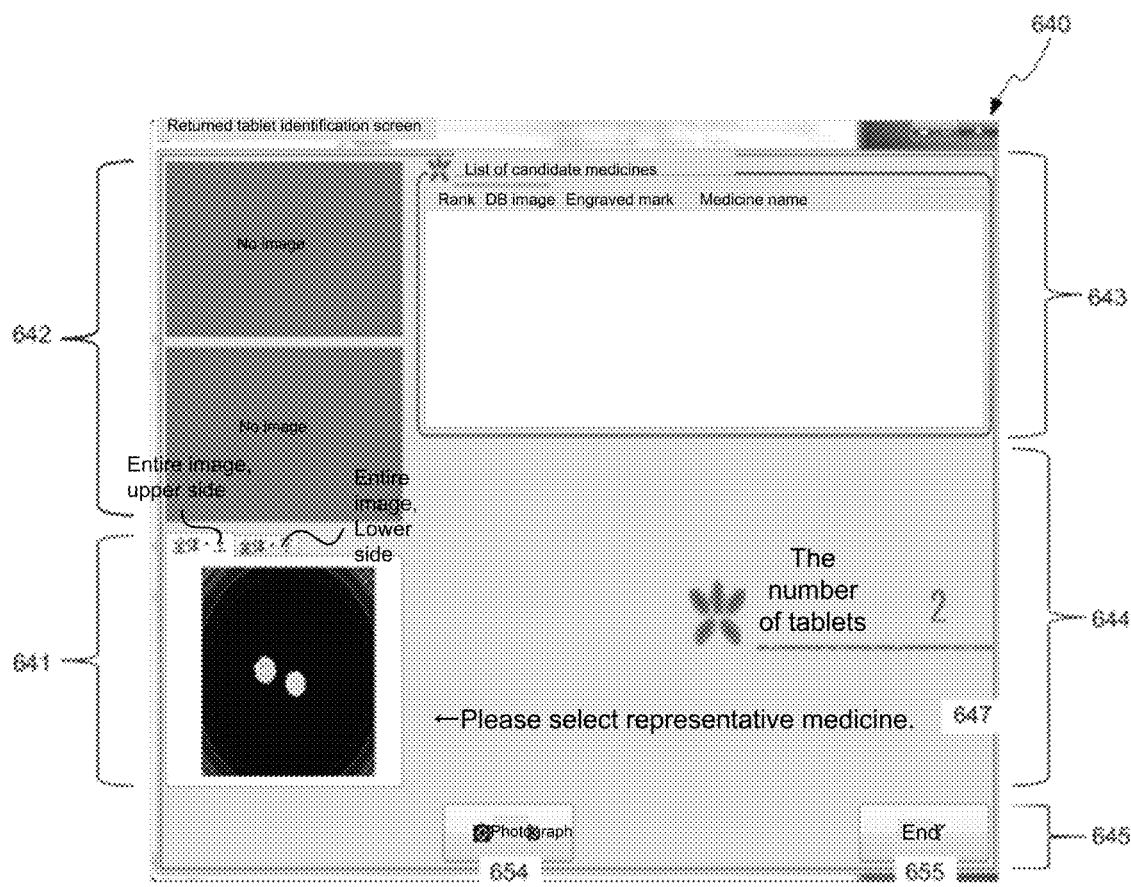

FIG. 18 is a screen image at the second stage of the medicine image identification started at the case shown in FIG. 17.

Figure 19:
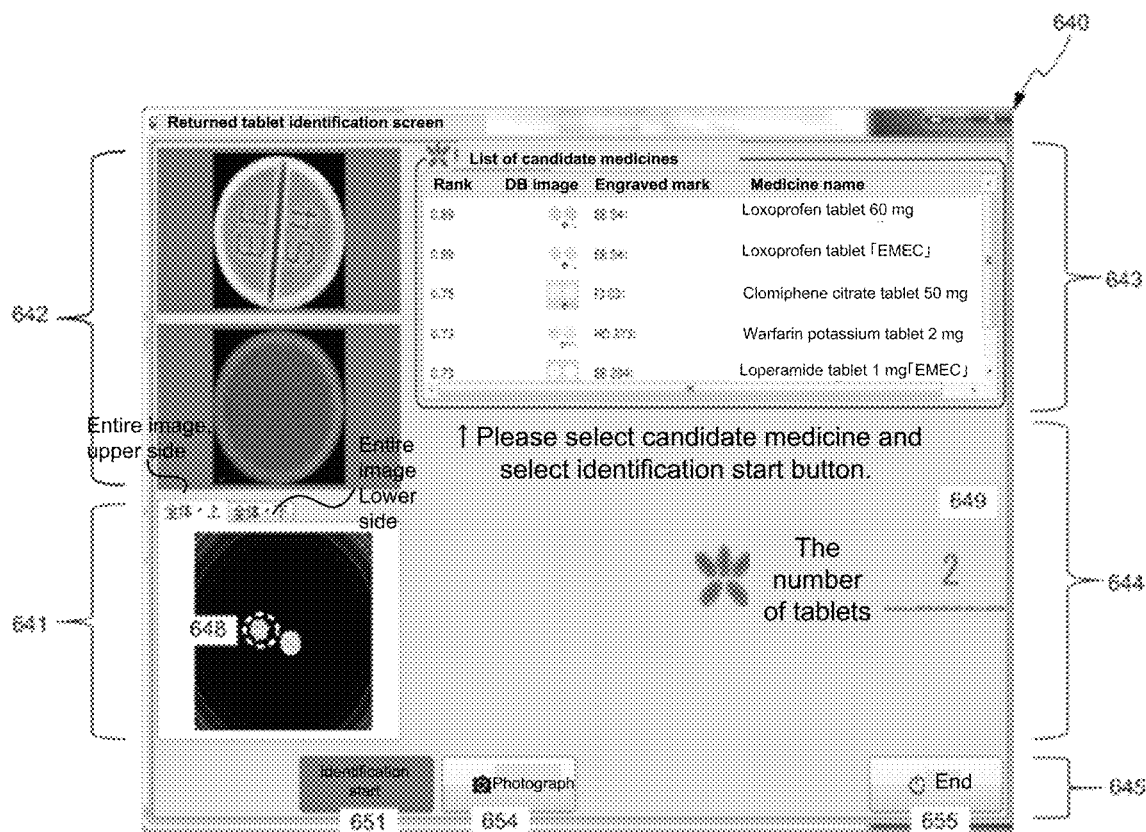

FIG. 19 is a screen image at the third stage of the medicine image identification started at the case shown in FIG. 17.

Figure 20:
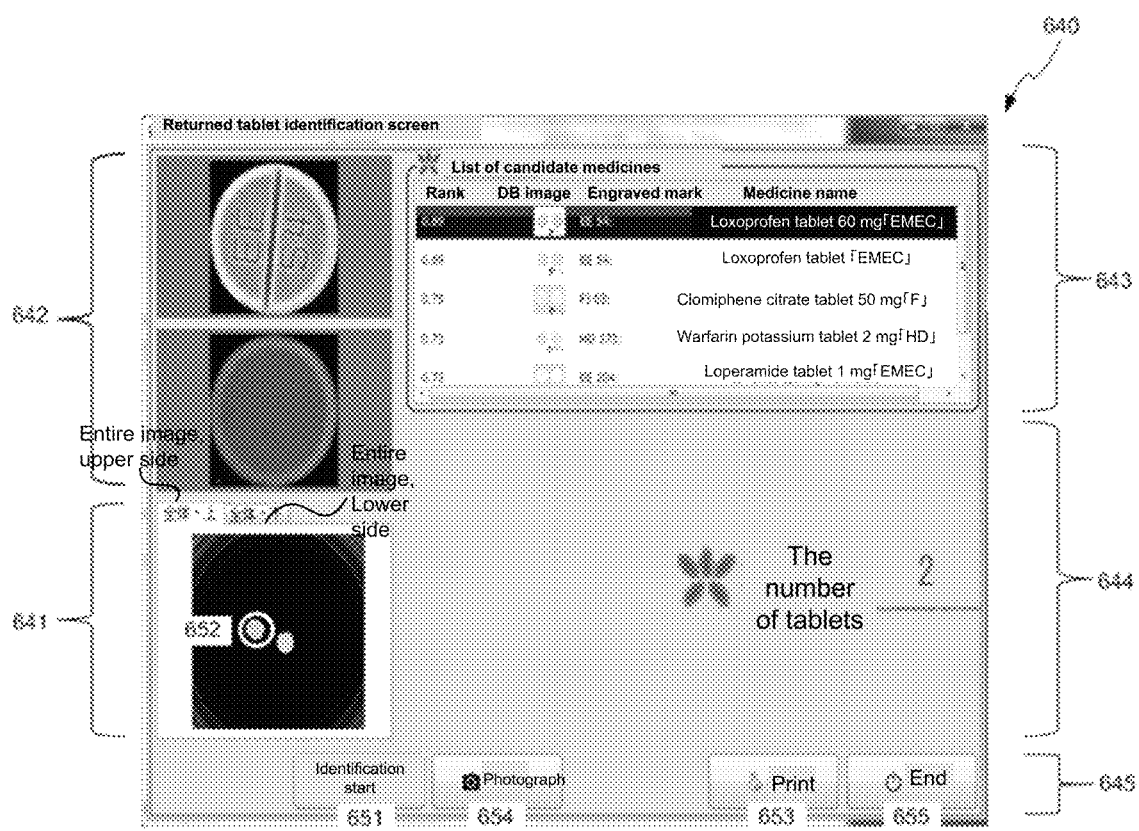

FIG. 20 is a screen image at the fourth stage of the medicine image identification started at the case shown in FIG. 17.

Figure 21:
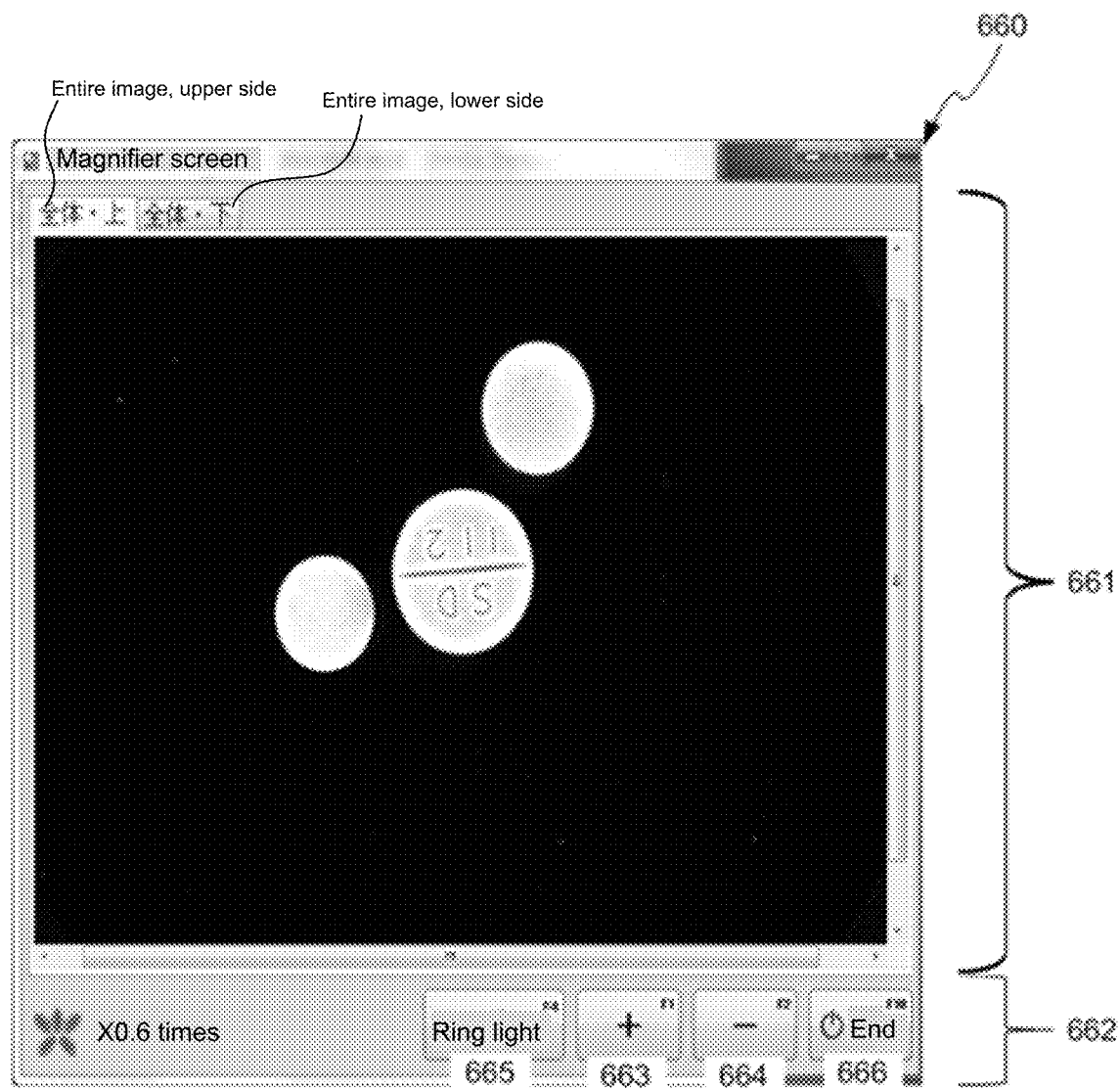

FIG. 21 is a screen image at the time of using a magnifier function of the medicine identifying software.

Each of FIGS. 22 to 25 shows an operating procedure of the medicine identifying software for automatically identifying the medicine.

Figure 22:
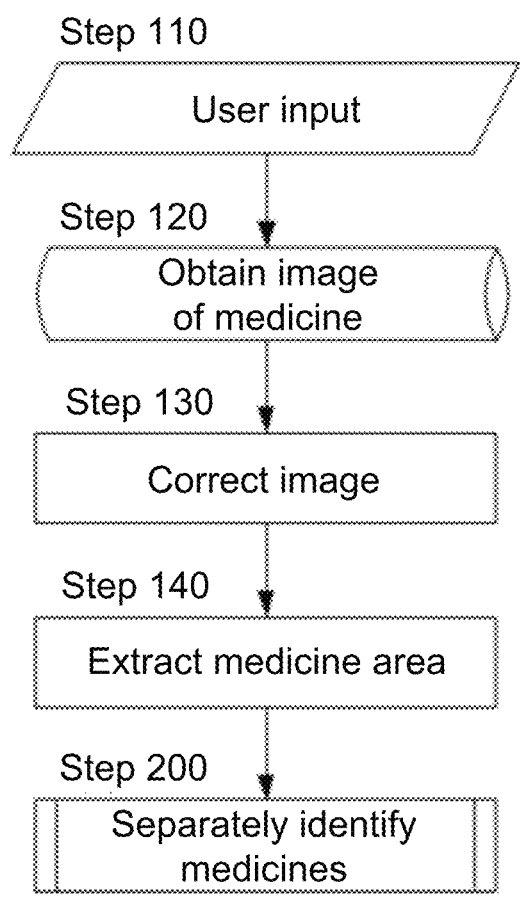

FIG. 22 is a flow chart showing a process at an upstream part of the identification.

Figure 23:
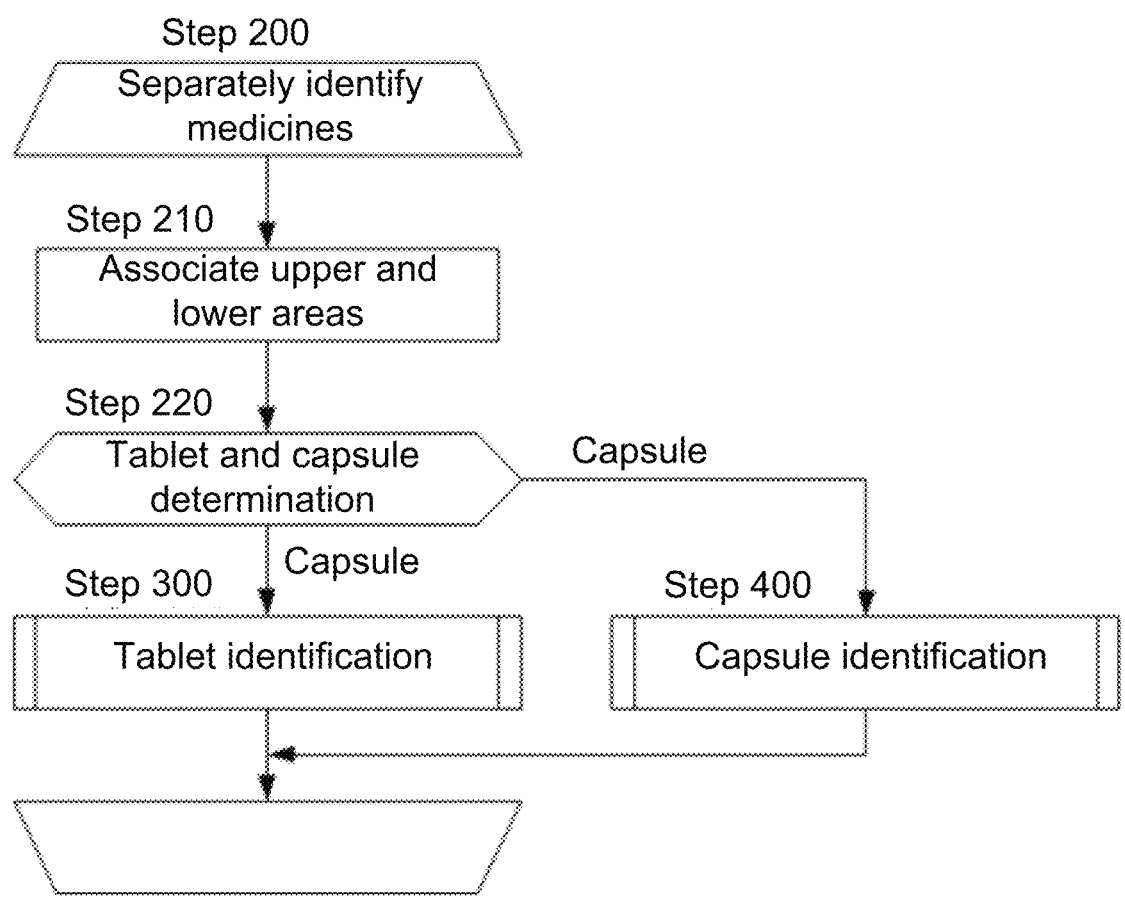

FIG. 23 is a flow chart showing a process of medicine individual identification.

Figure 24:
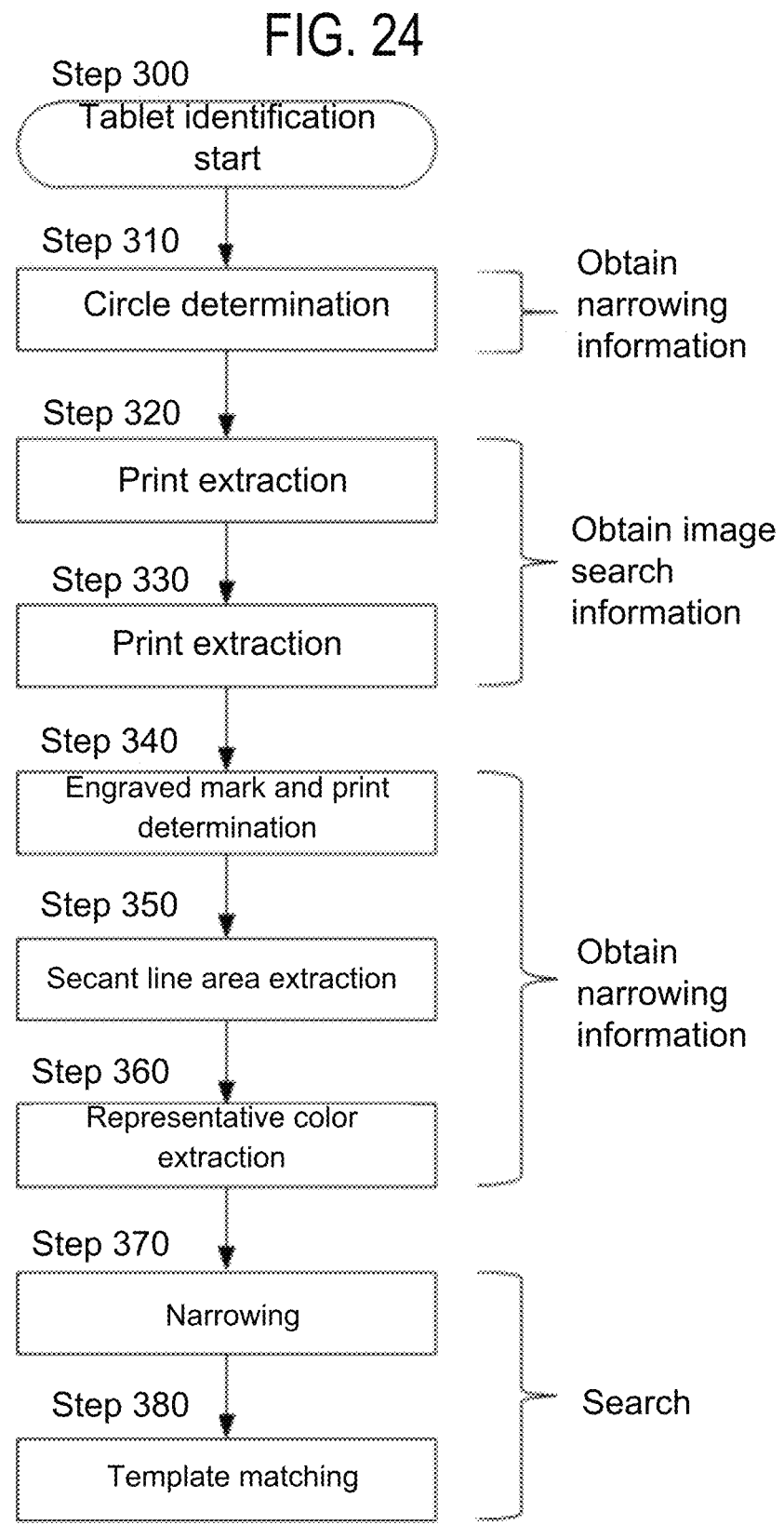

FIG. 24 is a flow chart showing a process of tablet identification.

Figure 25:
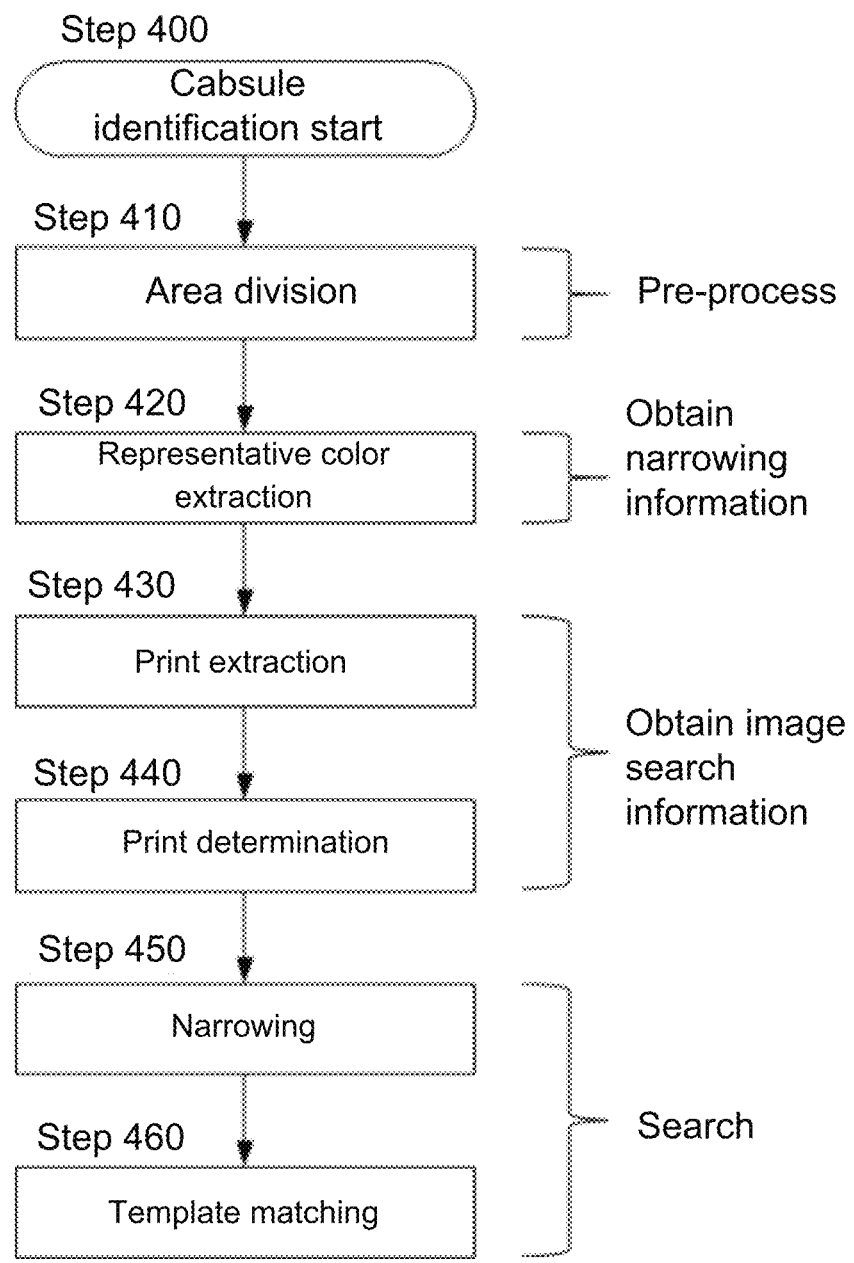

FIG. 25 is a flow chart showing a flow chart of a process of capsule identification.

Figure 26:
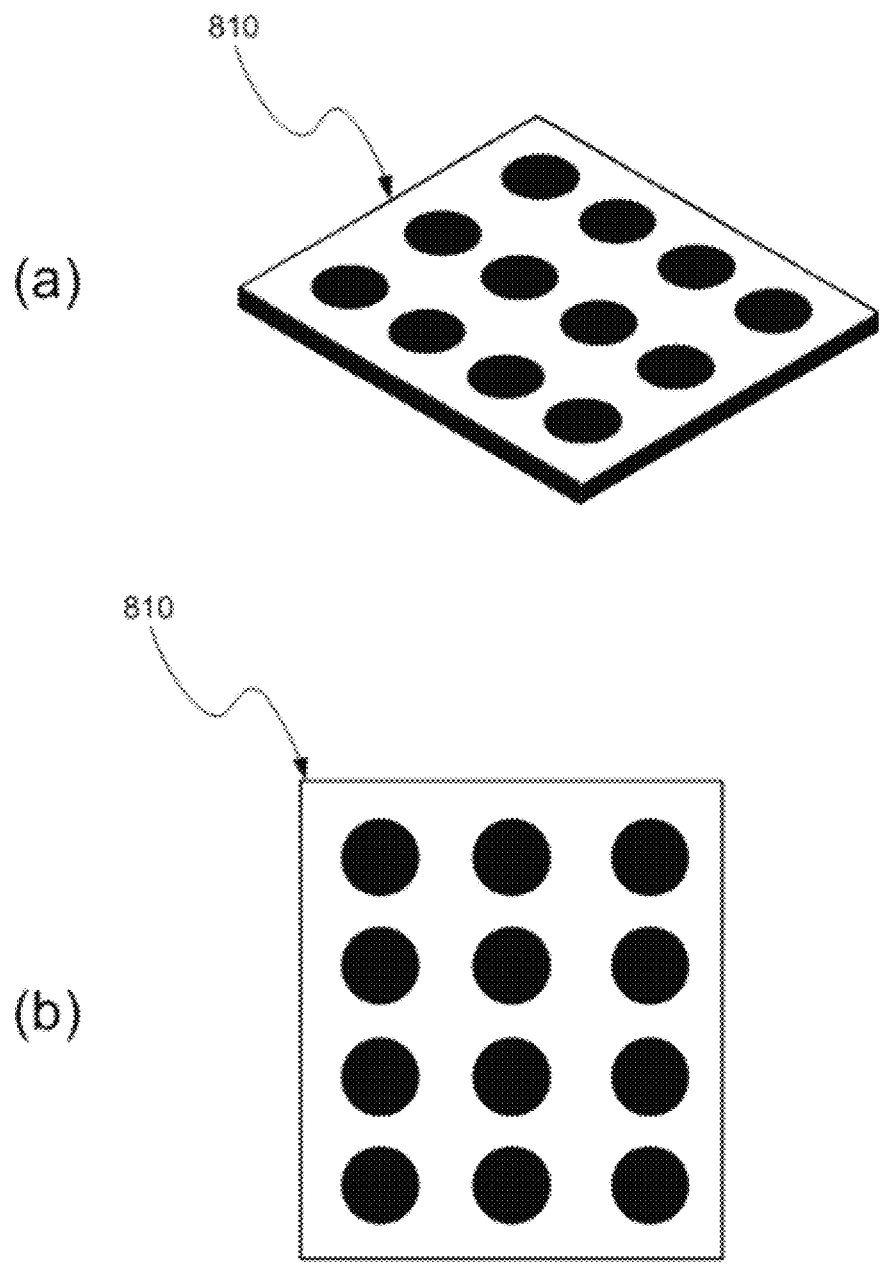

FIG. 26A is a perspective view of a calibration sheet used for calibration of a camera. FIG. 26B is a planar view of the calibration sheet.

Figure 27:
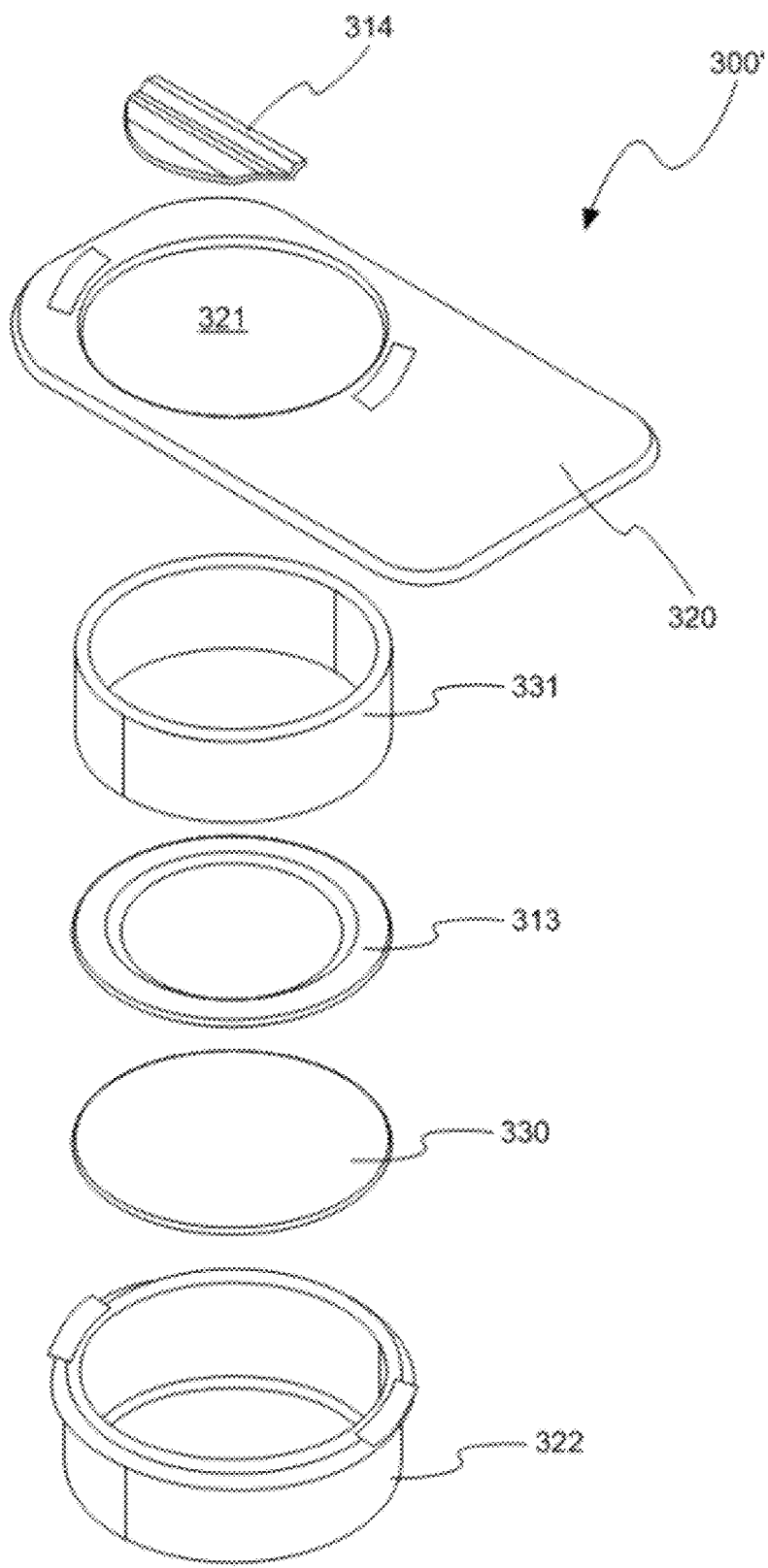

FIG. 27 is an exploded perspective view of a second embodiment of the tray to be set in the medicine photographing device.

Figure 28:
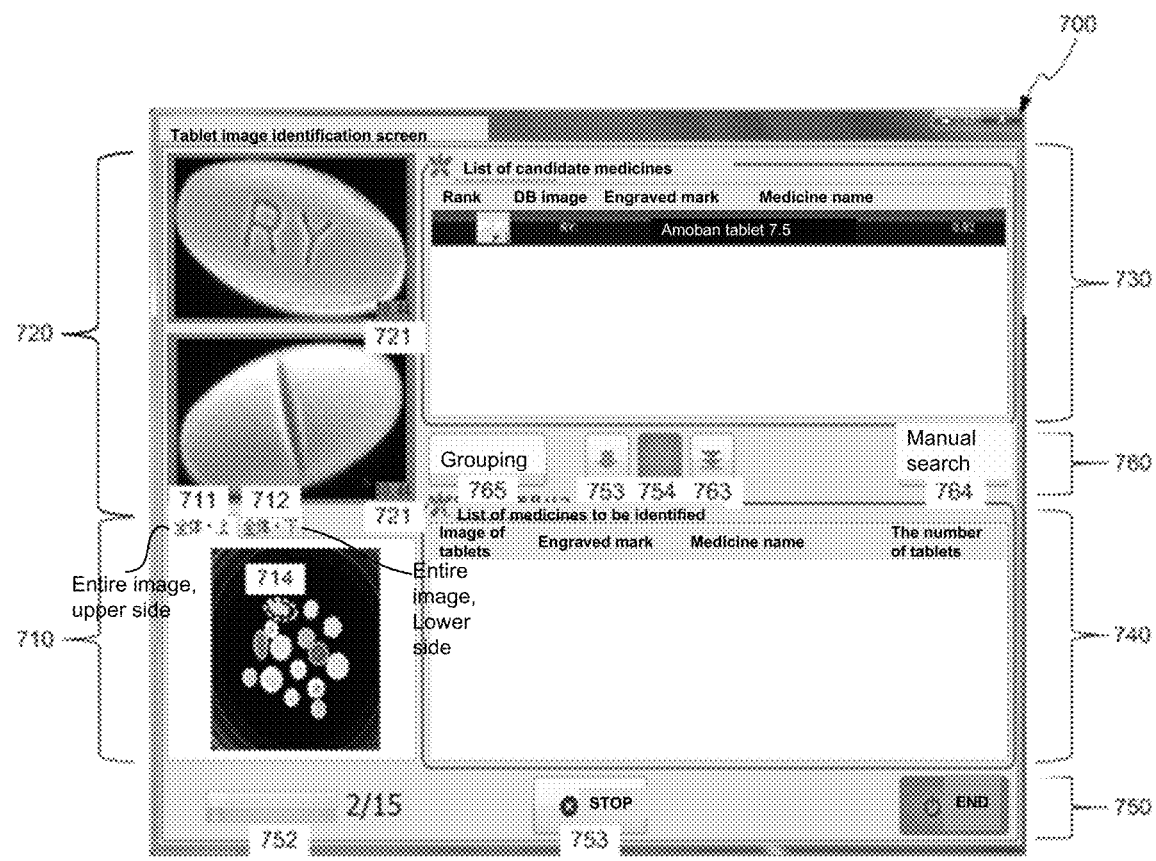

FIG. 28 is a screen image of another embodiment at the third stage for performing the medicine image identification.

Figure 29:
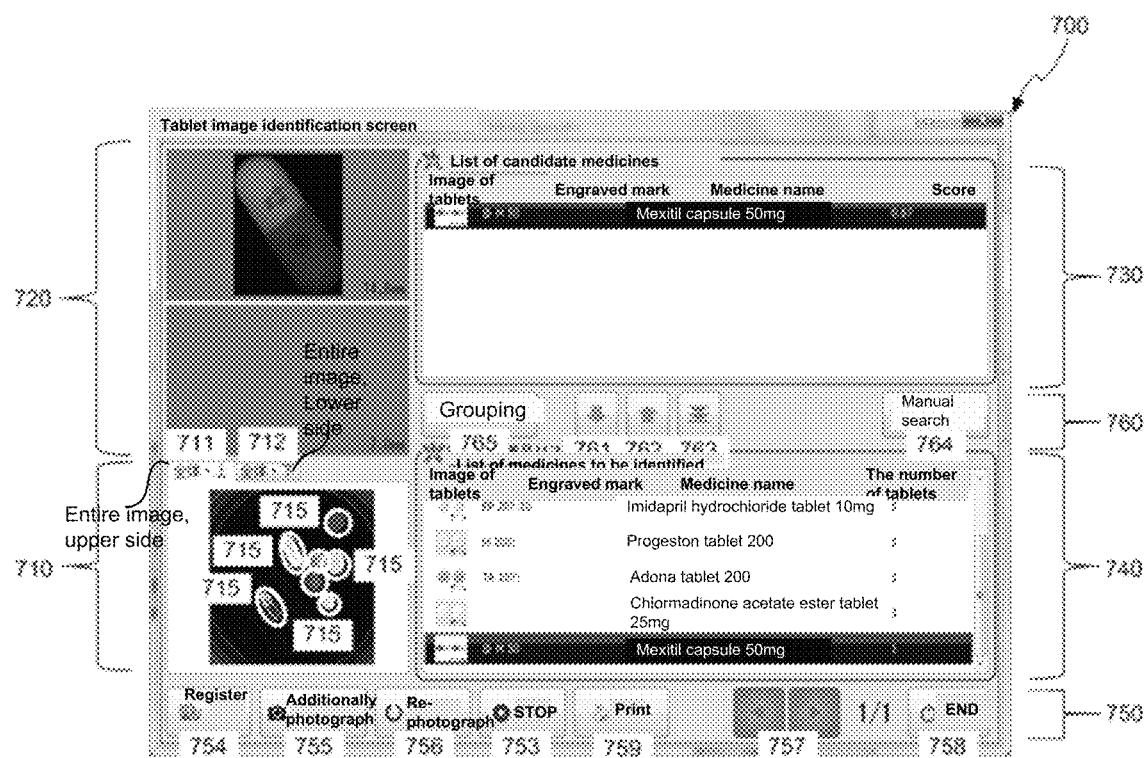

FIG. 29 is a screen image of the other embodiment at the sixth stage for performing the medicine image identification.

Figure 30:
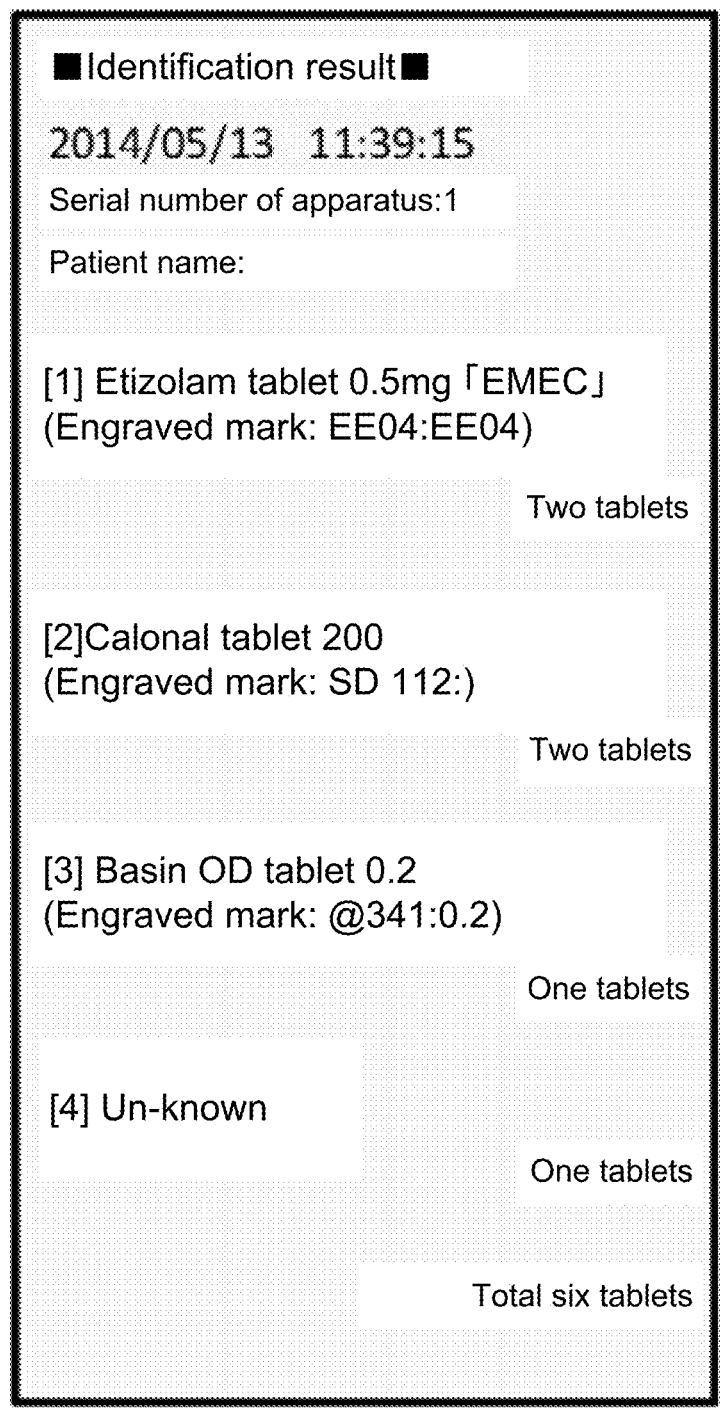

FIG. 30 is a print image at the time of printing an identification result.

Figure 31:
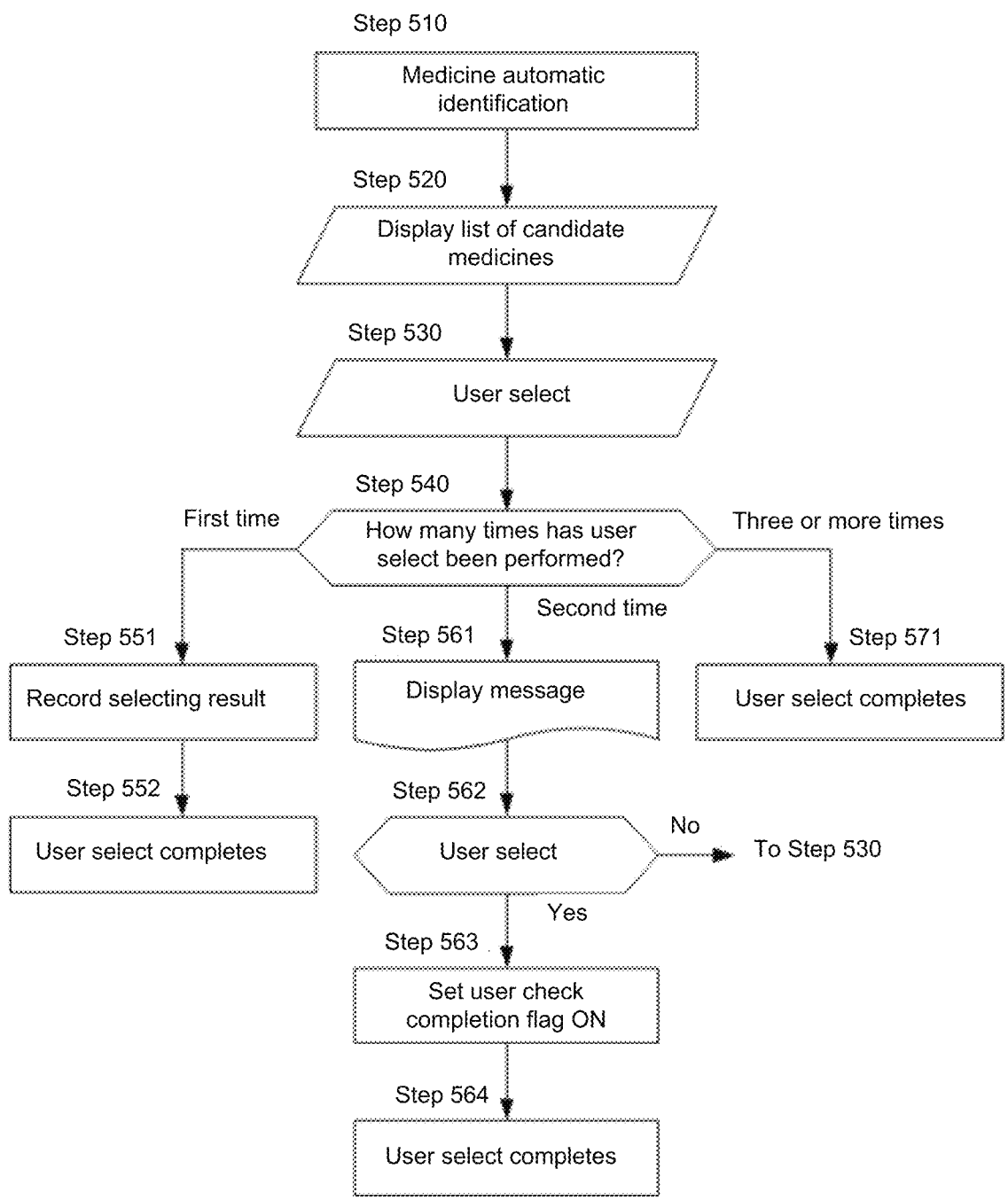

FIG. 31 is a flow chart showing a procedure of automatic learning.

Figure 32:

FIG. 32 is an image of a message displayed on a screen at the time of the automatic learning.

Figure 33:
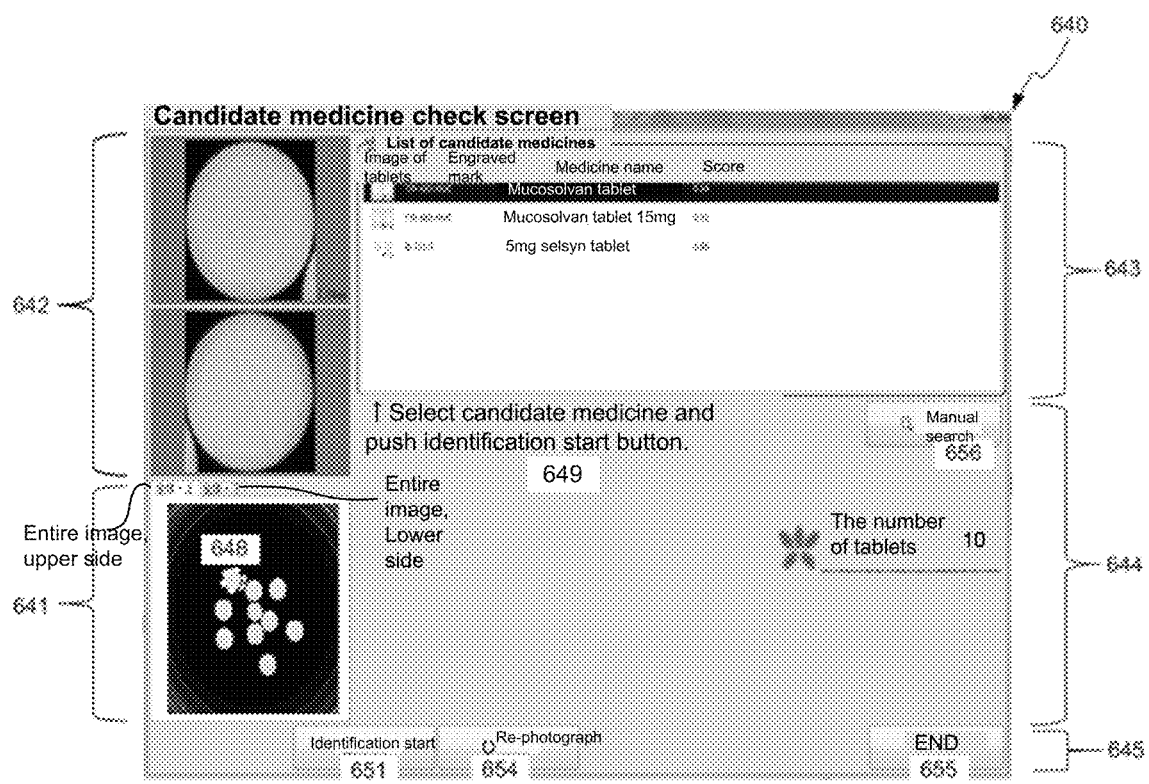

FIG. 33 is a screen image at the fifth stage of the medicine image identification started at the case shown in FIG. 17.

Figure 34:
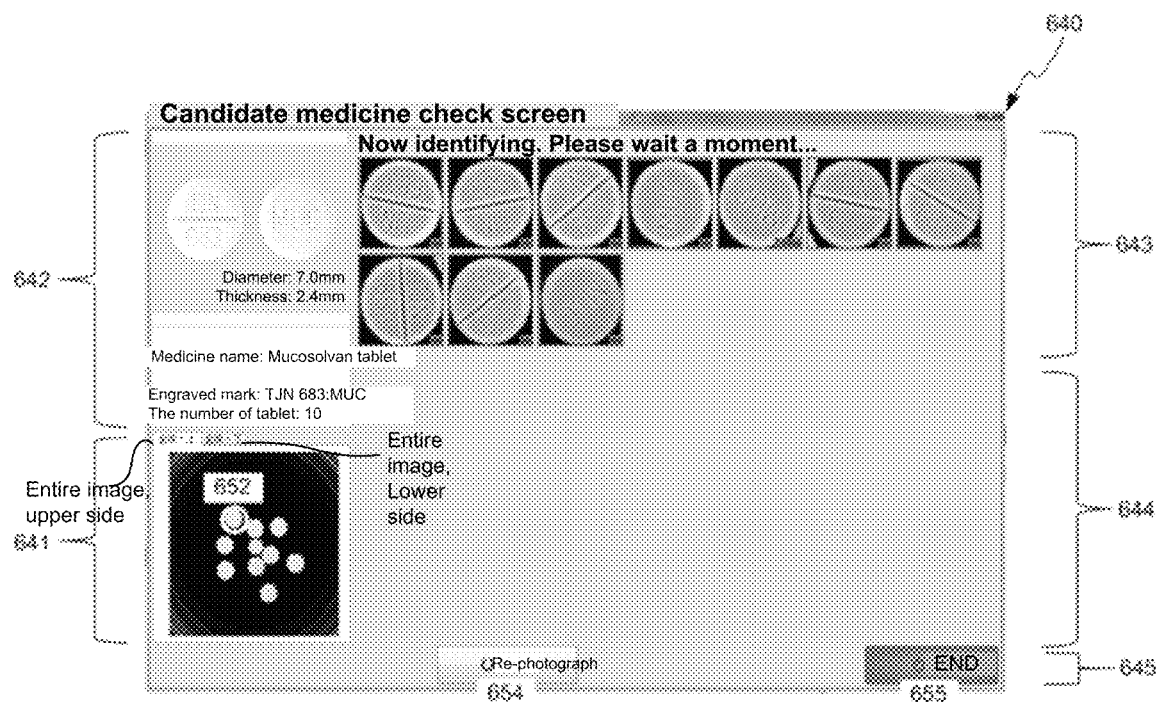

FIG. 34 is a screen image at the sixth stage of the medicine image identification started at the case shown in FIG. 17.

Figure 35:
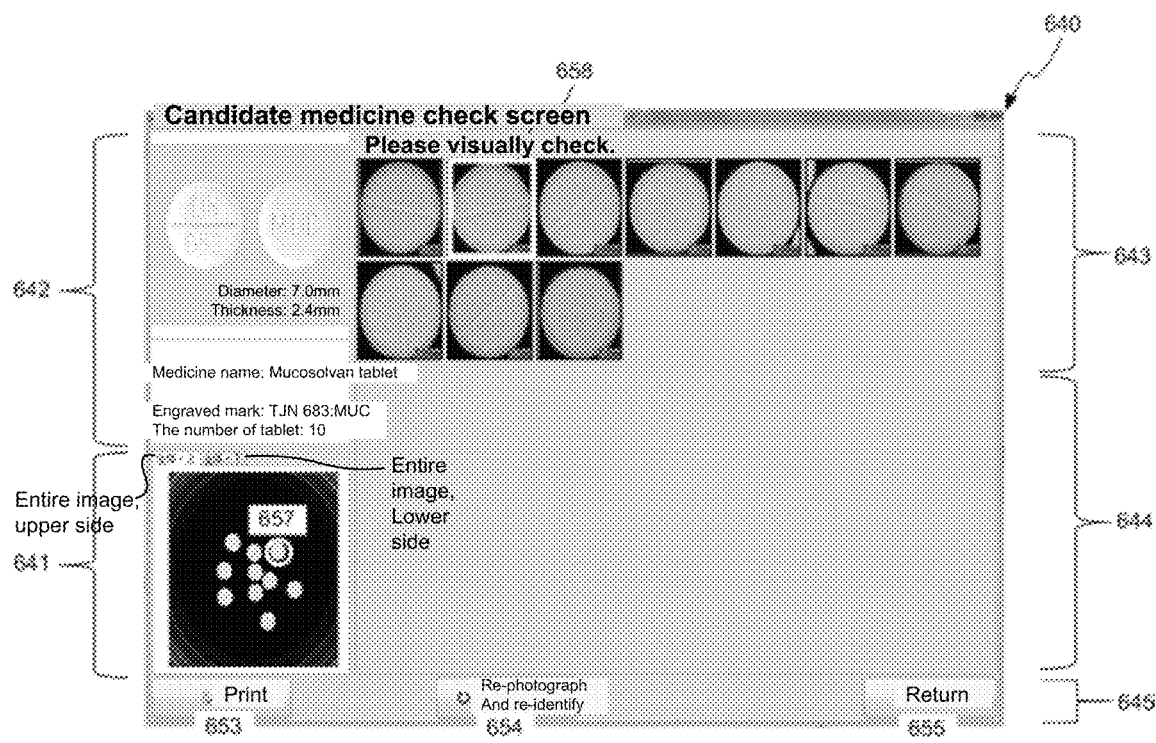

FIG. 35 is a screen image at the seventh stage of the medicine image identification started at the case shown in FIG. 17.

FIG. 36 is an image of a message displayed before the identification result is printed.

Figure 37:
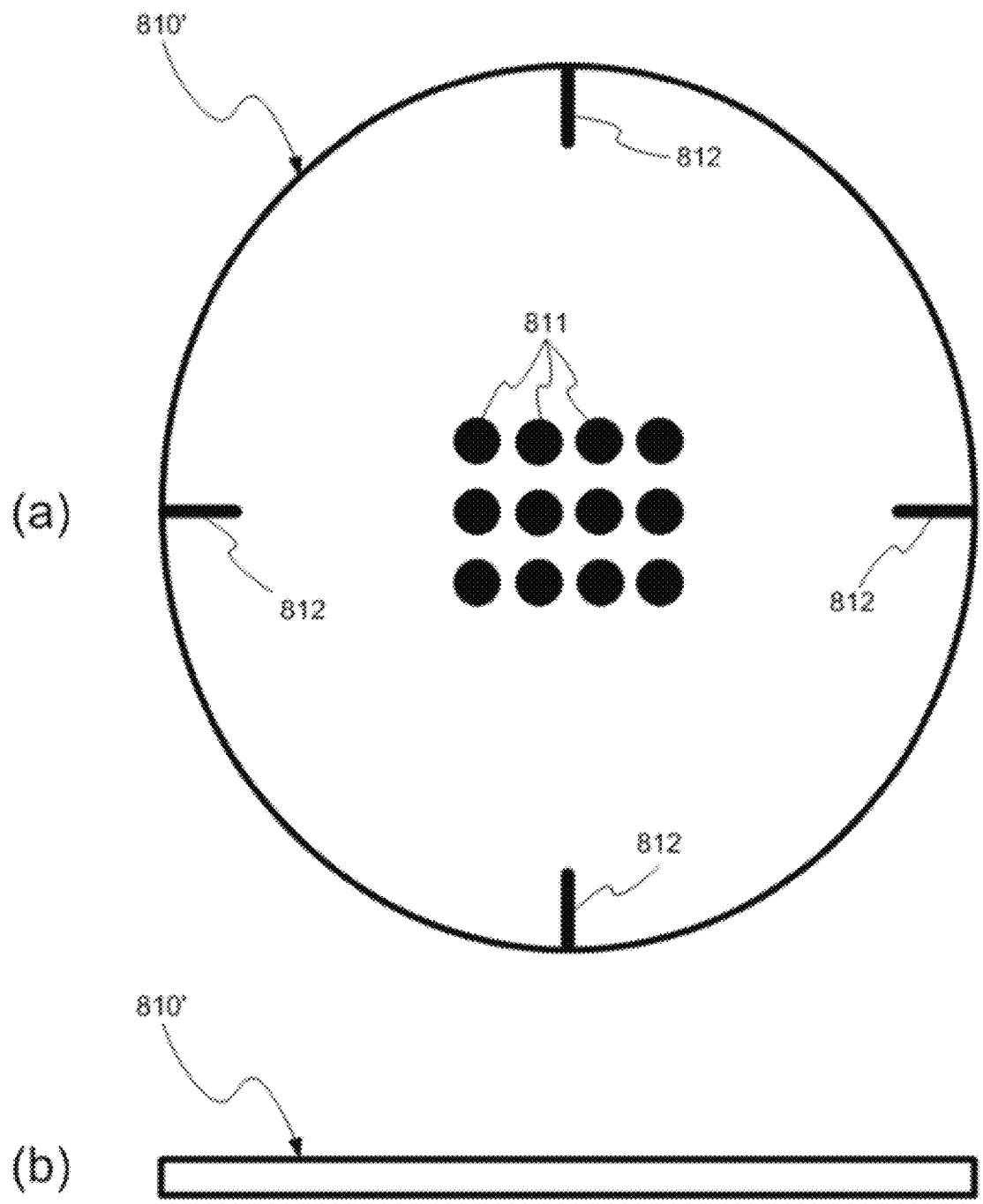

FIG. 37A is a planar view of a second embodiment of the calibration sheet used for the calibration of the camera. FIG. 37B is a side view of the calibration sheet of the second embodiment.

Figure 38:
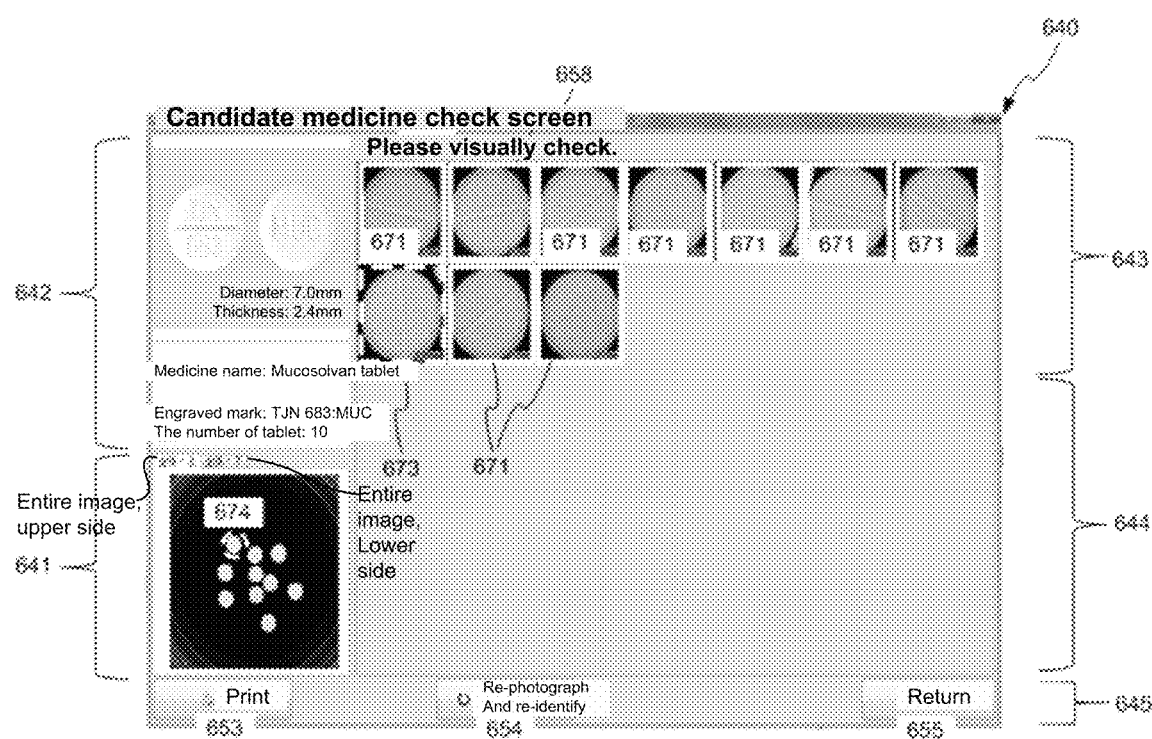

FIG. 38 is a screen image of a second embodiment at the seventh stage of the medicine image identification started at the case shown in FIG. 17.

Figure 39:
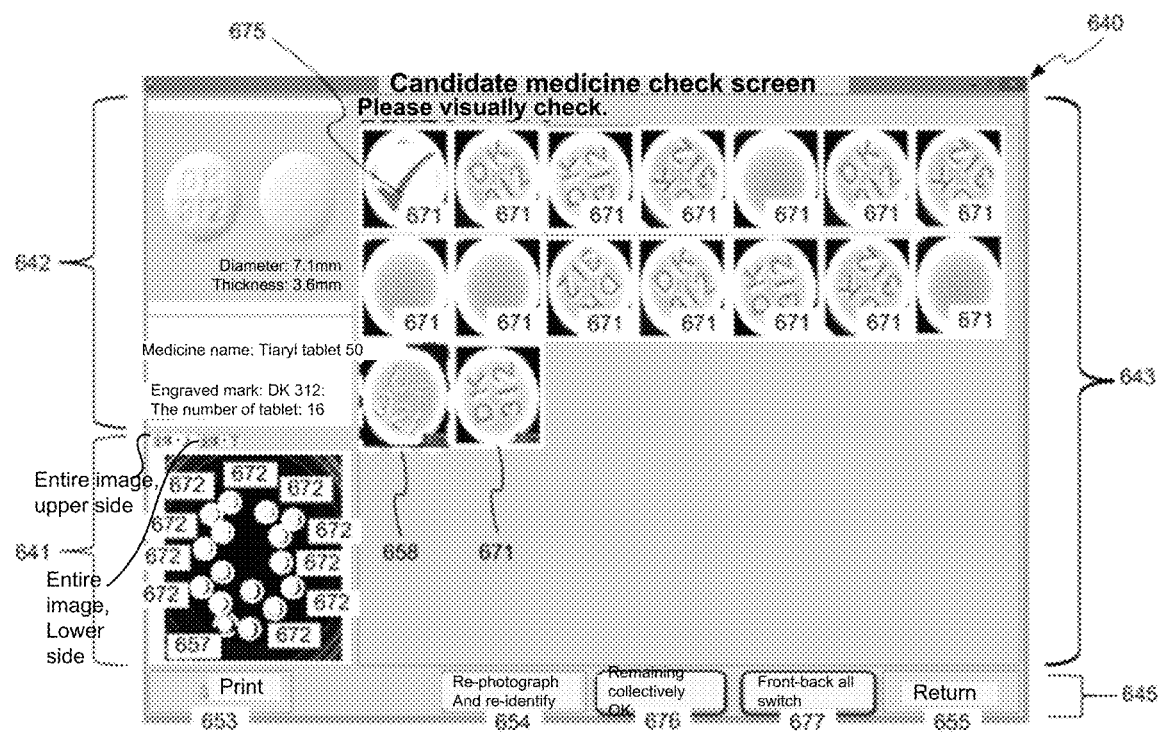

FIG. 39 is a screen image of a third embodiment at the seventh stage of the medicine image identification started at the case shown in FIG. 17.

Figure 40:
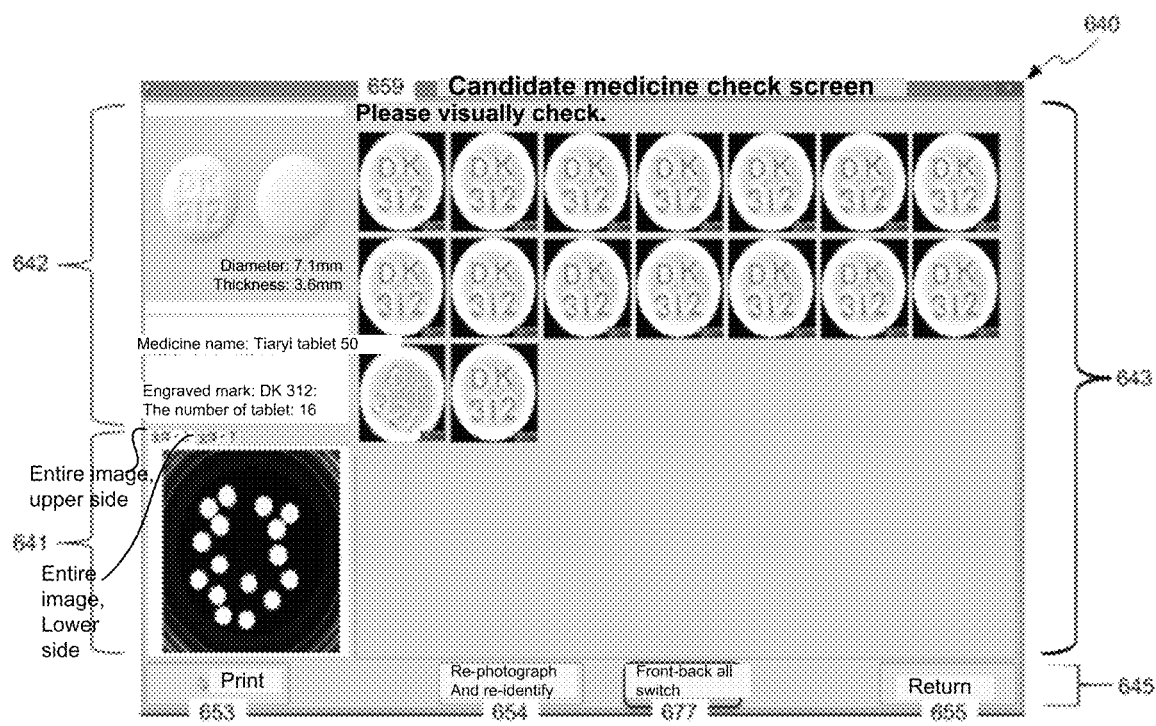

FIG. 40 is a screen image of a fourth embodiment at the seventh stage of the medicine image identification started at the case shown in FIG. 17.

Figure 41:
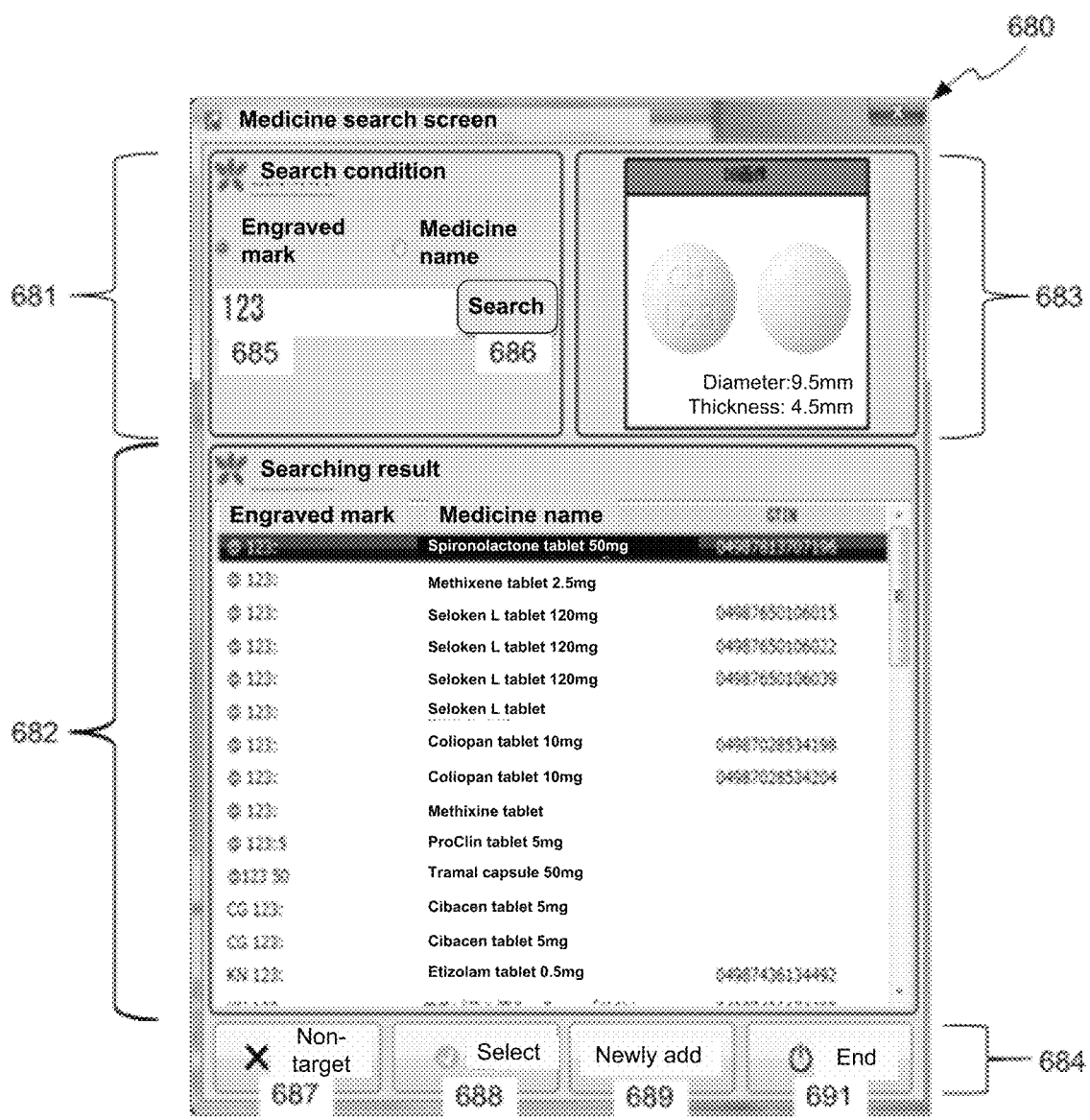

FIG. 41 is a screen image of medicine manual search.

Figure 42:

FIG. 42 is a screen image at the time of identifying a medicine in packaging paper.

DETAILED DESCRIPTION OF THE INVENTION

§1 Medicine Identifying System

Figure 1:
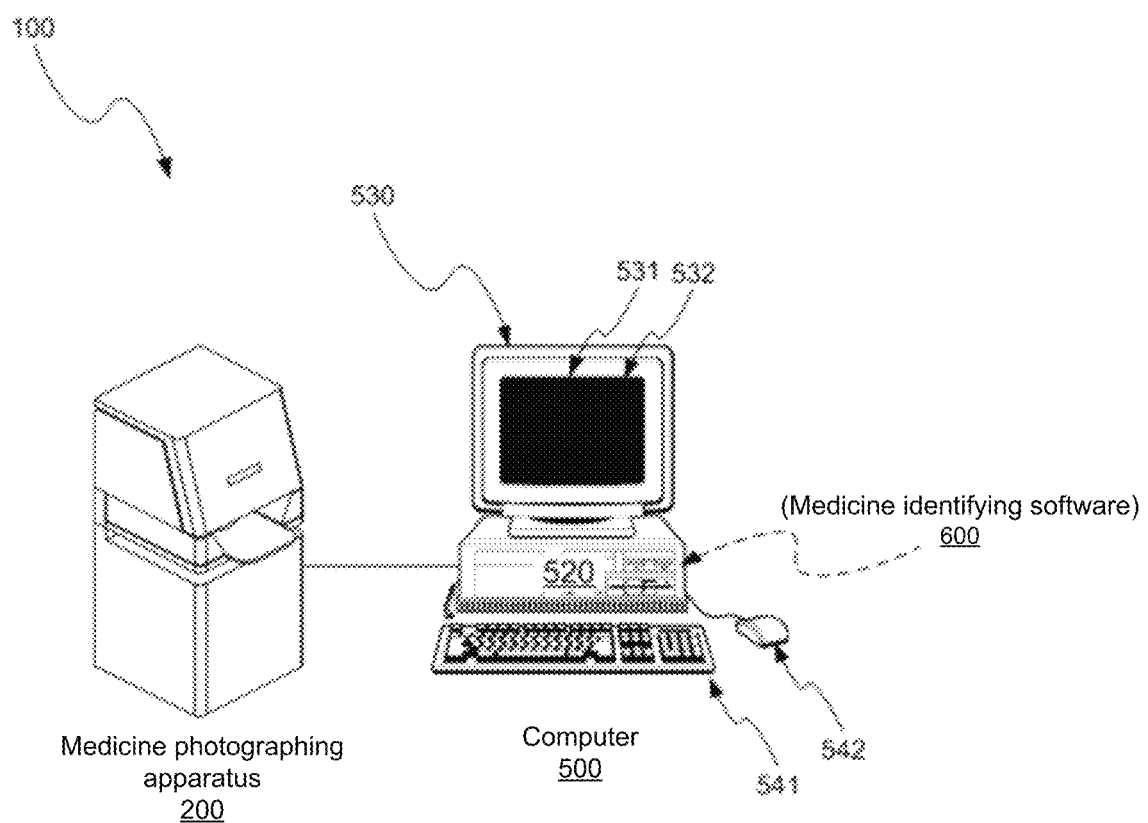
FIG. 1 is a schematic view showing a schema of a medicine identifying system.

FIG. 1 is a schematic view showing a schema of a medicine identifying system. As shown in FIG. 1, a medicine identifying system 100 is constituted of a medicine photographing device 200 and a computer 500. In the medicine identifying system 100, the medicine photographing device 200 photographs a medicine and the computer 500 identifies the medicine based on obtained image data of the medicine.

The computer 500 includes a main body 520 having a CPU, a storage device, a recording device and the like built-in, a display device 530 serving as an output device, a keyboard 541 and a mouse 542 serving as an input device. The display device 530 includes a screen 531 and a touch screen 532. A user can also input an instruction into the computer 500 through the touch screen 532. Further, medicine identifying software 600 is installed in the computer 500. With referring to this matter about the computer 500, the computer 500 in which the medicine identifying software (often referred to as a medicine identifying program) 600 is installed can be referred to as a medicine identifying apparatus. In this embodiment, although the computer 500 is constituted of a so-called PC (Personal Computer) and the medicine identifying software 600 is stored in the recording device in the PC, the computer 500 may not be the PC but a microcomputer built in another apparatus, for example. In this case, the medicine identifying software 600 may be written on a storage device such as a ROM (Read Only Memory) of that apparatus.

When the medicine is identified, the user first sets a medicine to be identified in the medicine photographing device 200. Next, by utilizing an operation of the user with respect to the computer 500 as a trigger, the medicine photographing device 200 starts to photograph the medicine. A photographed image of the medicine is transmitted to the computer 500 as data. Then, the computer 500 accesses a database (not shown in the drawings) to search the medicine based on this image data.

In one embodiment, the computer 500 has a database built-in. For example, in the case where a medicinal product integrated database "MDbank" (registered trademark) made by YUYAMA Co., Ltd is installed in the computer 500, the computer 500 can search the medicine by accessing the MDbank without accessing an external database. In another embodiment, the computer 500 accesses a database through a network. For example, in the case where a medication teaching assistant system "PharmaRoad" (registered trademark) made by YUYAMA Co., Ltd is installed in another computer (server) in the same facility, the computer 500 can search the medicine by accessing the PharmaRoad in the server through a LAN (Local Area Network). Further, in another embodiment, the computer 500 may access a database through the internet.

Hereinafter, the medicine photographing device 200 will be described in detail. After that, the medicine identifying software 600 will be described in detail.

§2 Medicine Photographing Device

FIG. 2 is a perspective view showing an external view of the medicine photographing device 200. Although an internal configuration of the medicine photographing device 200 cannot be viewed due to a case 210 in FIG. 2, a placing part 220 on which the medicine is to be placed is provided at a substantially central portion in the medicine photographing device 200. More specifically, the medicine is put into a tray 300 as shown in FIG. 7A through FIG. 7C and then this tray 300 is set on the placing part 220. Hereinafter, for the purpose of illustration, a portion located on the upper side of the placing part 220 is referred to as an upper portion 201 and a portion located on the lower side of the placing part 220 is referred to as a lower portion 202 in the medicine photographing device 200.

§2.1 External Configuration of Medicine Photographing Device

As shown in FIG. 2, from the outside of the medicine photographing device 200, a lower case 211, a cutout portion 212, a tray supporting member 221 and a pair of guide members 230, an upper case 213 and a cover 214 can be viewed.

The lower case 211 covers the lower portion 202 of the medicine photographing device 200. The cutout portion 212 extending in the horizontal direction is formed on an upper surface of the lower case 211. The cutout portion 212 is opened toward the left-right direction and the front direction of the medicine photographing device 200. The user can insert elongated package paper into the medicine photographing device 200 through the cutout portion 212. Specifically, the user unfolds the package paper in the horizontal direction to insert the package paper into the cutout portion 212 from the front side of the medicine photographing device 200. Then, the package paper is moved to the vicinity of the central portion of the medicine photographing device 200. This allows an internal camera of the medicine photographing device 200 to photograph a medicine packaged in the package paper without cutting the package paper. Since an inner space of the medicine photographing device 200 is communicated with outer spaces in the left-right direction due to the cutout portion 212, the user can easily insert the package paper into the medicine photographing device 200 in a state that the package paper is unfolded even in the case where a width of the package paper is larger than a width of the medicine photographing device 200.

The tray supporting member 221 for supporting a member for containing the medicine is provided just above the cutout portion 212. Specifically, the tray 300 is placed on the tray supporting member 221. As shown in FIG. 6A, the tray supporting member 221 is a substantially rectangular plate-like member and a circular hole 222 is formed in a central portion thereof. As shown in FIG. 7A through FIG. 7C, a petri dish 310 is fitted in the tray 300. When the tray 300 is set on the tray supporting member 221, the petri dish 310 is inserted into the hole 222. Referring back to FIG. 6A, a concave portion having a planar shape corresponding to a planar shape of the tray 300 is formed on an upper surface of the tray supporting member 221. The concave portion forms an engaging portion 223 to be engaged with the tray 300. The tray 300 is placed on the engaging portion 223. Then, when the tray 300 is engaged with the engaging portion 223, the tray 300 is stably held on the tray supporting member 221.

As shown in FIG. 2, the cover 214 covers an upper surface of the medicine photographing device 200 and a front surface of the upper portion 201. As shown in FIG. 3, the cover 214 can be opened toward the upper direction. Specifically, the cover 214 is hinged by a hinge 257 (see FIG. 4) at a rear and upper end portion of the upper case 213. Thus, the cover 214 can be pivotally moved in the vertical direction around the hinge 257.

FIG. 3 shows a state that the cover 214 of the medicine photographing device 200 is opened. As shown in FIG. 3, when the cover 214 is opened, an upper inner space 240 which is the upper portion 201 of the inner space of the medicine photographing device 200 is opened toward a space on the front side of the medicine photographing device 200. Thus, the user can set the tray 300 on the engaging portion 223 of the placing part 220 through this upper inner space 240.

As shown in FIG. 3, a front and outer surface of the upper case 213 has a substantially inverted U-like shape. This front and outer surface is inclined to form an inclined portion 215. Specifically, the inclined portion 215 is inclined so that a distance between the inclined portion 215 and a rear surface of the medicine photographing device 200 decreases from the lower side to the upper side. With this configuration, the user can easily insert the tray 300 into the upper inner space 240. The user often moves the tray 300 from the obliquely upward direction toward the obliquely downward direction to insert the tray 300 into the upper inner space 240. At this time, if the inclined portion 215 is inclined so as to extend toward the rear side as the inclined portion 215 extends toward the upper side, a larger space is ensured on the upper and front side of the inclined portion 215 and thus the tray 300 becomes unlikely to be contacted to the upper case 213. A front surface of the cover 214 is configured so as to cover the inclined portion 215. Thus, when the cover 214 is closed, the front surface of the cover 214 is positioned in the vicinity of the inclined portion 215 and becomes parallel to the inclined portion 215. As the upper surface of the upper case 213 and the inclined portion 215 form an obtuse angle as described above, the upper surface and the front surface of the cover 214 also form an obtuse angle.

A lower end of the inclined portion 215 is positioned on the rear side of the guide members 230 and a front and outer surface of the lower case 211. Namely, a distance between the rear surface of the medicine photographing device 200 and the lower end of the inclined portion 215 is smaller than a distance between the rear surface of the medicine photographing device 200 and a front and outer surface of each of the guide members 230 and a distance between the rear surface of the medicine photographing device 200 and the front and outer surface of the lower case 211. With this configuration, the user can more easily insert the tray 300 into the upper inner space 240.

Further, an inclined surface 216 other than the inclined portion 215 is formed on the front and outer surface of the upper case 213. More specifically, the inclined surface 216 is provided inside the U-like shape of the inclined portion 215 having the substantially inverted U-like shape. The inclined surface 216 is provided on the front side of an after-mentioned first camera 410 (see FIG. 4) to protect the first camera 410. With this configuration, it is possible to prevent the tray 300 from being contacted to the first camera 410 when the user inserts the tray 300 into the upper inner space 240. Thus, it is possible to prevent a position and a direction of the first camera 410 from being changed due to the contact between the first camera 410 and the tray 300. As shown in FIG. 3, the inclined surface 216 has a substantially rectangular shape and extends toward the left-right direction of the medicine photographing device 200. Further, a distance between the rear surface of the medicine photographing device 200 and the inclined surface 216 gradually decreases from the upper side to the lower side. Namely, a distance between a horizontal position of an upper end of the inclined surface 216 and the rear surface of the medicine photographing device 200 is larger than a distance between a horizontal position of the lower end of the inclined surface 216 and the rear surface of the medicine photographing device 200. With this configuration, the tray 300 becomes unlikely to be contacted to the inclined surface 216 at the time of inserting the tray 300. Thus, the user can easily insert the tray 300 to the rear side of the upper inner space 240.

As shown in FIG. 3, the pair of guide members 230 are provided between the upper case 213 and the placing part 220. An outer lateral surface of each of the guide members 230 extends in the vertical direction. Further, the outer lateral surface of each of the guide members 230 and each of outer lateral surfaces of the upper case 213 are positioned in the same plane. In contrast, an inner lateral surface of each of the guide members 230 is inclined with respect to the vertical direction to form inclined surfaces 231 as shown in FIGS. 3 to 5. Each of the inclined surfaces 231 has a substantially rectangular shape and extends in the front-back direction of the medicine photographing device 200. Further, each of the inclined surfaces 231 faces the upper inner space 240. One of the inclined surfaces 231 is positioned on the right and upper side of the placing part 220 and the other one of the inclined surfaces 231 is positioned on the left and upper side of the placing part 220. Each of the inclined surfaces 231 is formed so as to approach to a center axis of the medicine photographing device 200 as each of the inclined surfaces 231 extends from the upper side to the lower side. Namely, in the planar view, a distance between a horizontal position of a lower end of each of the inclined surfaces 231 and the placing part 220 is smaller than a distance between a horizontal position of an upper end of each of the inclined surfaces 231 and the placing part 220. Further, a distance between the lower ends of the two inclined surfaces 231 is substantially equal to or slightly larger than a width of the engaging portion 223 of the tray supporting member 221 (see FIG. 6A). Specifically, it is preferable that the distance between the lower ends of the two inclined surfaces 231 is about 1 to 1.2 times of the width of the engaging portion 223. Further, in the planar view of the medicine photographing device 200, a part of the lower end of each of the inclined surfaces 231 is located at a position substantially contacting a peripheral portion of the hole 222 of the tray supporting member 221. With this configuration, the user can easily place the tray 300 on the engaging portion 223 of the tray supporting member 221.

§2.2 Internal Configuration of Medicine Photographing Device

Each of FIGS. 4 and 5 is a view showing a state that the cases of the medicine photographing device 200 are removed, that is a view showing main members in the medicine photographing device 200. Specifically, FIG. 4 is a perspective view of the medicine photographing device 200 and FIG. 5 is a front view of the medicine photographing device 200.

As shown in FIG. 4, a frame 250 is provided on the side of the rear surface of the medicine photographing device 200. Almost of the main members of the medicine photographing device 200 have configurations directly or indirectly attached to the frame 250. The frame 250 is constituted of a first pole 251, a second pole 252, a third pole 253, a first beam 254, a second beam 255, a third beam 256 and a hinge 257. In the front view, the first pole 251 is provided at a left side portion of the rear surface of the medicine photographing device 200, the second pole 252 is provided at a central portion of the rear surface of the medicine photographing device 200 and the third pole 253 is provided at a right side portion of the rear surface of the medicine photographing device 200. The first pole 251, the second pole 252 and the third pole 253 are connected with each other by the first beam 254, the second beam 255 and the third beam 256. Further, the hinge 257 for pivotally moving the cover 214 (see FIG. 3) is attached to the third beam 256 positioned at a top portion of the frame 250.

As shown in FIGS. 4 and 5, the medicine photographing device 200 includes the first camera 410, a second camera 420, a first light source 430, a second light source 440, a third light source 450, a fourth light source 460, the tray supporting member 221 and the guide members 230. Among them, the tray supporting member 221 and the guide members 230 are directly attached to the frame 250. The first camera 410, the second camera 420, the third light source 450 and the fourth light source 460 are attached to the frame 250 through supporting members. The first light source 430 is contained in the tray supporting member 221 and supported by the tray supporting member 221. Although this matter is not shown in the drawings, the second light source 440 is attached to the lower case 211 (see FIG. 2) through the supporting member. As described above, the main members in the medicine photographing device 200 are attached to not the case 210 but the frame 250. This makes it possible to easily remove the case 210, thereby easily performing maintenance work for the internal main members.

The tray supporting member 221 is provided in the vicinity of the central portion of the medicine photographing device 200. Further, the guide members 230 are provided at upper nearest positions of the tray supporting member 221. The third light source 450 is provided on the upper side of the guide members 230. Further, the first camera 410 is provided at a position higher than the third light source 450, that is in the vicinity of the upper surface of the medicine photographing device 200. The second light source 440 is provided on the lower side of the tray supporting member 221 so as to be spaced apart from the tray supporting member 221 by a predetermined distance. The fourth light source 460 is provided at a position which is lower than the second light source 440 and in the vicinity of the lateral surface of the medicine photographing device 200. The second camera 420 is provided at a position lower than the fourth light source 460, that is in the vicinity of a bottom surface of the medicine photographing device 200. As described above, in the medicine photographing device 200, an upper light source is constituted of the first light source 430 and the third light source 450. Further, in the medicine photographing device 200, a lower light source is constituted of the second light source 440 and the fourth light source 460.

As described above, the tray supporting member 221 is provided at a position which is in the vicinity of the central portion of the medicine photographing device 200 and on the upper side of the space 217 for the cutout portion 212. As shown in FIG. 6A, the engaging portion 223 is formed on the upper surface of the tray supporting member 221 and the tray 300 (see FIG. 7A through FIG. 7C) is placed on the engaging portion 223 at the time of using the medicine photographing device 200. Further, the first light source 430 is attached to a bottom portion of the tray supporting member 221. The first light source 430 includes a first ring lighting part 431. The first ring lighting part 431 is constituted of a plurality of light emitting diodes (LEDs) arranged so as to form a ring shape. The plurality of LEDs are arranged so as to surround an outer peripheral portion of the hole 222 of the tray supporting member 221 and face the hole 222.

As shown in FIG. 6B, when the tray 300 is placed on the engaging portion 223, the petri dish 310 protrudes toward the lower side of the tray supporting member 221 through the hole 222. Thus, a bottom portion 311 of the petri dish 310 is positioned lower than a lower surface of the tray supporting member 221. In other words, when the tray 300 is placed on the engaging portion 223, the petri dish 310 is inserted into the ring of the first ring lighting part 431 and the bottom portion 311 of the petri dish 310 is positioned at a position lower than the first ring lighting part 431. Namely, when the tray 300 is placed on the engaging portion 223, the first ring lighting part 431 is located at a position which is higher than the bottom portion 311 of the petri dish 310 and lower than the upper surface or an upper end (a highest portion of the tray 300) of the tray 300. At least the bottom surface and a lateral surface, which faces the hole 22, of the tray supporting member 221 are made of a transparent material. As a result, when the first ring lighting part 431 emits light, the emitted light is transmitted toward a center of the hole 222 and in the lower direction. As a result, the medicine supplied onto the bottom portion 311 of the petri dish 310 is directly illuminated with the light emitted from the first ring lighting part 431 from every direction of 360° and the obliquely upward direction. Namely, the first light source 430 serves as a direct light source for directly illuminating the medicine.

As shown in FIG. 6B, the second light source 440 is provided on the lower side of the tray supporting member 221 so as to be spaced apart from the tray supporting member 221 through the space 217 for the cutout portion. The second light source 440 is constituted of a second ring lighting part 441 which is the same kind as the first ring lighting part 431. The second ring lighting part 441 is supported by a lower supporting board 442 and an upper supporting board 443. The lower supporting board 442 and the upper supporting board 443 are attached to an inner lateral surface of the lower case 211 (see FIG. 2). The upper supporting board 443 is made of a transparent material. The upper supporting board 443 has a substantially rectangular planar shape. Further, unlike the tray supporting member 221, the upper supporting board 443 does not have a hole at a central portion thereof (on the lower side of the hole 222). With this configuration, even if the user mistakenly drops the medicine in the placing part 220, it is possible to prevent the dropped medicine from being contacted to the second camera 420. The lower supporting board 442 has a planar shape corresponding to the planar shape of the second ring lighting part 441. Further, the lower supporting board 442 includes a hole which is formed in a central portion of the lower supporting board 442 and has a shape corresponding to the ring of the second ring lighting part 441. The second ring lighting part 441 is positioned lower than the bottom portion 311 of the petri dish 310. Further, the second ring lighting part 441 is arranged so that a planar position of the second ring lighting part 441 coincides with a planar position of the first ring lighting part 431. When the second ring lighting part 441 emits light, the emitted light is transmitted toward the center of the hole 222 and in the upper direction. As a result, the medicine supplied on the bottom portion 311 of the petri dish 310 is directly illuminated with the light emitted from the second ring lighting part 441 from every direction of 360° and the obliquely downward direction. The first light source 430 and the second light source 440 described above are used for photographing an engraved mark formed on a surface of the medicine (which is typically a tablet). More specifically, the first light source 430 is used for photographing an engraved mark attached to an upper surface of the medicine. The second light source 440 is used for photographing an engraved mark attached to a lower surface of the medicine. The present inventors have found that it is possible to clearly photograph the engraved marks respectively formed on the surfaces of the medicines by using the first light source 430 and the second light source 440 each having the described configurations.

As shown in FIGS. 4 and 5, the third light source 450 is provided on the upper side of the guide members 230. The third light source 450 is constituted of a plurality of bar lighting part, specifically, constituted of a first bar lighting part 451 and a second bar lighting part 452. The first bar lighting part 451 is attached to the third pole 253 through a supporting member 453. The second bar lighting part 452 is attached to the first pole 251 through a supporting member 454. In other words, the first bar lighting part 451 and the second bar lighting part 452 are respectively provided on the lateral portions of the medicine photographing device 200, specifically, provided on the lateral sides of the placing part 220. As shown in FIG. 5, the first bar lighting part 451 and the second bar lighting part 452 are provided in a direction parallel to the front-back direction of the medicine photographing device 200. A light emitting surface of each of the first bar lighting part 451 and the second bar lighting part 452 is directed toward the obliquely downward direction, more specifically, directed toward the placing part 220. A distance between a position of the placing part 220 at which the medicine is to be placed and each of the first bar lighting part 451 and the second bar lighting part 452 is larger than a distance between the position of the placing part 220 at which the medicine is to be placed and the first ring lighting part 431. Further, each of the first bar lighting part 451 and the second bar lighting part 452 is provided so that a distance between each of the first bar lighting part 451 and the second bar lighting part 452 and the lateral surface of the medicine photographing device 200 is smaller than a distance between the lower end of the inclined surface 231 of each of the guide members 230 and the lateral surface of the medicine photographing device 200 and a distance between the outer peripheral portion of the hole 222 of the tray supporting member 221 and the lateral surface of the medicine photographing device 200. By arranging the third light source 450 as described above, it is possible to ensure a more large space in the upper inner space 240. Thus, the user can easily place the tray 300 on the placing part 220.

Each of the first bar lighting part 451 and the second bar lighting part 452 includes a polarizing filter and is configured so that light diffused by passing this polarizing filter reaches to the medicine. Specifically, each of the first bar lighting part 451 and the second bar lighting part 452 is configured so that direct light emitted from each of the first bar lighting part 451 and the second bar lighting part 452 is cut by the polarizing filter and the light diffused by the polarizing filter passes through the hole 222 of the tray supporting member 221, that is passes through an inside of the ring of the first ring lighting part 431 to reach the medicine. Namely, the third light source 450 serves as a diffused light source or an indirect light source. With this configuration, an upper portion of the medicine is appropriately illuminated. The present inventors have found that it is possible to clearly photograph a print attached to the surface of the medicine by using the third light source 450 having the described configuration. In addition, it is possible to clearly photograph the print regardless of the condition that the medicine is a table or a capsule.

As shown in FIGS. 4 and 5, the fourth light source 460 which is the same kind as the third light source 450 is provided on the lower side of the second light source 440. The fourth light source 460 is constituted of a plurality of bar lighting part, specifically constituted of a third bar lighting part 461 and a fourth bar lighting part 462. The third bar lighting part 461 is attached to the third pole 253 through a supporting member 463. The fourth bar lighting part 462 is attached to the first pole 251 through a supporting member 464. In other words, the third bar lighting part 461 and the fourth bar lighting part 462 are respectively provided on the lateral portions of the medicine photographing device 200 as is the cases for the first bar lighting part 451 and the second bar lighting part 452. Further, the third bar lighting part 461 and the fourth bar lighting part 462 are provided in the direction parallel to the front-back direction of the medicine photographing device 200 as is the cases for the first bar lighting part 451 and the second bar lighting part 452. A light emitting surface of each of the third bar lighting part 461 and the fourth bar lighting part 462 is directed toward the obliquely upward direction, more specifically directed toward the placing part 220. As is the case for the relationship between the third light source 450 and the first light source 430, a distance between the placing part 220 and each of the third bar lighting part 461 and the fourth bar lighting part 462 is larger than a distance between the placing part 220 and the second ring lighting part 441. As is the cases for the first bar lighting part 451 and the second bar lighting part 452, each of the third bar lighting part 461 and the fourth bar lighting part 462 also includes a polarizing filter and is configured so that light diffused by passing this polarizing filter reaches to the medicine. Specifically, each of the third bar lighting part 461 and the fourth bar lighting part 462 is configured so that the diffused light from each of the third bar lighting part 461 and the fourth bar lighting part 462 passes through an inside of the ring of the second ring lighting part 441 to reach the medicine. With this configuration, a lower portion of the medicine is illuminated to make a print attached to the lower portion of the medicine clear.

In this embodiment, each of the third light source 450 and the fourth light source 460 is constituted of the two bar lighting parts, but each of the third light source 450 and the fourth light source 460 may be constituted of four bar lighting parts in other embodiments. In this case, it is preferable that the four bar lighting parts are arranged so as to form a rectangular shape and surround the placing part 220.

The first camera 410 is provided on the upper side of the first bar lighting part 451 and the second bar lighting part 452. The first camera 410 is attached to the second pole 252 through an attachment member 411. Due to the attachment member 411, the first camera 410 is positioned on the vertical upper side of the placing part 220 and fixed so as to be directed toward the placing part 220. When the medicine photographing device 200 is viewed from the upper side, a photographing area of the first camera 410 contains the hole 222 of the tray supporting member 221 and the inside of the ring of the first ring lighting part 431. With this configuration, the first camera 410 can appropriately photograph the upper surface of the medicine placed on the placing part 220, that is an image obtained by viewing the medicine from the directly upper side.

The second camera 420 is provided on the lower side of the third bar lighting part 461 and the fourth bar lighting part 462. The second camera 420 is attached to the second pole 252 through an attachment member 421. Due to the attachment member 421, the second camera 420 is positioned on the vertical lower side of the placing part 220 and fixed so as to be directed toward the placing part 220. When the medicine photographing device 200 is viewed from the lower side, a photographing area of the second camera 420 contains the inside of the ring of the second ring lighting part 441. With this configuration, the second camera 420 can appropriately photograph the lower surface of the medicine placed on the placing part 220, that is an image obtained by viewing the medicine from the lower side. Each of the first camera 410 and the second camera 420 described above can photograph a color image.

§2.3 Configuration of Placing Item

§2.3.1 First Embodiment of Placing Item

The tray 300 as show in FIG. 7A through FIG. 7C is used in the medicine photographing device 200 as a placing item for placing the medicine. The tray 300 has a configuration in which a hole 321 is formed in a main body 320 having a rectangular plate-like shape and a transparent cylinder 322 is fitted in this hole 321. The petri dish 310 as shown in FIG. 8 is set in the cylinder 322.

FIG. 8 shows the petri dish 310. A bottom portion 311 and a lateral surface 312 of the petri dish 310 are transparent. A non-transparent and planar ring 313 is provided on an outer marginal portion of the bottom portion 311. When the medicine is rolled toward the vicinity of an inner wall of the petri dish 310, illumination light is diffusely reflected by the medicine. This gives adverse effect on the photographing of the medicine in the vicinity of the inner wall of the petri dish 310. The ring 313 can appropriately prevent the medicine from being rolled toward the inner wall. In addition, the ring 313 can reduce unwanted reflection of the illumination light caused in the vicinity of a boundary between the bottom portion 311 and the inner wall of the petri dish 310. From a point of such view, it is preferable that the ring 313 has a block color. A width of the ring 313 is preferably in the range of about ½₀ to ½ times of a radius of the bottom portion 311 of the petri dish 310.

A capsule placing member 314 which is preferably made of a black-colored non-transparent material is provided on the bottom portion 311 of the petri dish 310. An about half portion of the bottom portion 311 of the petri dish 310 is occupied by the capsule placing member 314 and the transparent material forming the bottom portion 311 is exposed in a remaining about half portion of the bottom portion 311 of the petri dish 310. The portion whose transparent material is exposed in the bottom portion 311 is referred to as a transparent portion 315. It is recommended that the tablet is placed on the transparent portion 315. On the other hand, it is generally recommended that a capsule type medicine such as a capsule and a soft capsule is placed on the capsule placing member 314. The capsule placing member 314 has a planar shape approximate to a trapezoid shape. Specifically, the capsule placing member 314 has a long side and a short side in a longitudinal direction and two oblique sides each having the same length in a cross-sectional direction. A distance between the oblique sides decreases from the long side to the short side. By forming the capsule placing member 314 so as to have such a planar shape, it is possible to increase the number of capsule type medicines placed on the capsule placing member 314 per unit area. Further, the capsule placing member 314 has a portion whose upper surface forms a wave-like shape when the capsule placing member 314 is viewed from the lateral side. In other words, the capsule placing member 314 has grooved concave portions 316 and 317 on an upper surface thereof. A width and a depth of the concave portion 316 are adjusted so as to be larger than a width and a depth of the concave portion 317. Further, a length of the concave portion 316 is longer than a length of the concave portion 317. With this configuration, it becomes possible to easily place a relatively large capsule type medicine on the concave portion 316 and easily place a relatively small capsule type medicine on the concave portion 317. The capsule type medicine is placed on the concave portion 316 or 317 so that printed characters on the capsule type medicine is directed toward the upper side. Since the concave portion 316 or 317 prevents the capsule type medicine from being rolled, the first camera 410 can accurately photograph the printed characters on the capsule type medicine.

As described above, the tray 300 is placed on the tray supporting member 221 (see FIG. 6B). As shown in FIG. 7C, when the tray 300 is placed on the tray supporting member 221, the first ring lighting part 431 is positioned in the upper vicinity of the cylinder 322. In other words, the first ring lighting part 431 is positioned in the obliquely upward vicinity of the bottom portion 311 of the petri dish 310, that is in the vicinity of the bottom portion 311 and on the lateral side and the upper side of the bottom portion 311. The present inventors have found that it is possible to illuminate the medicine to more clearly photograph the engraved mark on the tablet by arranging the first ring lighting part 431 at such a position. In this regard, as shown in FIG. 6B, a height difference from the second ring lighting part 441 to the bottom portion 311 of the petri dish 310 is adjusted so as to be substantially equal to a height difference from the first ring lighting part 431 to the bottom portion 311 of the petri dish 310. From a point of such view, the height difference from the second ring lighting part 441 to the bottom portion 311 of the petri dish 310 is preferably in the range of about 0.5 to 2 times of the height difference from the first ring lighting part 431 to the bottom portion 311 of the petri dish 310.

§2.3.2 Second Embodiment of Placing Item

FIG. 27 is an exploded perspective view showing a second embodiment of the tray to be set in the medicine photographing device. As is the case for the tray 300, a tray 300' has a configuration in which a hole 321 is formed in a rectangular plate-like main body 320 and a transparent cylinder 322 is fitted in the hole 321. A big different point between the tray 300' and the tray 300 is a point that a circular transparent plate 330 is provided on a bottom portion of the cylinder 322 instead of the petri dish 310. By constituting the bottom portion of the cylinder 322 with the plate 330, it is possible to increase options for a constituent material forming the bottom portion of the cylinder 322. Thus, it becomes easier to select a material having the best compatibility with the camera or the lighting part, thereby more improving image quality of the photographed image of the medicine. A ring 313 is provided on an outer edge portion of the plate 330. An outer diameter of the ring 313 is substantially equal to a diameter of the plate 330. Further, a transparent second cylinder 331 is provided on the ring 313. More specifically, the second cylinder 331 is provided so that an outer peripheral portion of the second cylinder 331 makes contact with an inner peripheral portion of the cylinder 332. In another embodiment, the second cylinder 331 is directly provided on the outer edge portion of the plate 330. Then, the ring 313 is provided on the plate 330 so as to make contact with an inner wall of the second cylinder 331. Namely, the ring 313 is provided on the plate 330 in a state that the ring 313 is inserted into the second cylinder 331. Finally, the capsule placing member 314 is provided on the plate 330. By forming the placing item to be set in the medicine photographing device 200 with such a configuration, it is possible to more reduce diffused reflection of illumination light caused in the vicinity of a boundary between an outer edge portion of the plate 330 and the bottom portion of the second cylinder 331.

§3 Summary of Medicine Identifying Software

As shown in FIG. 1, the described medicine photographing device 200 is connected to the computer 500. The computer 500 contains the medicine identifying software 600 and the computer 500 controls operations of the medicine photographing device 200 by using the medicine identifying software 600. Specifically, the computer 500 controls the lighting parts in the medicine photographing device 200 and allows the cameras to photograph the medicine. Then, the computer 500 receives the photographed image of the medicine from the medicine photographing device 200. The computer 500 subjects the image data of the medicine to a variety of processes to obtain information required for narrowing the range of candidate medicines and searching the medicine. Then, the computer 500 narrows the range of the candidate medicines and searches the medicine based on this information to display this result on the screen 531 of the display device 530 as an identification result.

§3.1 Basic Operation Procedure

FIG. 9 shows the screen 531 in a state that the medicine identifying software 600 is activated. More specifically, the medicine identifying software 600 is called by a medication teaching assistant system 610 and a window 620 of a tablet identification menu is displayed on a right lower portion of the screen 531 by the medicine identifying software. Identification according to a purpose of the user is started from this window 620. As shown in FIG. 9, a "tablet image identify" item 621, a "returned tablet image identify" item 622 and a "magnifier" item 623 are displayed in the window 620. In the window 620, although the medicine identifying software 600 is named as "tablet identification", it is noted that the medicine identifying software 600 can identify not only the tablet but also the capsule type medicine. Further, in the example shown in FIG. 9, brought medicine identifying software is activated by other software, but the brought medicine identifying software may be singly activated and used by clicking an icon for the brought medicine identifying software, for example.

When the user selects the "tablet image identify" item 621, a "tablet image identification" window 700 is displayed on the screen 531 as shown in FIG. 10. A message 701 is displayed in the "tablet image identification" window 700. This message 701 urges the user to set the petri dish 310 in which one or more medicines have been supplied in the medicine photographing device 200 and select a "photograph" item 751. According to this message 701, the user supplies the one or more medicines to be identified into the petri dish 310 of the tray 300 and sets the tray 300 on the placing part 20 of the medicine photographing device 200. After the user sets the tray 300 in the medicine photographing device 200 and closes the cover 214 of the medicine photographing device 200, the user touches (in the case of inputting an instruction with the touch screen 532) or clicks (in the case of inputting an instruction with the mouse 542) the "photograph" item 751. In response to this operation, the medicine photographing device 200 photographs the image of the set medicines. As a result, a screen as shown in FIG. 11 is displayed in the "tablet image identification" window 700.

As shown in FIG. 11, the "tablet image identification" window 700 can be broadly separated into a first portion 710, a second portion 720, a third portion 730, a fourth portion 740, a first item displaying portion 750 and a second item displaying portion 760. The first portion 710 and the second portion 720 are arranged on the left side in the "tablet image identification" window 700. In an initial setting, a width of the first portion 710 is adjusted so as to be substantially equal to a width of the second portion 720. Further, the third portion 730 and the fourth portion 740 are arranged on the right side in the "tablet image identification" window 700. A width of the third portion 730 is adjusted so as to be substantially equal to a width of the fourth portion 740. The first item displaying portion 750 is provided on the lower side in the "tablet image identification" window 700. Further, the second item displaying portion 760 is provided on the lower side of the third portion 730. On the first item displaying portion 750 and the second item displaying portion 760, a variety of items which can be selected by the user are displayed.

An image of the petri dish 310 photographed by the medicine photographing device 200 is displayed on the first portion 710. As this image, an image photographed in a state that the first light source 430 or the second light source 440 is turned on is preferably used. This is because a contrast between the medicines and a background tends to be larger when the image is photographed under such illumination circumstance. An area containing a plurality of photographed medicines exists in this image. A "viewing from upper side" tab 711 and a "viewing from lower side" tab 712 are provided on the upper side in the first portion 710. When the user selects the "viewing from upper side" tab 711, an image obtained by photographing the medicines from the upper side is displayed on the first portion 710. When the user selects the "viewing from lower side" tab 712, an image obtained by photographing the medicines from the lower side is displayed on the first portion 710.

When the computer 500 obtains the image of the petri dish 310, the computer 500 automatically identifies an area occupied by each of the medicines based on this image. Then, the computer 500 automatically counts the number of the recognized medicines and allows a gauge portion 752 of the first item displaying portion 750 to display the resulting number of the medicines. Further, the computer 500 automatically identifies each of the recognized medicines one by one in the background. Then, the computer 500 allows the gauge portion 752 to display the number of the medicines whose automatic identification has been completed and a bar indicating how the identification of the medicines among all of the medicines in the petri dish 310 has been completed. As described above, in this embodiment, since a progress status of the identification is displayed with a graph, the user can understand how the identification progresses at one view. In this regard, the user can select a "stop" item 753 to forcibly stop the automatic identification by the computer 500.

As shown in FIG. 11, the computer 500 sequentially attaches the first mark 713, which indicates that the identification has been completed, to each of the medicines whose identification has been completed. For example, the first mark 713 is constituted of a solid line surrounding the medicine and this solid line is drawn with predetermined color (for example, red color). When the user selects one of the medicines displayed on the first portion 710 (in the example shown in FIG. 11, the user selects the medicine on the upper side), the "tablet image identification" window 700 is changed to a state as shown in FIG. 12. First, an enlarged image of the selected medicine is displayed on the second portion 720. An enlarged image obtained by photographing the selected medicine from the upper side is displayed on the upper side in the second portion 720 and an enlarged image obtained by photographing the selected medicine from the lower side is displayed on the lower side in the second portion 720. In order to reduce time and effort of the user, depending on the setting of the medicine identifying software 600, the computer 500 may automatically select one of the medicines whose identification has been completed.

As shown in FIG. 28, a size 721 of the medicine is displayed on the right lower side of the image of the medicine in the second portion 720. The size 721 is actually measured based on the image of the medicine by the medicine identifying software 600 and indicated with millimeters, for example. In the case where the medicine has a circular shape, the size of the medicine is a diameter of the medicine. In the case where the medicine has a non-circular shape, the size of the medicine is a length of a longitudinal axis of the medicine.

Referring back to FIG. 12, the second mark 714 is attached to the selected medicine on the first portion 710 so that the user or the computer 500 can recognize which medicine has been selected. A visual aspect of the second mark 714 is different from a visual aspect of the first mark 713. For example, the second mark 714 is constituted of a dotted line surrounding the medicine. Further, in order to emphasize which medicine has been selected, the second mark 714 may be displayed with an animation effect. For example, the dotted line surrounding the medicine may be rotated around the medicine. With this configuration, the user can easily understand that the medicine displayed on the second portion 720 corresponds to which medicine among the plurality of medicines displayed on the first portion 710. In this regard, the second mark 714 may be drawn with the same color as the first mark 713 (for example, red color) or a different color (for example, green color).

In the case where the identification for the selected medicine has been completed, the computer 500 allows the third portion 730 to display a list of candidate medicines obtained from an identification result. Each row of the list indicates information on one candidate medicine. In the initial setting, a medicine having higher possibility that the medicine is stochastically correct is displayed in an upper row in the list. Namely, in the list, the medicines are sorted in descending order from the upper side toward the lower side according to each possibility of correctness. A score obtained from a searching result is used as an indicator for indicating how the possibility of correctness of the medicine is high or low. Specifically, if the score of the matching possibility of a medicine hit through the search is high, possibility that the hit medicine is correct is high. Further, if the score of the matching possibility of the hit medicine is low, the possibility that the hit medicine is correct is low.

In each row of the list, the score of the possibility that the candidate medicine is correct, the image of the medicine stored in the database, the engraved mark or the printed code, a medicine name and the like are displayed from the left side to the right side in each row of the list as candidate medicine information. In this regard, by changing the setting, it is possible to display a rank of the possibility that the candidate medicine is correct among all of the candidate medicines instead of the score of the possibility of correctness of each candidate medicine. Further, it is also possible to display a code (for example, a YJ code) for identifying each candidate medicine in addition to the medicine name. As described above, when all of the information on one candidate medicine is simultaneously displayed in one row, the user can easily understand the information on the candidate medicine. Further, the size of each of the candidate medicines may be displayed in each row of the list.

The user may select a medicine whose identification has not been completed by the computer 500 from the medicines displayed on the first portion 710. For example, when the user selects a capsule displayed on the right lower side in the first portion 710, an enlarged image of the selected medicine is displayed on the second portion 720. However, since the identification for the selected medicine has not been completed by the computer 500, an identification result is not displayed on the third portion 730. Instead of the identification result, a message indicating that the selected medicine is being identified by the computer 500 is displayed on the third portion 730. As described above, in this embodiment, the user can select a medicine whose identification has not been completed. With this configuration, the user can immediately see an enlarged image of a medicine in which the user now has interest. This is convenient. On the other hand, the first mark 713 is attached to a medicine whose identification has been completed as shown in FIG. 11. Thus, the user can easily understand which medicine has been already identified when the user operates the medicine identifying software 600. Then, when the user selects the medicine whose identification has been completed, the user can immediately see the identification result by the computer 500 without wait time. Thus, the presence of the first mark 713 significantly contributes to reducing of working time of the user.

As shown in FIG. 13, when a mouse cursor 543 is moved into the vicinity of the image of the medicine listed in the list displayed on the third portion 730, an enlarged image of the medicine pointed by the mouse cursor 543 is displayed. By displaying an enlarged image of one of the plurality of medicines displayed on the third portion 730 responding to the operation of the user as described above, the user can immediately see details of the image of the medicine in which the user now has interest. Further, with this configuration, the user can easily compare the image of the medicine displayed on the second portion 720 with the image of the medicine displayed on the third portion. When the mouse cursor 543 is left from the enlarged image of the medicine, this enlargement for the image is canceled and the size of the image of the medicine changes back to an original size.

After that, the user visually compares the enlarged image of the medicine displayed on the second portion 720 with the information on each candidate medicine listed in the list displayed on the third portion 730 to select a medicine judged to be correct by the user. Specifically, the user selects one row, in which the information on the correct medicine is displayed, from the list displayed on the third portion 730. Although this matter is not shown in the drawings, when the user selects one row in which the information on the medicine is displayed, at least a part of the selected row is highlighted.

After that, when the user has a confidence that the medicine selected by oneself is a correct medicine, the user selects a "select" item 761. As a result, as shown in FIG. 14, the information on the selected medicine is added to the fourth portion 740. The added information, that is the information displayed in one added row is similar to the row selected in the third portion 730. Specifically, in the added row, the image of the medicine stored in the database, the engraved mark or the printed code, the medicine name and the number of the medicines are displayed. By using such a design, the user can easily understand which medicine is selected by oneself when the user again sees the information.

Further, in the case where there is a medicine obviously judged not to be a candidate medicine by the user in the candidate medicines listed in the list displayed on the third portion 730, the user selects a row in which information on such a medicine is displayed from the rows of the list on the third portion 730 and then selects a "non-target" item 763. By selecting the "non-target" item 763, the information on such a medicine is removed from the third portion 730. Then, information on a candidate medicine which is not listed in the list and has higher possibility of correctness next to the possibility of correctness of the candidate medicine listed at a last raw of the list is added to the third portion 730. If the user wants to search more information related to the medicine from the image of the medicine displayed on the second portion 720 or the information on the medicines displayed on the third portion 730, the user selects a "manual search" item 764. By selecting the "manual search" item 764, the user can manually search the information related to the medicine.

The third mark 715 is attached to the medicine in the first portion 710 corresponding to the medicine selected on the third portion 730 and displayed on the fourth portion 740. The third mark 715 attached to the medicine indicates that the selection and check operation to this medicine has been completed by the user. The third mark 715 has a visual aspect differing from the described visual aspect of the first mark 713. For example, the third mark 715 is constituted of a solid line surrounding the medicine and the solid line is drawn with a color (for example, blue color) differing from that of the first mark 713. Since the first mark 713 and the third mark 715 respectively have different visual aspects as described above, the user can understand which medicine has been already identified and which medicine has not been identified at one view, thereby improving work efficiency of the user. In particular, in the case where the color of the first mark 713 is different from the color of the third mark 715, the user can intuitively understand how the check operations for the medicines are completed at one view and thus the user can sensuously understand how much operations are needed for completing the identification operations for all of the medicines.

In the case where the user finds a mistake in own judgement with respect to the medicine selected by oneself and added to the fourth portion 740 and wants to cancel the selection to the medicine, the user selects the row, in which the information on the medicine to be removed is displayed, from the list displayed on the fourth portion 740 or the image of the medicine to be removed from the medicines displayed on the first portion 710. Then, the user selects a "selection cancel" item 762 in a state that the medicine is selected. By selecting the "selection cancel" item 762, the selected medicine is removed from the fourth portion 740. Further, the third mark 715 attached to the selected medicine is changed back to the first mark 713 or the second mark 714 on the first portion 710.

When the check operation for one medicine is completed, the user selects another medicine whose check operation has not been completed from the medicines displayed on the first portion 710 to subject the selected medicine to the check operation in the same manner as the above-described case. Depending on the setting of the medicine identifying software 600, when the check operation for one medicine is completed, the computer 500 automatically selects a subsequent medicine from the medicines whose identification has been completed. In this case, the user also subjects the selected medicine to the check operation in the same manner as the above-described case. When the user completes the check operations for all of the medicines as described above, the "tablet image identification" window 700 is changed to a state as shown in FIG. 15.

As shown in FIG. 15, when the user completes all of the selections for the medicines on the third portion 730 corresponding to all of the medicines displayed on the first portion 710 or when the computer 500 completes the automatic identification for all of the medicines (this depends on the setting), a "register" item 754, an "additionally photograph" item 755, a "re-photograph" item 756 and a "page turning" item 757 are additionally displayed on the first item displaying portion 750. When the user selects the "register" item 754, the identification operation for the medicine is completed. Namely, when the user selects the "register" item 754, the identification result is transmitted to the medication teaching assistant system 610 (see FIG. 9) and the "tablet image identification" window 700 is closed. In the case where the user wants to additionally identify another medicine, the user newly puts this medicine into the petri dish 310 to set this petri dish 310 in the medicine photographing device 200. Then, the user selects the "additionally photograph" item 755. By selecting the "additionally photograph" item 755, the additional medicine is photographed and the user can subject this medicine to the identification operation of medicine in the same manner as the above-described case. In the case where a plurality of image sets of the petri dish 310 are created as described above, the user can select the "page turning" item 757 to go back and forth among the plurality of image sets. In the case where the user wants to re-perform the identification for the medicine performed in this time, the user can select the "re-photograph" item 756 to re-start the identification for the medicine from the photographing of the image of the medicine. In the case where the user selects an "end" item 758, the identification operation of medicine is stopped and the "tablet image identification" window 700 is closed.

In another embodiment, as shown in FIG. 29, a "print" item 759 is further displayed on the first item displaying portion 750. When the user selects the "print" item 759, the identification result is printed as shown in FIG. 30. Examples of printed items include a title, time and date of the identification, an identification number of the medicine identifying apparatus, a patient name, a medicine serial number, a medicine name, an engraved mark (or a printed character), the number of medicines and a total number of medicines. Further, although this matter is not shown in FIG. 30, the printed items may contain a name of a pharmacist in charge, the photographed image and the image of the medicine stored in the database. Regarding the identification result, there are two cases. One of the cases is that it is necessary to write a detailed identification report for the identification result. The other of the cases is that it is only necessary to write a simple document for the identification result. The printed matter shown in FIG. 30, that is a journal print, is suitable for the latter case. Further, there is a case where the user wants to attach the identification result to a handwritten medical record. The journal print is suitable for this case, too.

When the medicine identifying software 600 transmits the identification result to the medication teaching assistant system 610 (see FIG. 9), the computer 500 may further transmit the number of the medicines and directions for use of the medicines to the medication teaching assistant system 610 in addition to the identification result. The number of the medicines is obtained through an after-mentioned "grouping" process. Further, the computer 500 may automatically group the medicines which are identified as the same kind through the identification and count the grouped medicines. The computer 500 may open a direction input window on the screen 531 to receive an input for the directions for use of the identified medicines from the user. In the medication teaching assistant system 610, the user often inputs the directions for use of the medicines. By allowing the user to use the medicine identifying software 600 to additionally input the directions for use of the medicines at the time of identifying the medicines, it is possible to improve convenience for inputting the directions for use of the medicines for the user.

In this regard, in the case where information for identifying the medicine is attached to a package containing the medicine, the medicine identifying software 600 may not perform the described image identification. For example, in the case where a barcode is attached to the package containing the medicine and the computer 500 can scan this barcode to identify the medicine packaged in the package, the medicine identifying software 600 may omit the described image identification and transmit the information on the medicine obtained by scanning the barcode to the medication teaching assistant system 610. By adding such a function to the medicine identifying software 600, it is possible to improve convenience for the user.

§3.2 Useful Functions

§3.2.1 Grouping

As shown in FIGS. 11 to 15, a "grouping" item 765 is displayed on the second item displaying portion 760 while the medicine identification operation is performed. When the user selects the "grouping" item 765, a "grouping" window 630 is opened on the screen 531 as shown in FIG. 16. The user can group a plurality of arbitrary medicines in the "grouping" window 630.

As shown in FIG. 16, the "grouping" window 630 is constituted of a first portion 631 and an item displaying portion 632. Enlarged images of the same images as the images displayed on the first portion 710 are displayed on the first portion 631. Specifically, the image obtained by photographing the petri dish 310 from the upper side and the image obtained by photographing the petri dish 310 from the lower side are displayed on the first portion 631 side by side.

The user touches or clicks a plurality of medicines judged as the same kind in the images displayed on the first portion 631 to select the medicines of the same kind. In another embodiment, the computer 500 judges whether or not the medicines displayed on the first portion 631 are the same kind with each other and then the computer 500 automatically selects medicines judged as the same kind. The process for judging whether or not the medicines are the same kind can be performed by subjecting each of the medicines displayed on the first portion 631 to an after-mentioned template matching process. A grouping mark 633 is attached to each of the medicines selected by the user or the computer 500. When the user selects the "grouping" item 634 in this state, the selected medicines are grouped. Namely, the selected medicines to which the grouping marks 633 are respectively attached are bundled to one group. When the user selects a "selection cancel" item 635, the selection to the medicines performed on the first portion 631 by the user is cancelled and the grouping marks 633 are removed from the medicines. Further, when the user selects a "grouping collectively cancel" item 636, all existing groups of the medicines are cancelled. Finally, the user selects a "decide" item 637, the grouping performed by the user is validated. Then, the "grouping" window 630 is closed and the previous "tablet image identification" window 700 is activated on the screen 531. In the activated "tablet image identification" window 700, the appropriate medicines have been grouped through the grouping performed by the user. In this regard, the user can select a "close" item 638 to cancel the operations for the grouping and return to the previous "tablet image identification" window 700.

In the case where a plurality of medicines are grouped as one group and medicines whose identification has been completed by the computer 500 and medicines whose identification has not been completed by the computer 500 simultaneously exist in the group, the computer 500 omits the identification for the medicines whose identification has not been completed. With this configuration, it is possible to reduce time required for allowing the computer 500 to identify all of the medicines. In the case where a plurality of medicines are grouped as one group and the user selects one of the grouped medicines on the third portion 730, the same selection is automatically applied to other medicines in the same group. Thus, it is possible to reduce time and effort of the input by the user and reduce operation time. As shown in FIG. 15, when the check operations with respect to the grouped medicines have been completed by the user and the medicines are added to the fourth portion 740, the number of the medicines belonging to the group is displayed. Further, "one" is displayed for a medicine which is not grouped.

§3.2.2 Automatic Learning

The medicine identifying software 600 has a function of automatically learning the identification result. More specifically, the computer 500 includes a learning database in the computer 500. The medicine identifying software 600 stores the medicine selected by the user (see FIG. 14) in the learning database. In the case where the same medicine as the medicine stored in the learning database is identified in next and succeeding times of the automatic identification by the computer 500, the computer 500 displays the medicine selected by the user in the previous time at the highest rank in the list of the third portion 730.

FIG. 31 shows details of the learning function of the computer 500. A basic concept of the learning function is described below. In the case where a medicine selected by the user from the list on the third portion 730 has been never selected by the user, the computer 500 stores the selection of the user in the learning database. In the case where the medicine selected by the user from the list on the third portion 730 has been already selected by the user one time, the computer 500 displays a message of "the user selected the same medicine with respect to this image of the medicine in the previous time. Please check whether or not this medicine is correct, once again." as shown in FIG. 32. In the case where the medicine selected by the user from the list on the third portion 730 has been already selected by the user two or more times, the computer 500 does not perform any process on the learning database because contents stored in the learning database have been checked by the user.

Hereinafter, description will be given based on a flowchart shown in FIG. 31. First, the computer 500 performs the automatic identification based on the image of each of the medicines (step S510). Then, as shown in FIG. 12, the computer 500 allows the third portion 730 to display the identification result in the form of list (step 520). At this time, in the case where the previous selecting result by the user is stored in the learning database, the medicine previously selected is displayed at a high rank in the list. Next, the user selects the correct medicine from the list of the candidate medicines displayed on the third portion 730 (step 530). Next, the computer 500 determines whether this selection by the user is the first time, the second time or the third or more time (step 540). In the case where the selection is the first time, that is in the case where the record of the selection for the candidate medicine selected by the user does not exist in the learning database, the computer 500 stores the selecting result of the candidate medicine by the user in the learning database (step 551) and adds the selected candidate medicine to the fourth portion 740 as shown in FIG. 14 (step 552). In the case where the selection is the second time, more specifically, in the case where a learning result for the medicine selected by the user is stored in the learning database and a user check completion flag is not on, the computer 500 displays a message 731 as shown in FIG. 32 (step 561). This message 731 indicates that this medicine is the medicine learned in the previous identification and urges the user to check whether or not this learning result is correct (step 562). Further, in the message 731, a name of the medicine selected by the user in the previous identification, an engraved mark (or a printed character), the photographed image of the medicine and the image of the medicine stored in the database are displayed. When the user selects a "Yes" item 732, the computer 500 sets the user check completion flag on with respect to the learning result for the medicine stored in the learning database (step S563). Further, the computer 500 adds the selected candidate medicine to the fourth portion 740 as shown in FIG. 14 (step 564). When the user selects a "No" item 733, the process returns to the step 530 and the computer 500 gives the user a chance for selecting another candidate medicine from the list of the candidate medicines displayed on the third portion 730 as shown in FIG. 12. Referring back to the step 540, in the case where the selection is the third time, more specifically, in the case where the learning result for the medicine selected by the user is stored in the learning database and the user check completion flag is on, the computer 500 adds the selected candidate medicine to the fourth portion 740 (step 571). With these procedures, even if the user mistakenly selected an incorrect medicine in the previous time, it is possible to reduce possibility that the user keeps selecting the incorrect medicine.

In another embodiment, it may be a setting matter of the user to allow the learning database to learn the candidate medicine selected by the user. For example, the computer 500 temporarily stores all of the selecting results for the candidate medicines by the user and then the user collectively re-checks the selecting results later (for example, after all of operations of a day have been finished) and picks up some of the selecting results as the selecting results of the candidates medicines which should be learned by the database to store only the picked-up selecting results in the learning database.

§3.2.3 Returned Tablet Image Identification

As shown in FIG. 9, a "returned tablet image identification" item 622 is provided in a window 620 of a tablet identification menu. When the user selects the "returned tablet image identification" item 622, a "returned tablet image identification" window 640 is displayed on the screen 531 as shown in FIG. 17. This returned tablet image identification is utilized in the case where all of a plurality of medicines to be identified are the same kind.

As shown in FIG. 17, the "returned tablet image identification" window 640 is constituted of a first portion 641, a second portion 642, a third portion 643, a count number and message displaying portion 644 and an item displaying portion 645. Functions and configurations of the first portion 641, the second portion 642 and the third portion 643 are respectively the same as the functions and the configurations of the first portion 710, the second portion 720 and the third portion 730 described above.

First, the user sets the petri dish 310 in which the medicines to be identified are supplied in the medicine photographing device 200 and then selects the "photograph" item 646. With this operation, the photographed image of the medicines is displayed on the first portion 641 as shown in FIG. 18. Further, the computer 500 automatically counts the number of the medicines to allow the count number and message displaying portion 644 to display the count number of the medicines. Furthermore, the computer 500 allows the count number and message displaying portion 644 to display a message 647. This message 647 urges the user to select one of the medicines displayed on the first portion 641. When the user selects one of the medicines displayed on the first portion 641, the display is changed to a state as shown in FIG. 19. Depending on the setting, the computer 500 automatically selects one of the medicines displayed on the first portion 641 as a representative medicine instead of the user.

When the one medicine is selected, the computer 500 subjects the medicine selected by the user or the computer 500 to the identification. Further, in order to make the medicine selected by the user or the computer 500 distinguishable on the first portion 641, a second mark 648 is attached to the selected medicine. After the automatic identification has been completed by the computer 500, the computer 500 allows the third portion 643 to display the information on the candidate medicines in the form of list. Further, the computer 500 allows the count number and message displaying portion 644 to display a message 649. This message 649 urges the user to select medicines judged to be correct by the user from the medicines displayed on the third portion 643 and select an "identification start" item 651. Further, in another embodiment, the user can select a "manual search" item 656 to manually search the medicine displayed on the second portion 642 as shown in FIG. 33. Then, the user can add a medicine found by the manual search to the list displayed on the third portion 643. With this configuration, the user can select medicines from medicines which are initially not displayed in the list on the third portion 643.

When the user selects the "manual search" item 656, a "manual search" window 680 is displayed on the screen 531 as shown in FIG. 41. The "manual search" window 680 is constituted of a search formula inputting portion 681, a searching result displaying portion 682, a database image displaying portion 683 and an item displaying portion 684. First, the user inputs a keyword or a search formula into a typing portion 685 of the search formula inputting portion 681. In this embodiment, the user can search the medicine based on the engraved mark or the medicine name. Next, the user pushes a search button 686 of the search formula inputting portion 681. As a result, a searching result by the computer 500 is displayed on the searching result displaying portion 682 in the form of list. When the user selects one of the medicines displayed in the list, the image of this medicine stored in the database is displayed on the database image displaying portion 683. When the user selects a "non-target" item 687 in a state that the medicine is selected on the searching result displaying portion 682, the selected medicine is deleted from the searching result displaying portion 682. When the user selects a "select" item 688, the selected medicine is added to the third portion 643 (see FIG. 22). When the user selects a "newly add" item 689, the selected medicine is added to the learning database (see §3.2.2). With this configuration, the medicine selected on the searching result displaying portion 682 will be always displayed on the third portion 643 as one of the candidate medicines from next identification. When the user selects an "end" item 691, the manual search is stopped and the "manual search" window 680 is closed.

Referring back to FIG. 19, when the user selects one of the medicines displayed on the third portion 643, the row in which the selected medicine is shown is highlighted as shown in FIG. 20. Further, a third mark 652, which indicates that the medicine has been checked by the user, is attached to the medicine on the first portion 641 corresponding to the selected medicine. When the user selects an "identification start" item 651 in this state, the computer 500 subjects each of the medicines which are not selected by the user, to the identification. If the identification results for all of the remaining medicines are the same as the identification results of the medicines which have been checked by the user, the "returned tablet image identification" is normally ended. When the user selects a "print" item 653 in this state, a counting result and a final result of the identification are printed. This printed matter contains a barcode (for example, a JAN code) for identifying each medicine. By scanning this barcode with a barcode reader, it is possible to immediately understand that the identified medicine should be returned to which tablet cassette.

In the case where it is found from the identification result that the remaining medicines include a medicine differing from the medicines which have been checked by the user, the computer 500 allows the count number and message displaying portion 644 to display a message of "a plurality of different medicines exist". In this case, the user removes the medicine judged to be different from the checked medicines from the petri dish 310 and then pushes a "rephotograph" button 654. Then, the user and the computer 500 repeat the same operations as the described operations. As a result, in the case where it is determined that all of the medicines contained in the photographed image are the same kind, the medicine identifying software can normally end the "returned tablet image identification". In this regard, when the user selects an "end" item 655, the user can end the "returned tablet image identification" even if the "returned tablet image identification" has not been completed.

FIG. 34 is a view showing a state that the user selects the "identification start" item 651 shown in FIG. 20. Namely, FIG. 34 is a screen when the computer 500 subjects each of the medicines, which are not selected by the user, to the identification. As shown in FIG. 34, the image of the medicine stored in the database, the medicine name, the engraved mark (or the printed character) and the number of the medicines are displayed on the second portion 642. An enlarged image of each of the medicines displayed on the first portion 641 is displayed on the third portion 643. The size of each of the medicines measured from the image of each of the medicines by the computer 500 is displayed on the lower right side of the image of each of the medicines. Detailed matters for displaying the size of each of the medicines are the same as the case described with reference to FIG. 28.

When the identification is completed, the "returned tablet image identification" window 640 is changed to a state as shown in FIG. 35. In the case where it is found from the identification results of all of the medicines that a medicine whose identification result is different from the identification result of the medicine selected by the user is found, that is in the case where it is found from the identification results of all of the medicines that a different kind of medicine exists, the computer 500 attaches fourth marks 657 and 658 to the medicine having the different identification result as shown in FIG. 35. More specifically, the computer 500 attaches the fourth mark 657 to the image of the medicine having the different identification result and displayed on the first portion 641. Further, the computer 500 attaches the fourth mark 658 to the image of the corresponding medicine displayed on the third portion 643. With this configuration, the user can easily understand that the different kind of medicine is mixed in the medicines being identified.

As shown in FIG. 35, the computer 500 further allows the third portion 643 to display a message 659. This message 659 urges the user to visually check all of the images of the medicines displayed on the third portion 643. In the case where the user finds a different kind of medicine from the result of visual checking, the user selects this different medicine. As a result, the fourth marks 657 and 658 are attached to this medicine, too. Further, in the case where the computer 500 judges that a medicine is a different kind but the user judges that the medicine is the same kind from the result of visual checking, the user can select this medicine to delete the fourth marks 657 and 658. Namely, the user can cancel the identification result by the computer 500 indicating that this medicine is a different kind.

When the user selects the "print" item 653 displayed on the item displaying portion 645, a message as shown in FIG. 36 is displayed on the screen. In the case where a medicine whose identification result is different is not found from the automatic identification result with respect to all of the medicines by the computer 500, a message as shown in FIG. 36(*a*) is displayed on the screen. When the user selects a "yes" icon, the identification result is printed. In the case of judging that a different kind of medicine is contained from the automatic identification result with respect to all of the medicines by the computer 500, a message as shown in FIG. 36(*b*) is displayed on the screen. Namely, the computer 500 sends the message to the user to indicate that it is found that a medicine whose identification result is different is contained and confirm whether or not the identification result should be printed. When the user selects a "yes" icon, the identification result containing the information on the different medicine is printed. Further, in the case where the user checks only the image obtained by photographing the medicine from the upper side and does not check the image obtained by photographing the medicine from the lower side, a message as shown in FIG. 36(*c*) is displayed on the screen and the identification result is not printed.

FIG. 38 is a view showing a second embodiment in a state that the identification has been completed in the "returned tablet image identification" window 640 shown in FIG. 34. As a result of the identification with respect to the medicines, a fifth mark 671 is attached to each medicine on the third portion 643 whose identification result is the same as the identification result of the medicine selected by the user (or the computer 500), that is the correct medicine on the third portion 643, as shown in FIG. 38. This fifth mark 671 is constituted of a solid line having blue color, for example. On the other hand, as the result of the identification, the fourth mark 658 is attached to the medicine whose identification result is different from the identification result of the medicine selected by the user or the like, that is the medicine whose identification result is different from the identification result of the medicine first selected by the user or the like. This fourth mark 658 is constituted of a solid line having red color, for example. By respectively attaching the different marks having the different color to the correct medicine and the different medicine as describe above, the user can understand which medicine is the different medicine at one view.

When the user selects one of the medicines displayed on the third portion 643, the mark attached to the selected medicine is changed to a second mark 673. Further, a second mark 674 is attached to the medicine on the first portion 641 corresponding to the medicine selected on the third portion 643, that is the medicine on the first portion 641 corresponding to the medicine to which the second mark 673 is attached. The second mark 673 has a different visual aspect from those of the fourth mark 658 and the fifth mark 671. For example, the second mark 673 is constituted of a dotted line surrounding the image of the medicine and this dotted line rotates around the image. More specifically, when the user selects the fourth mark 658 having red color, the second mark 673 is constituted of a red dotted line rotating around the image of the medicine. In response to this, the second mark 674 on the first portion 641 is constituted of a red dotted line rotating around the medicine. Further, in the case where the user selects the fifth mark 671 having blue color, the second mark 673 is constituted of a blue dotted line rotating around the image of the medicine. In response to this, the second mark 674 on the first portion 641 is constituted of a blue dotted line rotating around the medicine. Generally, in almost cases of the returned medicine identification, the medicines supplied into the petri dish 310 are the same kind. Thus, it is difficult to distinguish that the images of the medicines displayed on the third portion 643 respectively correspond to the medicines displayed on the first portion 641. Thus, by attaching the mark to only the medicine on the first portion 641 selected by the user, it becomes possible to easily understand that the medicine now checked by the user on the third portion 643 corresponds to which medicine in the petri dish 310. As a result, the user can easily remove the different medicine in the petri dish 310 with tweezers or the like with seeing the image on the first portion 641.

FIG. 39 is a view showing a third embodiment in a state that the identification has been completed in the "returned tablet image identification" window 640. As a result of the identification with respect to the medicines, the fifth mark 671 is attached to each medicine on the third portion 643 whose identification result is the same as the identification result of the medicine first selected by the user (or the computer 500), that is the correct medicine as shown in FIG. 39. In response to this, the fifth mark 672 is attached to the correct medicine on the first portion 641, that is the medicine on the first portion 641 corresponding to the medicine on the third portion 643 to which the fifth mark 671 is attached. On the other hand, referring back to the third portion 643, as the result of the identification, the fourth mark 658 is attached to the medicine whose identification result is different from the identification result of the medicine first selected by the user or the like, that is the medicine whose identification result is different from the identification result of the first medicine. In response to this, the fourth mark 657 is attached to the different medicine on the first portion 641, that is the medicine on the first portion 641 corresponding to the medicine on the third portion 643 to which the fourth mark 658 is attached.

The user sees the images of the medicines displayed on the third portion 643 to visually check whether or not each of the medicines displayed on the third portion 643 is actually correct one by one, that is whether or not each of the medicines displayed on the third portion 643 is the same as the medicine first selected by the user or the like one by one. Then, in the case where the medicine is judged as the correct medicine by the user from the result of visual checking, the user selects the judged medicine. As a result, a sixth mark 675 is attached to the image of the selected medicine. This sixth mark 675 indicates that the visual checking has been completed by the user and the medicine is judged as the correct medicine by the user. When the user selects a "remaining collectively OK" item 676 displayed on the item displaying portion 645, the sixth marks 675 are respectively attached to all of the medicines except the medicine to which the fourth mark 658 is attached. When the user selects a "front-back all switch" item 677, the front and back views of each of the images of the medicines displayed on the third portion 643 are switched. When the user checks the images of the medicines displayed on the third portion 643 one by one as described above to remove the different medicine from the petri dish 310 and attach the sixth marks 675 to all of the images of the medicines and the checks for all of the remaining medicines have been completed, the returned tablet image identification is ended.

FIG. 40 is a view showing a fourth embodiment in a state that the identification has been completed in the "returned tablet image identification" window 640 shown in FIG. 34. As shown in FIG. 40, the computer 500 automatically switches the front and back views of each of the medicines whose automatic identification has been completed so that the front and back views of each of the medicines become the same as the front and back views of the medicine first selected by the user or the like. Further, the computer 500 automatically rotates the medicines whose automatic identification has been completed one by one to align a direction of each of the medicines with a direction of the medicine first selected by the user or the like. The directions of the medicines can be aligned by rotating the images of the medicines to be identified so that the direction of each of the images of the medicines becomes the same as the direction of the image of the medicine first selected by the user or the like at the time of subjecting the medicines to be identified to the pattern matching process (see an after-mentioned step 380). Alternatively, since a master image collating the representative medicine (the medicine first selected by the user or the like) is an image correctly directed in the vertical direction, it may be possible to correct the vertical direction of the image of the representative medicine so as to coincide with the vertical direction of the master image when the image of the representative medicine is collated with the master image and correct the vertical direction of each of the images of the other medicines to be identified at the next or succeeding time when each of the images of the medicines is collated with the master image. At this time, in the case where a vertical direction of a medicine is not correctly displayed or the vertical direction of the medicine is not displayed in the same direction as the representative medicine, there is a high possibility that direction adjustment for this medicine is failed because this medicine is a different medicine. Thus, the user becomes likely to find such an image whose direction is different, thereby improving accuracy and efficiency of the visual identification operation. In this regard, the computer 500 can perform the automatic switching of the front and back views of the medicine by replacing the images of the front side and the back side of the medicine to be identified with each other in the case where the computer 500 judges that a pattern of the back side of the medicine to be identified coincides with a pattern of the front side of the medicine first selected by the user or the like from the result of the pattern matching process or in the case where the computer 500 judges that a pattern of the front side of the medicine to be identified coincides with a pattern of the back side of the medicine first selected by the user or the like from the result of the pattern matching process. With this configuration, the user can more easily perform the visual identification operation, thereby more improving the accuracy and safeness of the visual identification operation.

§3.2.4 Magnifier Function

As shown in FIG. 9, the "magnifier" item 623 is provided in the window 620 of the tablet identification menu. When the user selects the "magnifier" item 623, a "magnifier" window 660 is displayed on the screen 531 as shown in FIG. 21. The user can use a function of this "magnifier" window 660 to see an enlarged image of a medicine to be seen.

As shown in FIG. 21, the "magnifier" window 660 is constituted of a first portion 661 and an item displaying portion 662. An image obtained by photographing the placing part 220 (see FIG. 3) or the space 217 for the cutout portion (see FIGS. 4 and 5) nearest to the placing part 220 is displayed on the first portion 661. For example, in the case where the medicine is put into the tray 300 and the tray 300 is placed on the placing part 220, an enlarged image of an area containing the petri dish 310 is displayed on the first portion 661. Further, the user can insert the elongated packaging paper into the medicine photographing device 200 through the cutout portion 212 (see FIG. 2). In this case, an enlarged image of an area containing the packaging paper provided on just below the placing part 220 is displayed on the first portion 661, too. As shown in FIG. 21, one of an image obtained by photographing an object from the upper side and an image obtained by photographing the object from the lower side is selected by the user and the selected one is displayed on the first portion 661. When the user selects an "enlarge" item 663, the image of the object is zoomed in and an enlarged image of the object is displayed. On the other hand, when the user selects a "reduce" item 664, the image of the object is zoomed out and a reduced image of the object is displayed. Further, a current magnification ratio of the displayed image is displayed on the item displaying portion 662. Further, when the user selects a "lighting part switch" item 665, the medicine photographing device 200 switches the lighting part illuminating the medicine between the combination of the first light source 430 and the second light source 440 and the combination of the third light source 450 and the fourth light source 460. By illuminating the medicine with the first light source 430 and the second light source 440, it becomes easier to find the engraved mark formed on the medicine. By illuminating the medicine with the third light source 450 and the fourth light source 460, it becomes easier to find the print attached to the medicine. As described above, in this embodiment, the user can enlarge the image of the medicine to observe the engraved mark or the printed character of the medicine packaged in the packaging paper without unpacking the elongated packaging paper or taking the medicine from the packaging paper. Based on this observation, the user can manually search the medicine without taking the medicine from the packaging paper. In this regard, when the user selects an "end" item 666, the "magnifier" window 660 is closed.

§3.2.5 Identification for Medicine in Packaging Paper

As described above, the user can insert the elongated packaging paper into the medicine photographing device 200 through the cutout portion 212 (see FIG. 2). Then, the medicine photographing device 200 can photograph the medicine in the packaging paper. Then, the medicine identifying software 600 can identify the photographed medicine. Since the medicine identifying system 100 of this embodiment can identify the medicine in the packaging paper without breaking the packaging paper as described above, the medicine identifying system 100 is useful.

Some packaging paper has the image of the medicine printed on a back surface thereof as a sample picture for the medicine packaged in the packaging paper. The image of the medicine is stored in a medicinal product information database. In this case, the image of the medicine actually packaged in the packaging paper is displayed on an image obtained by photographing the packaging paper from the upper side as shown in FIG. 42. On the other hand, the sample picture of the medicine printed on the back surface of the packaging paper is displayed on an image obtained by photographing the packaging paper from the lower side. More specifically, when the user selects a "viewing from upper side" tab 711, the image obtained by photographing the packaging paper from the upper side is displayed on the first portion 710. When the user selects a "viewing from lower side" tab 712, the image obtained by photographing the packaging paper from the lower side is displayed on the third portion 730. Further, an enlarged image of the photographed image of the medicine actually packaged in the packaging paper is displayed on the upper side in the second portion 720. Furthermore, an enlarged image of a photographed image of the sample picture of the medicine printed on the back surface of the packaging paper is displayed on the lower side in the second portion 720. In this case, the medicine identifying software 600 separately subjects each of the images to the medicine identification in the background. As a result, two identification results are obtained in the medicine identifying software 600. Based on the identification results, a rank of a candidate medicine having high scores of the both identification is weighted. Namely, for the candidate medicine having the high scores of the both identification, the score of the candidate medicine is calculated by summing the scores of the both identification and further adding an additional point to the calculated score. As a result, the candidate medicine having the high scores of the both identification is displayed at a higher row of the list of the candidate medicines displayed on the third portion 730. As described above, in the case where the photographing image contains the two kinds of images, that is the actual photographed image of the medicine and the photographed image of the printed sample picture, the identification of the medicine is independently performed on the both images and then the list of the candidate medicines is created by combining the identification results, thereby improving accuracy of the identification. In particular, in the case where the sample picture is a color print (among color prints, a full-color print by an ink-jet printer is especially preferable), the accuracy of the identification is more improved.

§4 Medicine Identifying Algorithm

Hereinafter, description will be given to how the medicine identifying software 600 identifies each of the medicines in the image photographed by the medicine photographing device 200 in detail.

FIG. 22 shows a process at an upstream part of the medicine identification. First, when the user inputs an instruction for starting the medicine identification (step 110), the medicine photographing device 200 photographs the image of the medicines multiple times (step 120). Next, the computer 500 corrects the photographed image (step 130). Next, the computer 500 extracts areas in which the medicines exist from the corrected image (step S140). Then, the computer 500 separately subjects each of the extracted areas for each of the medicines to the identification (step 200).

<Step 110> User Input

The user first puts the medicines to be identified into the petri dish 310 of the tray 300 (see FIG. 7A through FIG. 7C). At this time, it is recommended that a tablet is directly placed on the transparent portion 315 of the bottom portion 311 of the petri dish 310 and a capsule is placed on the capsule placing member 314. Next, the user sets this tray 300 onto the placing part 220 of the medicine photographing device 200 and then closes the cover 214. Then, the user selects the "photograph" item 751 shown in FIG. 10.

<Step 120> Obtaining Medicine Image

When the computer 500 receives the input for photographing the medicines from the user, the computer 500 drives the medicine photographing device 200 to allow the medicine photographing device 200 to photograph the image of the petri dish 310. Specifically, the computer 500 obtains the following four images [Image 1] to [Image 4]. At this time, the computer 500 sets photographing conditions of the camera based on setting values (such as a focus of the camera, exposure time of the camera and gains for RGB) obtained from an after-mentioned "focus adjustment of the camera" and "calibration of lightness and color". With this configuration, reproducibility of image quality is improved.

[Image 1]

The image 1 is an image obtained by photographing the petri dish 310 from the upper side under the illumination light from the first light source 430. This image can be obtained by photographing the petri dish 310 with the first camera 410 in a state that the first ring lighting part 431 is turned on.

[Image 2]

The image 2 is an image obtained by photographing the petri dish 310 from the lower side under the illumination light from the second light source 440. This image can be obtained by photographing the petri dish 310 with the second camera 420 in a state that the second ring lighting part 441 is turned on.

[Image 3]

The image 3 is an image obtained by photographing the petri dish 310 from the upper side under the illumination light from the third light source 450. This image can be obtained by photographing the petri dish 310 with the first camera 410 in a state that the first bar lighting part 451 and the second bar lighting part 452 are turned on.

[Image 4]

The image 4 is an image obtained by photographing the petri dish 310 from the lower side under the illumination light from the fourth light source 460. This image can be obtained by photographing the petri dish 310 with the second camera 420 in a state that the third bar lighting part 461 and the fourth bar lighting part 462 are turned on.

<Step 130> Image Correction

As described later, calibration is preliminarily performed in the medicine identifying system 100 and the computer 500 stores correction information from this calibration as data. The computer 500 corrects the photographed images based on this correction information. Specifically, the computer 500 corrects a coordinate of each of the photographed images based on the correction information. With this configuration, a coordinate axis of each of the images photographed by the first camera 410 coincides with a coordinate axis of each of the images photographed by the second camera 420.

<Step 140> Extracting Medicine Area

After the image correction, the areas respectively occupied by the medicines are extracted from the images. For this purpose, the [Image 1] and the [Image 2] tending to have a big contrast between the background and each of the medicines are preferably used. This area extracting is performed by binarizing lightness of each pixel with a threshold value (if the lightness is smaller than the threshold value, the pixel is judged as a pixel of the background, and if lightness is equal to or larger than the threshold value, the pixel is judged as a pixel of each of the medicines) to separate areas equal to or larger than the threshold value.

FIG. 23 shows a flow of a medicine individual identification process (step 200). The following process is individually performed on each of the medicines. First, the computer 500 associates an occupied area of one medicine in the photographed image from the upper side with an occupied area of this medicine in the photographed image from the lower side (step 210). Next, the computer 500 determines whether this medicine is a tablet or a capsule (step 220). In the case of determining that this medicine is the tablet, the computer 500 performs a tablet identifying process (step 300). In the case of determining that the medicine is the capsule, the computer 500 performs a capsule identifying process (step 400).

<Step 210> Associating Medicines in Upper and Lower Images

A medicine directly placed on the transparent portion 315 of the petri dish 310 is shown in both of the images photographed from the upper side (the [Image 1] and the [Image 3]) and the images photographed from the lower side (the [Image 2] and the [Image 4]). At this step, an area occupied by one medicine in each of the images photographed from the upper side is associated with an area occupied by this medicine in each of the images photographed from the lower side. Specifically, when one of the images [Image 1] and [Image 2] corrected at the step 130 is horizontally or vertically inverted, the area occupied by the medicine in the one of the images substantially matches the area occupied by the same medicine in the other of the images. This matching area is an area occupied by the one medicine in each of the two images. Namely, each of the area in the non-inverted image and the area in the image obtained by cancelling the inverting of the image (this area in the later image corresponds to the area in the inverted image overlapping with the area in the non-inverted image) is an area corresponding to the one medicine in each of the tow images. At this time, it may possible to define an overlapping area, which is caused when one of the two images is inverted and the inverted image and the non-inverted image are overlapped with each other, as a corresponding area.

<Step 220> Tablet and Capsule Determination

After the computer 500 performs the associating process for the medicine area, the computer 500 determines whether or not this medicine is the tablet or the capsule. Since the tablet is placed on the transparent portion 315 of the petri dish 310, an upper surface of the tablet is shown in the images photographed from the upper side and a lower surface of the tablet is shown in the images photographed from the lower side. Namely, when the two images (the [Image 1] and the [Image 2]) are compared with each other, the areas corresponding to the medicine respectively exist in the image photographed from the upper side and the image photographed from the lower side in the case where the medicine is the tablet. Thus, in the case where the association for one area can be performed with respect to the two images at the step 210, namely, in the case where the area occupied by the medicine identified in the image photographed from the upper side is associated with the area occupied by the medicine identified in the image photographed from the lower side, the medicine is determined to be the tablet.

On the other hand, the capsule is placed on the non-transparent capsule placing member 314. Thus, although an upper surface of the capsule is shown in the images photographed from the upper side, the capsule is not shown in the images photographed from the lower side. Namely, when the two images (the [Image 1] and the [Image 2]) are compared with each other, the area occupied by the medicine exists in the image photographed from the upper side and the area occupied by the medicine does not exist in the image photographed from the lower side in the case where the medicine is the capsule. Thus, in the case where the association for one area cannot be performed with respect to the two images at the step 210, namely, in the case where an area corresponding to the area occupied by the medicine identified in the image photographed from the upper side is not identified in the image photographed from the lower side, the medicine is determined to be the capsule.

<Step 300> Tablet Identification

In the case where one medicine selected by the computer 500 is determined to be the tablet, the process shifts to a tablet identification process 300. FIG. 24 shows each process in the tablet identification process 300. First, the computer 500 determines whether or not the medicine has a circular shape (step 310). Next, the computer 500 performs an extracting process for an engraved mark formed on the surface of the medicine (step 320). Next, the computer 500 performs an extracting process for a print attached to the surface of the medicine (step 350). Next, the computer 500 determines whether or not the information attached to the surface of the medicine is the engraved mark or the print (step 340). Next, the computer 500 extracts a secant line attached to the surface of the medicine (step 350). Next, the computer 500 extracts representative color of the medicine (step 360). After that, the computer 500 narrows the range of the candidate medicines based on narrowing information related to the medicine (step 370). Finally, the computer 500 performs the template matching process based on the information on the engraved mark and/or the print extracted from the image of the medicine to perform a final search (step 380).

<Step 310> Circle Determination

The computer 500 calculates a degree of circularity of the area occupied by the medicine. In the case where the degree of circularity is equal to or more than a predetermined value, the computer 500 determines that the medicine has the circle shape. In the case where the degree of circularity is less than the predetermined value, the computer 500 determines that the medicine has a non-circular shape. In the case of determining that the medicine has the circular shape, the computer 500 calculates a central position and a radius of the circle. In the case of determining that the medicine has the non-circular shape, the computer 500 rotates the area occupied by the medicine so that a longitudinal axis of the area occupied by the medicine is parallel to the X-axis and a short axis of the area occupied by the medicine is parallel to the Y-axis. Further, the computer 500 calculates lengths of a longitudinal axis and a short axis of the medicine and a ratio of the lengths of the longitudinal axis and the short axis of the medicine.

<Step 320> Engraved Mark Extraction

Figure 43:
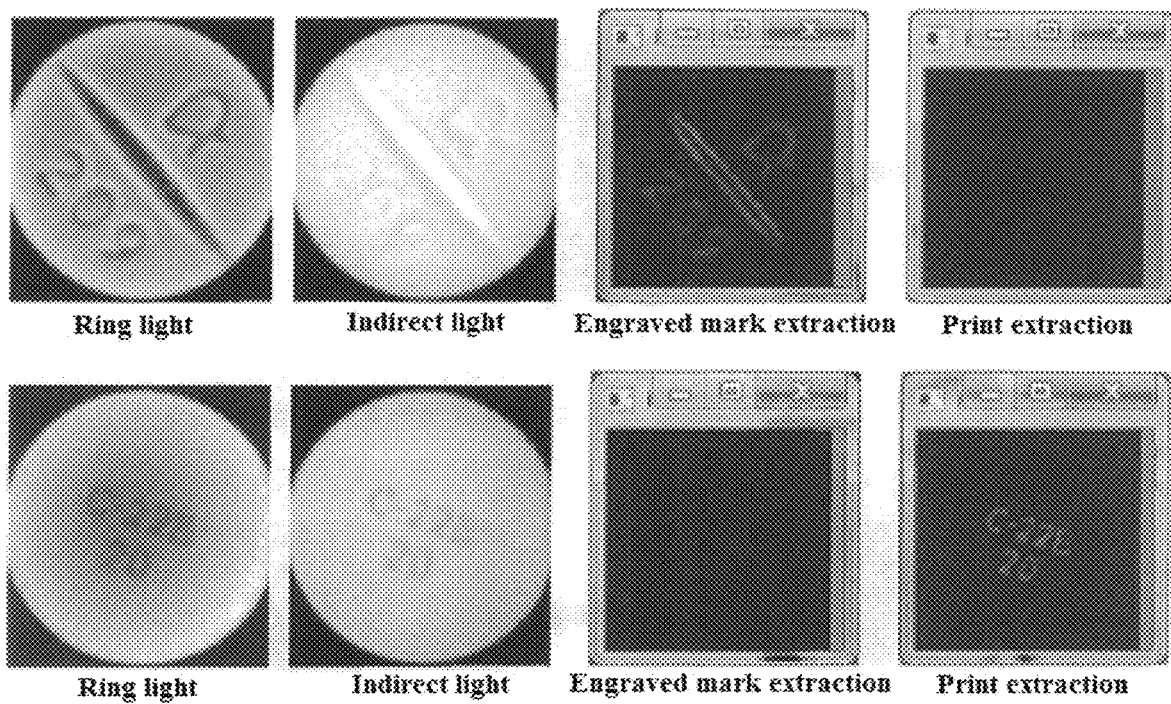

The computer 500 subjects the [Image 1] and the [Image 2], that is the images respectively photographed under the illumination by the first light source 430 and the second light source 440 to the extracting process for the engraved mark. The present inventors have found that it is possible to photograph an image of the medicine in which the engraved mark is emphasized by photographing the medicine under the illumination by the first light source 430 and the second light source 440 (see FIG. 43).

<Step 330> Print Extraction

The computer 500 subjects the [Image 3] and the [Image 4], that is the images respectively photographed under the illumination by the third light source 450 and the fourth light source 460 to the extracting process for the print. The present inventors have found that it is possible to photograph an image of the medicine in which the print is emphasized by photographing the medicine under the illumination by the third light source 450 and the fourth light source 460 (see FIG. 43).

<Step 340> Engraved Mark and Print Determination

As described above, when the extracting process for the engraved mark (step 320) is subjected to the images respectively photographed under the illumination by the first ring lighting part 431 and the second ring lighting part 441, images in which the engraved mark formed on the surface of the medicine is appropriately extracted can be obtained. Further, when the extracting process for the print (step 330) is subjected to the images respectively photographed under the illumination by the first bar lighting part 451, the second bar lighting part 452, the third bar lighting part 461 and the fourth bar lighting part 462, images in which the print attached to the surface of the medicine is appropriately extracted can be obtained (see the above image samples). The computer 500 determines whether or not the information attached to the surface of the medicine is the engraved mark or the print, that is whether or not the engraved mark and the print are attached to the surface of the medicine based on these engraved mark extracted images and print extracted images.

In order to determine whether or not the engraved mark is formed on the medicine, the computer 500 first binarizes the engraved mark extracted image obtained at the step 320 with utilizing a predetermined threshold value as a criterion for the binarization. Next, the computer 500 uses this binarized image as a mask to take an average value between the mask and the engraved mark extracted image. In the case where the average value is equal to or more than a threshold value, the computer 500 determines that the engraved mark is attached to the medicine. In the case where the average value is less than the threshold value, the computer 500 determines that the engraved mark is not attached to the medicine. In the same manner, in order to determine whether or not the print is attached to the medicine, the computer 500 first binarizes the print extracted image obtained at the step 330 with utilizing a predetermined threshold value as a criterion for the binarization. Next, the computer 500 uses this binarized image as a mask to take an average value between the mask and the print extracted image. In the case where the average value is equal to or more than a threshold value, the computer 500 determines that the print is attached to the medicine. In the case where the average value is less than the threshold value, the computer 500 determines that the print is not attached to the medicine.

<Step 350> Secant Line Extraction

The computer 500 subjects the engraved mark extracted image obtained at the step 320 to a secant line extracting process. Specifically, the computer 500 determines whether or not the secant line exists on the medicine. In the case of determining that the secant line exists on the medicine, the computer 500 separates the image of the medicine into an area in which the secant line exists and another area.

<Step 360> Representative Color Extraction

Next, the computer 500 separately extracts representative color of the medicine in the area in which the engraved mark or the print exists and representative color of the medicine in the other area. This representative color extraction can be appropriately performed by clustering color constituting each pixel. Further, in another embodiment, determination for color strength of "white color", "light color" and "dark color" is performed on the image of the medicine or the area in which the engraved mark or the print exists and the other area instead of extracting the representative color. This determination can be performed by determining that the color strength is determined to be "dark color" if the color in the area is less than a first threshold value, the color strength is determined to be "light color" if the color in the area is equal to or more than the first threshold value and less than a second threshold value and the color strength is determined to be "white" if the color in the area is equal to or more than the second threshold value.

<Step 370> Narrowing

The computer 500 accesses the database. Then, the computer 500 searches medicines to be the candidate medicines based on the data obtained through the above steps. As a first stage, the computer 500 first narrows the range of medicines to be searched. Specifically, the computer 500 narrows the range of the medicines to be searched based on at least one of the kind of the medicine (whether or not the medicine is the tablet or the other than the tablet), the shape of the medicine (whether or not the medicine has the circular shape or the non-circular shape, and the ratio of the lengths of the longitudinal axis and the short axis in the case where the medicine has the non-circular shape), the size of the medicine (the diameter of the medicine in the case where the medicine has the circular shape, and the lengths of the longitudinal axis and the length of the short axis in the case where the medicine has the non-circular shape), the presence/absence of the engraved mark, the presence/absence of the print, the presence/absence of the secant line and the representative color of the medicine (the representative color in the area in which the engraved mark exists, the representative color in the area in which the print exists and the representative color in the other area). In this regard, in the case where the computer 500 can access a prescription history (for example, data of a medicine notebook) of the patient, the computer 500 may limit the range of the medicine to be searched to the medicines contained in the prescription history. For example, in the case where the computer 500 can access the data of the medicine notebook stored in a smartphone of the patient, the computer 500 accesses the data of the medicine notebook to obtain information on the medicines previously prescribed to the patient. Further, in the case where the medicine notebook printed on paper exists, the computer 500 can scan the medicine notebook to convert the information of the medicine notebook into text data with an OCR (Optical Character Recognition) and narrows the range of the medicines to be searched based on this text data. With this configuration, it is possible to improve speed of the medicine search.

<Step 380> Template Matching Process

After that, the template matching process (sometimes referred to as a pattern matching process) is performed between the engraved mark extracted image and/or the print extracted image obtained in the described step and an engraved mark template image and/or a print template image for each medicine stored in the database to pick up medicines having high possibility of matching the medicine to be identified. In the case where the tablet has the circular shape, the area occupied by the medicine in the image is moved and corrected so that a center of the circle coincides with a center of the image prior to the template matching process. In another embodiment, the extracted image and the template image may be corrected so that a centroid of the engraved mark and/or the print coincides with the center of the image. Further, in the case where the tablet has the circle shape, the extracted image and the template image are rotated so that a result of the template matching process is maximized. After that, the both images are subjected to the template matching process to calculate a score. This score indicates a numerical value representing a degree of matching between the both images. In the case where the score of the template matching process is equal to or more than a predetermined value or in the case where the score of the template matching process is within a predetermined range of ranks from the highest rank, the computer 500 picks up a medicine to which the template image belongs as one of the candidate medicines. In the case where the tablet has the secant line, both of the template matching process in a state that the secant line exists and the template matching process in a state that the secant line is removed may be performed. Further, in the case where the print or the engraved mark is constituted of words, the computer 500 may perform the template matching process with utilizing each word as one unit or divide the words into characters, numerical numbers and symbols to subject the characters, the numerical numbers and the symbols to the template matching process. Furthermore, the computer 500 may extract text information from the image of the engraved mark or the print with the OCR to perform the template matching process based on this text information.

<Step 400> Capsule Identification

Referring back to the step 220 in FIG. 23, in the case where the one medicine selected by the computer 500 is determined to be the capsule, the process shifts to a capsule identifying process 400. FIG. 25 shows each process in the capsule identifying process 400. First, the computer 500 divides the image of the capsule into two areas (step 410). Next, the computer 500 extracts representative color of each area from the two areas (step 420). Next, the computer 500 performs the extracting process for the print attached to the surface of the medicine from the two areas (step 430). Next, the computer 500 determines whether or not the print is attached to the surface of the medicine (step 440). After that, the computer 500 narrows the range of medicines to be the candidate medicines based on narrowing information related to the medicine (step 450). Finally, the computer 500 performs the template matching process based on the information on the print extracted from the image of the medicine to perform a final search (step 460).

<Step 410> Area Division

First, the computer 500 divides the image of the medicine into the two areas. Specifically, the computer 500 clusters color information of the image of the medicine, specifically, clusters color of each pixel. Next, the computer 500 groups the clustered color information to define areas to which this color group belongs as one area. With this configuration, the capsule whose color of a right side half and color of a left side half are different from each other is appropriately divided into the two areas.

<Step 420> Representative Color Extraction

Next, the computer 500 extracts the representative color of each area of the medicine. This extraction can be appropriately performed by clustering the color information of each pixel constituting each area.

<Step 430> Print Extraction

The computer 500 subjects each area divided at the step 410 to the same process as that of the step 330 to extract the print from each area. The present inventors have found that it is possible to appropriately extract the print from the capsule by dividing the image of the capsule into the two areas and separately subjecting the two images to the extracting process for the print image.

<Step 440> Print Determination

The computer 500 subjects each divided area of the medicine to the same process as that of the step 340 to determine whether or not the print is attached to each area.

<Step 450> Narrowing

The computer 500 narrows the range of the medicines to be the candidate medicines in the same manner as the step 360. Specifically, the computer 500 narrows the range of the medicines to be searched based on at least one of the kind of the medicine (whether or not the medicine is the tablet or the other than the tablet), the shape of the medicine (the ratio of the lengths of the longitudinal axis and the short axis of the medicine), the size of the medicine (the lengths of the longitudinal axis of the medicine and the length of the short axis of the medicine), the representative color of each areas and the presence/absence of the print in each area to which the representative color belongs.

<Step 460> Template Matching Process

The computer 500 cuts a printed portion from the print extracted image (input image) obtained at the step 430. Next, the computer 500 subjects each area of the print extracted image divided at the step 410 to the template matching process in the same manner as the step 370 to pick up the candidate medicines.

§5 Additional Process of Medicine Identifying Software

§5.1 Additional Process at <Step 370>

At the described step 370, it is assumed that the database accessed by the computer 500 stores the template image corresponding to the engrave mark extracted image and/or the print extracted image. However, depending on the cases, only a simple picture of the medicine is stored in the database. In this case, the computer 500 may obtain an area of the medicine from this image data and subject the area of the medicine to the print extraction and the engraved mark extraction in the same manner as the above case to use the obtained print extracted image and the obtained engraved mark extracted image as the template images. Further, with this method, it is also possible to create the template image to be stored in the database. In this regard, the area of the medicine can be obtained from the image data as described below. First, background color is obtained and a portion other than the background color and characters is determined to be an area occupied by the medicine. In this regard, in the case where one, three or more of areas are found, this determination is considered as an error. Next, a position of a centroid of each area is calculated and a left side and a right side of the medicine are determined based on the positions of the centroids.

§5.2 Calibration of Camera

In order to appropriately practice the above embodiments, it is required that the first camera 410 and the second camera 420 should be in focus. Further, it is required that the photographing area of the first camera 410 should coincide with the photographing area of the second camera 420. Furthermore, it is required that the lightness and the color of the photographed image should be respectively within predetermined value ranges. Thus, before shipping the medicine identifying system 100 to a factory or at the time of setting up the medicine identifying system 100 in a delivery destination, calibration as described below is performed. In this regard, once this calibration has been performed, it is normally unnecessary to again perform the same calibration.

§5.2.1 Positioning of Camera

In this calibration, positioning of camera is first performed. First, the tray 300 is set on the placing part 220 of the medicine photographing device 200 in a state that the petri dish 310 is set on the tray 300. Next, the petri dish 310 is photographed by the first camera 410 to allow the display device 530 of the computer 500 to display this photographed image. At this time, a virtual image having a cross mark at a predetermined position is displayed on the image of the petri dish 310. Then, a position and an angle of the first camera 410 are slightly adjusted so that this cross mark is positioned in the petri dish 310. The same operation is performed on the second camera 420.

§5.2.2 Focus Adjustment of Camera

Next, focus adjustment of the camera is performed. First, a template on which a predetermined character, symbol or figure is drawn is set on the placing part 220 of the medicine photographing device 200 and the template is photographed with a low magnification. Then, the focus of the camera is roughly adjusted so that the contents of the template become most clear in the photographed image. After that, the same operation is performed in a state that the magnification is increased to slightly adjust the focus of the camera.

§5.2.3 Calibration of Photographing Area

Due to this calibration, it becomes possible to match coordinates of the photographing areas of the upper and lower cameras with each other. Further, it is also possible to obtain resolution of the camera. First, a calibration sheet 810, which is a calibration tool, as shown in FIG. 26A and FIG. 26B is prepared. In a configuration of this calibration sheet 810, black circles each having a predetermined size are arranged in a matrix pattern of m×n spaced apart from each other by a predetermined distance (in the example shown in FIG. 23, a matrix pattern of 3×4) on both surfaces of a plate or a sheet having a predetermined thickness. Further, positions and the sizes of the black circles on a front surface of the calibration sheet 810 are the same as those on a back surface of the calibration sheet 810. At the time of the calibration, the calibration sheet 810 is set on the placing part 220 of the medicine photographing device 200 and the calibration sheet 810 is photographed by the first camera 410 and the second camera 420. Next, a transformation matrix for converting the image so that the black circles in the images are respectively positioned at designated coordinates and the size of each of the black circles becomes a predetermined size is calculated. This calculation is performed on the image obtained by photographing the calibration sheet 810 from the upper image and the image obtained by photographing the calibration sheet 810 from the lower image. At the described step 130, the photographed image of the petri dish 310 is corrected based on this transform matrix. With this configuration, it is possible to match a coordinate position of the image obtained by photographing the petri dish 310 from the upper side with a coordinate position of the image obtained by photographing the petri dish 310 from the lower side. Further, from the transform matrix, it is possible to obtain DPI (Dots Per Inch) of the image, that is the number of pixels constituting a unit length of the image.

§5.2.4 Calibration of Lightness and Color

Due to this calibration, it is possible to improve reproducibility of color of the photographed image. The following steps (a) and (b) are repeatedly performed in a state that the calibration sheet 810 is placed on the placing part 220 in the same manner as the above case.

(a) Adjustment of exposure: the photographing by the first camera 410 is performed for predetermined exposure time in a state that the first light source 430 is turned on. Further, the photographing by the second camera 420 is performed for predetermined exposure time in a state that the second light source 440 is turned on. Next, lightness of each predetermined point of the photographed image is calculated. In the case where this lightness is higher than a target value, the exposure time of each camera is decreased. In the case where the lightness is lower than the target value, the exposure time of each camera is increased.

(b) Adjustment of color (white balance): RGB values of each predetermined point of the photographed image are calculated. In the case where the value of B (blue color) is larger than the value of R (red color), a gain for the R is increased. In the case where the value of B is smaller than the value of R, the gain for the R is decreased. In the case where the value of B is larger than the value of G (green color), a gain for the G is increased. In the case where the value of B is smaller than the value of G, the gain for the G is decreased.

Until the values respectively reach the target values, the above steps (a) and (b) are repeatedly performed. Through these steps, setting values of each camera at the time of photographing can be obtained. Further, the same operation is performed with the combination of the third light source 450 and the first camera 410 and the combination of the fourth light source 460 and the second camera 420.

FIG. 37A and FIG. 37B show a second embodiment of the calibration sheet. This calibration sheet 810' has a configuration in which black circles 811 each having a predetermined size are arranged in a matrix pattern of m×n spaced apart from each other by a predetermined distance on both surfaces of a circular plate or a circular sheet having a predetermined thickness. Further, in the configuration of the calibration sheet 810', lines 812 each having a predetermined length are arranged in the vicinity of an outer peripheral portion of the calibration sheet 810' on four directions (right, left, upper and lower directions) at regular angular intervals of 90° so that two pairs of lines 812 are respectively positioned on two center lines of the circle. More specifically, one pair of lines 812 is arranged parallel to a row direction of the circles 811 and on an extending direction of the circles 811 arranged in the row direction. The other pair of lines 812 are arranged parallel to a column direction of the circles 811 and on an extending direction of the circles 811 arranged in the column direction. The configuration of the calibration sheet 810' except for the above matters is the same as the configuration of the calibration sheet 810. A diameter of this calibration sheet 810' is substantially equal to the inner diameter of the ring 313 to be placed on the plate 330 (see FIG. 27) or the petri dish 310 (see FIG. 8). In other words, a planar shape of the calibration sheet 810' corresponds to the shape of the bottom surface of the placing item for placing the medicine. By using the calibration sheet 810', it is possible to appropriately prevent a position of the calibration sheet 810' from being shifted when the placing item is set on the placing part 220 of the medicine photographing device 200 after the calibration sheet 810' has been placed on the placing item. Further, by using the lines 812 as indicators, it becomes easier to align directions of the circles 811 to a predetermined direction.

What is claimed is:

1. A medicine photographing device for photographing an image of a medicine, comprising:
   a placing part on which the medicine is to be placed;
   a first camera provided on an upper side of the placing part;
   a second camera provided on a lower side of the placing part;
   an upper light source provided on the upper side of the placing part; and
   a lower light source provided on the lower side of the placing part;
   a placing item consisting of a transparent bottom and a wall provided around the bottom is set in the placing part;
   a non-transparent ring provided on the vicinity of an inner wall in the bottom of the placing item and configured to prevent the medicine from being rolled toward the inner wall so as to reduce diffuse reflection of illumination light on the medicine caused by the inner wall.

2. The medicine photographing device according to claim 1, wherein the upper light source includes a first light source provided on the upper side of the placing part,
   the lower light source includes a second light source which is the same kind as the first light source and provided on the lower side of the placing part,
   the upper light source further includes a third light source which is a different kind from the first light source and provided on the upper side of the placing part, and
   the lower light source further includes a fourth light source which is the same kind as the third light source and provided on the lower side of the placing part.

3. The medicine photographing device according to claim 2, wherein the first light source and/or the second light source are used for photographing an engraved mark of the medicine, and
   the third light source and/or the fourth light source are used for photographing a print of the medicine.

4. The medicine photographing device according to claim 2, wherein a distance from each of the third light source and the fourth light source to the placing part is larger than a distance from each of the first light source and the second light source to the placing part.

5. The medicine photographing device according to claim 2, wherein each of the first light source and the second light source is a direct light source, and
   each of the third light source and the fourth light source is a diffused light source.

6. The medicine photographing device according to claim 2, wherein each of the third light source and the fourth light source includes a polarizing filter and is configured so that light passing through the polarizing filter reaches to the medicine.

7. The medicine photographing device according to claim 2, wherein the first light source is constituted of a first ring lighting part,
   light from the third light source passes through an inside of a ring of the first ring lighting part and then reaches to the medicine,
   the second light source is constituted of a second ring lighting part, and
   light from the fourth light source passes through an inside of a ring of the second ring lighting part and then reaches to the medicine.

8. The medicine photographing device according to claim 2, wherein the third light source is provided at a position which is lower than the first camera and lateral to the placing part, and
   the fourth light source is provided at a position which is higher than the second camera and lateral to the placing part.

9. The medicine photographing device according to claim 1, wherein the upper light source includes a first ring lighting part,
   when the placing part is viewed from an upper side, a photographing area of the first camera contains an inside of a ring of the first ring lighting part,
   the lower light source includes a second ring lighting part, and
   when the placing part is viewed from a lower side, a photographing area of the second camera contains an inside of a ring of the second ring lighting part.

10. The medicine photographing device according to claim 9, wherein a placing item including a transparent bottom portion is set on the placing part, and
    the first ring lighting part is located at a position which is higher than the transparent bottom portion and lower than an upper end of the placing item.

11. The medicine photographing device according to claim 9, wherein a placing item including a transparent cylindrical member is set on the placing part, and
    the cylindrical member is inserted into the ring of the first ring lighting part when the placing item is set on the placing part.

12. The medicine photographing device according to claim 1, wherein the upper light source includes a plurality of bar lighting parts, and
    the lower light source includes a plurality of bar lighting parts.

13. The medicine photographing device according to claim 12, wherein at least one of the bar lighting parts is provided so as to be parallel to a front-back direction of the medicine photographing device.

14. The medicine photographing device according to claim 1, wherein the first camera can photograph a color image, and the second camera can photograph a color image.

15. The medicine photographing device according to claim 1, wherein the placing part, the first camera, the second camera, the upper light source and the lower light source are contained in a case, and at least a part of a front surface of the case can be opened and closed at a position higher than the placing part.

16. The medicine photographing device according to claim 15, wherein an outer front surface of the case includes an inclined portion provided at a position higher than the placing part, and a distance between the inclined portion and a rear surface of the medicine photographing device decreases from the lower side to the upper side.

17. The medicine photographing device according to claim 1, wherein the placing part of the medicine photographing device is communicated with outer spaces on a front direction and a left-right direction of the medicine photographing device at a position which is lower than the first camera and higher than the second camera.

18. The medicine photographing device according to claim 1, wherein a placing item including a bottom portion and a transparent plate provided on the bottom portion is set on the placing part.

19. The medicine photographing device according to claim 1, wherein a placing item including a transparent bottom portion is set on the placing part, and a non-transparent member including an upper surface and a concave portion for placing capsule formed on the upper surface is set on the transparent bottom portion.

20. The medicine photographing device according to claim 1, wherein the non-transparent area provided on the placing item is formed in a ring.

21. The medicine photographing device according to claim 1, wherein the non-transparent area provided on the placing item is black.

\* \* \* \* \*